United States Patent [19]
Chappell et al.

[11] Patent Number: 5,349,126
[45] Date of Patent: Sep. 20, 1994

[54] PROCESS AND COMPOSITION FOR INCREASING SQUALENE AND STEROL ACCUMULATION IN HIGHER PLANTS

[75] Inventors: Joseph Chappell, Lexington, Ky.; Court A. Saunders, Clarendon Hills; Fred R. Wolf, Naperville, both of Ill.

[73] Assignee: Amoco Corporation, Naperville, Ill.

[21] Appl. No.: 934,374

[22] Filed: Aug. 14, 1992

Related U.S. Application Data

[63] Continuation-in-part of Ser. No. 596,467, Oct. 12, 1990.

[51] Int. Cl.$^5$ .......................... A01H 1/04; A01H 5/10; C12N 15/00; C12P 21/04
[52] U.S. Cl. ..................... 800/205; 800/250; 800/255; 800/DIG. 11; 800/DIG. 26; 800/DIG. 27; 800/DIG. 43; 800/DIG. 44; 800/DIG. 46; 800/DIG. 55; 800/DIG. 56; 435/172.3; 435/69.1; 435/70.1; 435/240.4
[58] Field of Search ................... 435/69.1, 70.1, 172.3, 435/183, 240.4, 320.1; 800/205, 250, DIG. 43

[56] References Cited

U.S. PATENT DOCUMENTS 4,956,282 9/1990 Goodman et al. ............... 435/69.51

FOREIGN PATENT DOCUMENTS 89310973.6 10/1989 European Pat. Off. .
PCT/US89/- 01309 3/1989 PCT Int'l Appl. .

OTHER PUBLICATIONS

Caelles, C. et al. 1991 (Abstract #853) "Isolation and Structural Characterization of a cDNA Encoding *Arabidopsis thalia* 3-hydroxy-3-methylglutaryl Coenzyme A Reductase" *Plant Molecular Biology* 13:627–638.
Chappell, J. et al. 1991 (Abstract #853) "Is HMG–CoA Reductase a Rate Limiting Step for Isoprenoid Metabolism?" *Plant Physiology (Supplement)* 96(1):127.
Narita, J. et al. 1989 "Tomato Hydroxymethylglutaryl-CoA Reductase is Required Early in Fruit Development But Not During Ripening" *The Plant Cell* 1:181–190.
Gil, G. et al. 1985, "Membrane-Bound Domain of HMG CoA Reductase Is Required for Sterol-Enhanced Degradation of the Enzyme" *Cell* 41:249–258.
Chin, D. et al. 1985 (Biol. Abstract 80(2):AB-376 #12523) "Sterols Accelerate Degradation of Hamster 3-hydroxy-3-methylglutaryl Coenzyme A Reductase Encoded By a Constitutively Expressed Complementary DNA" *Mol. Cell Biol.* 5(4):634–641.
Learned, R. et al. 1989. "3-Hydroxy-3-Methylglutaryl-Coenzyme A Reductase From *Arabidopsis thaliana* Is Structurally Distinct from the Yeast and Animal Enzymes" *Proc. Natl. Acad. Sci.* 86:2779–2783.
Downing, J. et al. 1980 (Chem Abstracts 93:484 #93:65791y) "The Isolation of Two Mutants of Saccharomyces cerevisiae Which Demonstrate Increased Activity of 3-Hydroxy-3-methylglutaryl Coenzyme a Reductase".
LaGrimini, L. et al. 1990. "Peroxidase-Induced Wilting in Transgenic Tobacco Plants" *The Plant Cell* 2:7–18.
Downing et al (1980) 94(3): 974–979.
Shigematsu et al (1982) 46(11): 2877–2879.
Vaeck et al (1987) Nature 328: 33–37.
Bradford et al (1982) Can. J. Bot. 60: 1469–1473.
Chappell et al (1989) Plant Cell Reports 8: 48–52.
Chin et al (1984) Nature 308: 613–617.
Horsch et al (1985) Science 227: 1229–1231.

*Primary Examiner*—David T. Fox
*Assistant Examiner*—E. F. McElwain
*Attorney, Agent, or Firm*—Joanne M. Giesser

[57] ABSTRACT

A process of increasing squalene and sterol accumulation in a transgenic plant by increasing the amount of a gene encoding a polypeptide having HMG-CoA reductase activity is disclosed. The amount is preferably increased by transforming plant cells with a recombinant DNA molecule comprising a vector operatively linked to an exogenous DNA segment that encodes a polypeptide having HMG-CoA reductase activity, and a promoter suitable for driving the expression of said polypeptide to form a transformed plant cell and regenerating a transgenic plant from that transformed cell. Also disclosed are a process of increasing pest resistance in a transgenic plant, transgenic plants and transgenic seeds capable of germinating into transgenic plants.

11 Claims, 23 Drawing Sheets

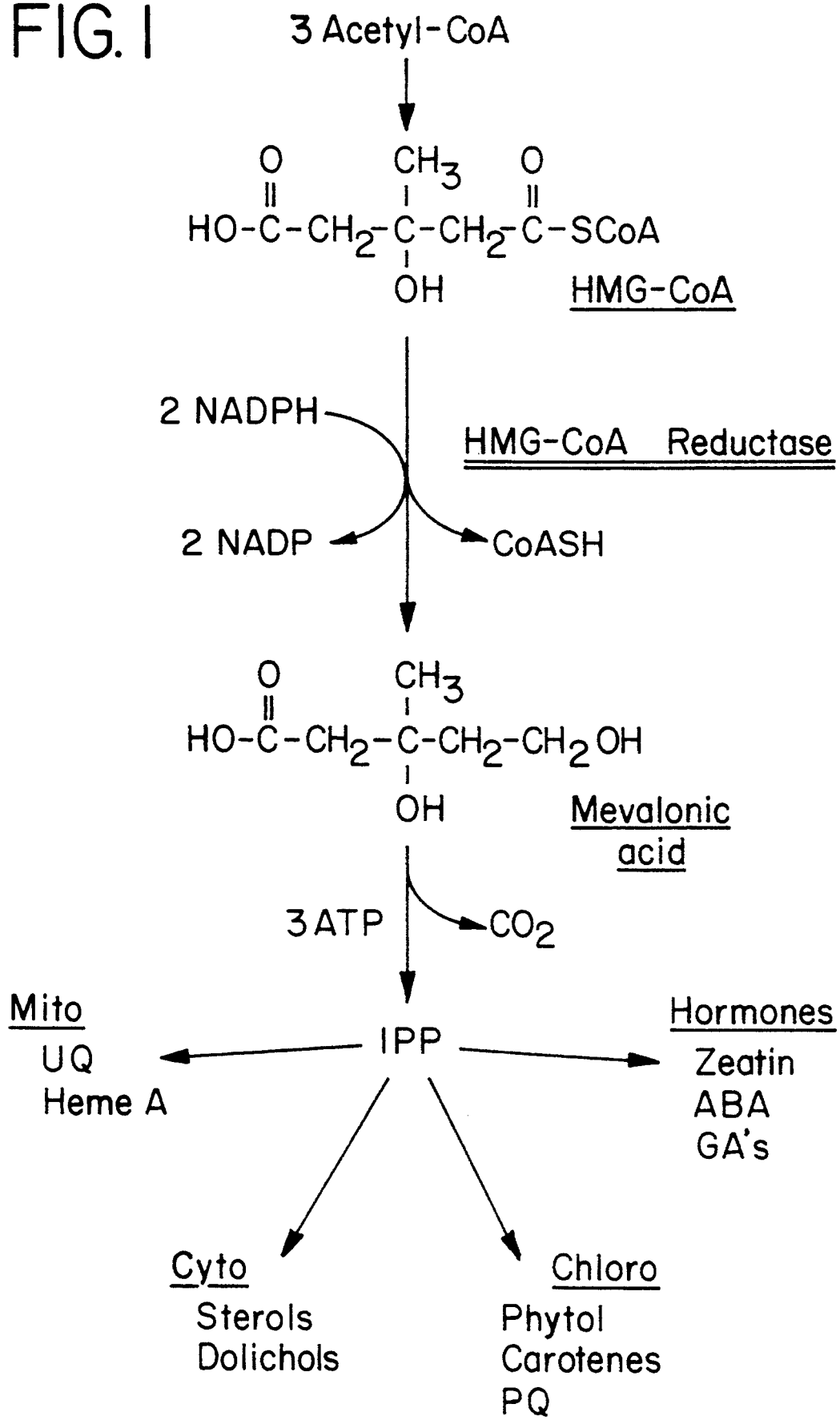
FIG. I

```
TGTATGTCTT GTCTTTCTCC TAAGGGGCGT AGGCTCATTG ATAACTCATG TCCTCACCTT        60

GCACTCCTTT TGGAATTATT TGGTTTGAGT GAAGAAGACC GGACCTTCGA GGTTCGCAAC       120

TTAAACAATA GACTTGTGAG GATCCAGGGA CCGAGTGGCT ACA ATG TTG TCA CGA        175
                                              Met Leu Ser Arg
                                               1

CTT TTC CGT ATG CAT GGC CTC TTT GTG GCC TCC CAT CCC TGG GAA GTT        223
Leu Phe Arg Met His Gly Leu Phe Val Ala Ser His Pro Trp Glu Val
 5                   10                  15                  20

ATT GTG GGG ACG GTG ACA CTT ACC ATC TGT ATG ATG TCC ATG AAC ATG        271
Ile Val Gly Thr Val Thr Leu Thr Ile Cys Met Met Ser Met Asn Met
             25                  30                  35

TTC ACT GGC AAC AAC AAG ATC TGT GGT TGG AAT TAC GAG TGC CCA AAA        319
Phe Thr Gly Asn Asn Lys Ile Cys Gly Trp Asn Tyr Glu Cys Pro Lys
         40                  45                  50

TTT GAG GAG GAT GTA TTG AGC AGT GAC ATC ATC CTC ACC ATA ACA ACA        367
Phe Glu Glu Asp Val Leu Ser Ser Asp Ile Ile Leu Thr Ile Thr
     55                  60                  65

CGG TGC ATC GCC ATC CTG TAC ATT TAC TTC CAG TTC CAG AAC TTA CGT        415
Arg Cys Ile Ala Ile Leu Tyr Ile Tyr Phe Gln Phe Gln Asn Leu Arg
 70                  75                  80
```

Figure 2A

| | | | | | | | | | | | | | | | | |
|---|---|---|---|---|---|---|---|---|---|---|---|---|---|---|---|---|
| CAG | CTT | GGG | TCG | AAG | TAT | ATT | TTA | GGT | ATT | GCT | GGC | CTG | TTC | ACA | ATT | 463 |
| Gln | Leu | Gly | Ser | Lys | Tyr | Ile | Leu | Gly | Ile | Ala | Gly | Leu | Phe | Thr | Ile | |
| 85 | | | | | 90 | | | | | 95 | | | | | 100 | |
| TTC | TCA | AGT | TTT | GTC | TTT | AGT | ACA | GTC | ATT | CAC | TTC | TTA | GAC | AAA | | 511 |
| Phe | Ser | Ser | Phe | Val | Phe | Ser | Thr | Val | Ile | His | Phe | Leu | Asp | Lys | | |
| | | 105 | | | | | 110 | | | | | 115 | | | | |
| GAA | CTG | ACG | GGC | TTA | AAT | GAA | GCT | TTG | CCC | TTT | TTC | CTG | CTT | TTG | ATT | 559 |
| Glu | Leu | Thr | Gly | Leu | Asn | Glu | Ala | Leu | Pro | Phe | Phe | Leu | Leu | Leu | Ile | |
| | 120 | | | | | 125 | | | | | 130 | | | | | |
| GAC | CTT | TCT | AGA | GCG | AGT | GCA | CTA | GCA | AAG | TTT | CTG | CTA | AGT | TCA | AAC | 607 |
| Asp | Leu | Ser | Arg | Ala | Ser | Ala | Leu | Ala | Lys | Phe | Leu | Leu | Ser | Ser | Asn | |
| | 135 | | | | | 140 | | | | | 145 | | | | | |
| TCT | CAG | GAT | GAA | GTA | AGG | GAA | AAT | ATA | GCT | CGC | GGA | ATG | GCA | ATT | CTG | 655 |
| Ser | Gln | Asp | Glu | Val | Arg | Glu | Asn | Ile | Ala | Arg | Gly | Met | Ala | Ile | Leu | |
| 150 | | | | | 155 | | | | | 160 | | | | | | |
| GGC | CCC | ACA | TTC | ACC | CTT | GAT | GCT | CTT | GTG | GAA | TGT | CTT | GTA | ATT | GGA | 703 |
| Gly | Pro | Thr | Phe | Thr | Leu | Asp | Ala | Leu | Val | Glu | Cys | Leu | Val | Ile | Gly | |
| 165 | | | | | 170 | | | | | 175 | | | | | 180 | |
| GTT | GGC | ACC | ATG | TCA | GGG | GTG | CGT | CAG | CTT | GAA | ATC | ATG | TGC | TGC | TTT | 751 |
| Val | Gly | Thr | Met | Ser | Gly | Val | Arg | Gln | Leu | Glu | Ile | Met | Cys | Cys | Phe | |
| | 185 | | | | | 190 | | | | | 195 | | | | | |

Figure 2B

```
GGC TGC ATG TCT GTG CTT GCC AAC TAC TTC GTG TTC ATG ACA TTT TTC      799
Gly Cys Met Ser Val Leu Ala Asn Tyr Phe Val Phe Met Thr Phe Phe
            200                 205                 210

CCA GCG TGT GTG TCC CTG GTC CTT GAG CTT TCT CGG GAA AGT CGA GAG      847
Pro Ala Cys Val Ser Leu Val Leu Glu Leu Ser Arg Glu Ser Arg Glu
            215                 220                 225

GGT CGT CCA ATT TGG CAG CTT AGC CAT TTT GCC CGA GTT TTG GAA GAA      895
Gly Arg Pro Ile Trp Gln Leu Ser His Phe Ala Arg Val Leu Glu Glu
            230                 235                 240

GAA GAG AAT AAA CCA AAC CCT GTA ACC CAA AGG GTC AAG ATG ATT ATG      943
Glu Glu Asn Lys Pro Asn Pro Val Thr Gln Arg Val Lys Met Ile Met
            245                 250                 255                 260

TCT TTA GGT TTG GTT CTT GTT CAT GCT CAC AGT CGA TGG ATA GCT GAT      991
Ser Leu Gly Leu Val Leu Val His Ala His Ser Arg Trp Ile Ala Asp
            265                 270                 275

CCT TCC CCT CAG AAT AGC ACA ACA GAA CAT TCT AAA GTC TCC TTG GGA      1039
Pro Ser Pro Gln Asn Ser Thr Thr Glu His Ser Lys Val Ser Leu Gly
            280                 285                 290

CTG GAT GAA GAT GTG TCC AAG AGA ATT GAA CCA AGT GTT TCT CTC TGG      1087
Leu Asp Glu Asp Val Ser Lys Arg Ile Glu Pro Ser Val Ser Leu Trp
            295                 300                 305
```

Figure 2C

```
CAG TTT TAT CTC TCC AAG ATG ATC AGC ATG GAC ATT GAA CAA GTG GTT   1135
Gln Phe Tyr Leu Ser Lys Met Ile Ser Met Asp Ile Glu Gln Val Val
310                 315                 320

ACC CTG AGC TTA GCT TTT CTG TTG GCT GTC AAG TAC ATT TTC TTT GAA   1183
Thr Leu Ser Leu Ala Phe Leu Leu Ala Val Lys Tyr Ile Phe Phe Glu
325                 330                 335                 340

CAA GCA GAG ACA TCC ACA CTG TCT TTA AAA AAT CCT ATC ACG TCT       1231
Gln Ala Glu Thr Ser Thr Leu Ser Leu Lys Asn Pro Ile Thr Ser
    345                 350                 355

CCT GTC GTG ACC CCA AAG GCT CCA GAC AAC TGT TGT AGA CGG GAG       1279
Pro Val Val Thr Pro Lys Ala Pro Asp Asn Cys Cys Arg Arg Glu
360                 365                 370

CCT CTT GTT AGA AGG AGC GAG AAG CTT TCA TCG GTT GAG GAG GAG       1327
Pro Leu Val Arg Arg Ser Glu Lys Leu Ser Ser Val Glu Glu Glu
375                 380                 385

CCT GGG GTG AGC CAA GAT AGA AAA GTT GAG GTT ATA AAA CCA TTA GTG   1375
Pro Gly Val Ser Gln Asp Arg Lys Val Glu Val Ile Lys Pro Leu Val
390                 395                 400

GTG GAA ACT GAG AGT GCA AGC AGA GCT ACA TTT GTG CTT GGC GCC TCT   1423
Val Glu Thr Glu Ser Ala Ser Arg Ala Thr Phe Val Leu Gly Ala Ser
405                 410                 415                 420
```

Figure 2D

```
GGG ACC AGC CCT CCA GTG GCA GCG AGG ACA CAG GAG CTT GAA ATT GAA    1471
Gly Thr Ser Pro Pro Val Ala Ala Arg Thr Gln Glu Leu Glu Ile Glu
                425                 430                 435

CTC CCC AGT GAG GAG CCT CGG CCT AAT GAA GAA TGT CTG CAG ATA CTG GAG    1519
Leu Pro Ser Glu Glu Pro Arg Pro Asn Glu Glu Cys Leu Gln Ile Leu Glu
            440                 445                 450

AGT GCC GAG AAA GGT GCA AAG TTC CTT AGC GAT GCA GAG ATC ATC CAG    1567
Ser Ala Glu Lys Gly Ala Lys Phe Leu Ser Asp Ala Glu Ile Ile Gln
        455                 460                 465

TTG GTC AAT GCC AAG CAC ATC CCA GCC TAC AAA TTG CTG GAA ACC TTA ATG    1615
Leu Val Asn Ala Lys His Ile Pro Ala Tyr Lys Leu Leu Glu Thr Leu Met
    470                 475                 480

GAA ACT CAT GAA CGT GGT GTA TCT ATT CGC CGG CAG CTC CTC TCC ACA    1663
Glu Thr His Glu Arg Gly Val Ser Ile Arg Arg Gln Leu Leu Ser Thr
485                 490                 495                 500

AAG CTT CCA GAG CCT TCT TCT CTG CAG TAC CTG CCT TAC AGA GAT TAT    1711
Lys Leu Pro Glu Pro Ser Ser Leu Gln Tyr Leu Pro Tyr Arg Asp Tyr
            505                 510                 515

AAT TAT TCC CTG GTG ATG GGA GCT TGC TGT GAG AAT GTG ATC GGA TAT    1759
Asn Tyr Ser Leu Val Met Gly Ala Cys Cys Glu Asn Val Ile Gly Tyr
        520                 525                 530
```

Figure 2E

```
ATG CCC ATC CCT GTC GGA GTA GCA GGG CCT CTG TGC CTG GAT GGT AAA    1807
Met Pro Ile Pro Val Gly Val Ala Gly Pro Leu Cys Leu Asp Gly Lys
        535             540             545

GAG TAC CAG GTT CCA ATG GCA ACA ACG GAA GGC TGT CTG GTG GCC AGC    1855
Glu Tyr Gln Val Pro Met Ala Thr Thr Glu Gly Cys Leu Val Ala Ser
        550             555             560

ACC AAC AGA GGC TGC GAT GCA ATA GGT AGG CTT GGT GGA GGT GCC AGC    1903
Thr Asn Arg Gly Cys Asp Ala Ile Gly Arg Leu Gly Gly Gly Ala Ser
        565             570             575             580

CGG GTC CTT GCA GAT TCT GCA ATG ACC CGG GGC CCA GTG CGT CTT CCT    1951
Arg Val Leu Ala Asp Ser Ala Met Thr Arg Gly Pro Val Arg Leu Pro
        585             590             595

CGT GCT TGT GAT GTG ATA AAG GAA GTG CTT GAA ACA CCC GAA            1999
Arg Ala Cys Asp Val Ile Lys Glu Val Leu Glu Thr Pro Glu
        600             605             610

GGG TTT GCG GTC ATC AAG GAC GCC TGG TTC GAT AGC ACT AGC AGA TTT GCA    2047
Gly Phe Ala Val Ile Lys Asp Ala Trp Phe Asp Ser Thr Ser Arg Phe Ala
        615             620             625

CGT CTA CAG AAG CTT CAT GTG ACC ATG GCA GGG CGC AAC CTG TAC ATC    2095
Arg Leu Gln Lys Leu His Val Thr Met Ala Gly Arg Asn Leu Tyr Ile
        630             635             640
```

Figure 2F

```
CGT TTC CAG TCC AAG ACA GGG GAT GCC ATG GGG ATG AAC ATG ATT TCC    2143
Arg Phe Gln Ser Lys Thr Gly Asp Ala Met Gly Met Asn Met Ile Ser
645                 650                 655                 660

AAG GGC ACT GAG AAA GCA CTT CTG AAG CTT CTG CAG GAG TTC TTT CCT GAA    2191
Lys Gly Thr Glu Lys Ala Leu Leu Lys Leu Leu Gln Glu Phe Phe Pro Glu
            665                 670                 675

ATG CAG ATT CTG GCA GTT AGT GGT AAC TAC TGC ACT GAC AAG AAA CCT    2239
Met Gln Ile Leu Ala Val Ser Gly Asn Tyr Cys Thr Asp Lys Lys Pro
            680                 685                 690

GCC GCC ATA AAC TGG ATC GAG GGA AGA GGA AAG ACA GTT GTG TGT GAA    2287
Ala Ala Ile Asn Trp Ile Glu Gly Arg Gly Lys Thr Val Val Cys Glu
        695                 700                 705

GCT GTT ATT CCA GCC AAG GTG GTG AGA GAA GTA TTA AAG ACA ACT ACG    2335
Ala Val Ile Pro Ala Lys Val Val Arg Glu Val Leu Lys Thr Thr Thr
710                 715                 720

GAA GCT ATG ATT GAC GTA AAC AAG AAT CTT GTG GGT TCT GCC    2383
Glu Ala Met Ile Asp Val Asn Lys Asn Leu Val Gly Ser Ala
725                 730                 735                 740

ATG GCT GGG AGC ATA GGA GGC TAC AAT GCC CAT GCA AAC ATC GTC    2431
Met Ala Gly Ser Ile Gly Gly Tyr Asn Ala His Ala Asn Ile Val
            745                 750                 755
```

Figure 2G

| | | | | | | | | | | | | | | | | |
|---|---|---|---|---|---|---|---|---|---|---|---|---|---|---|---|---|
| ACT | GCT | ATC | TAC | ATT | GCA | TGT | GGC | CAG | GAT | GCA | GCA | CAG | AAT | GTG | GGG | 2479 |
| Thr | Ala | Ile | Tyr | Ile | Ala | Cys | Gly | Gln | Asp | Ala | Ala | Gln | Asn | Val | Gly | |
| | | 760 | | | | | 765 | | | | | 770 | | | | |
| AGT | TCA | AAC | TGT | ATT | ACT | TTA | ATG | GAA | GCA | AGT | GGT | CCC | ACG | AAT | GAA | 2527 |
| Ser | Ser | Asn | Cys | Ile | Thr | Leu | Met | Glu | Ala | Ser | Gly | Pro | Thr | Asn | Glu | |
| | 775 | | | | | 780 | | | | | 785 | | | | | |
| GAC | TTG | TAT | ATC | AGC | TGC | ACC | ATG | CCA | TCT | ATA | GAG | ATA | GGA | ACT | GTG | 2575 |
| Asp | Leu | Tyr | Ile | Ser | Cys | Thr | Met | Pro | Ser | Ile | Glu | Ile | Gly | Thr | Val | |
| 790 | | | | | 795 | | | | | 800 | | | | | | |
| GGT | GGG | ACC | AAC | CTC | CTA | CCA | CAG | CAG | GCC | TGT | CTG | CAG | ATG | CTA | | 2623 |
| Gly | Gly | Thr | Asn | Leu | Leu | Pro | Gln | Gln | Ala | Cys | Leu | Gln | Met | Leu | | |
| 805 | | | | 810 | | | | | 815 | | | | | 820 | | |
| GGT | GTT | CAA | GGA | GCG | TGC | AAA | GAC | AAT | CCT | GGA | GAA | AAT | GCA | CGG | CAA | 2671 |
| Gly | Val | Gln | Gly | Ala | Cys | Lys | Asp | Asn | Pro | Gly | Glu | Asn | Ala | Arg | Gln | |
| | | | 825 | | | | | 830 | | | | | 835 | | | |
| CTT | GCC | CGA | ATT | GTG | TGT | ACT | GTA | ATG | GCT | GGG | GAG | TTG | TCC | TTG | | 2719 |
| Leu | Ala | Arg | Ile | Val | Cys | Thr | Val | Met | Ala | Gly | Glu | Leu | Ser | Leu | | |
| | | 840 | | | | | 845 | | | | | 850 | | | | |
| ATG | GCA | GCA | TTG | GCA | GCA | GGA | CAT | CTT | GTT | AGA | AGT | CAC | ATG | GTT | CAT | 2767 |
| Met | Ala | Ala | Leu | Ala | Ala | Gly | His | Leu | Val | Arg | Ser | His | Met | Val | His | |
| 855 | | | | | 860 | | | | | 865 | | | | | | |

Figure 2H

```
AAC AGA TCG AAG ATA AAT TTA CAA GAT CTG CAA GGA ACG TGC ACC AAG      2815
Asn Arg Ser Lys Ile Asn Leu Gln Asp Leu Gln Gly Thr Cys Thr Lys
870                 875                 880

AAG TCA GCT TGAGCAGCCT GACAGTATTG AACTGAAACA CGGGCATTGG              2864
Lys Ser Ala
885

GTTCTCAAGG ACTAACATGA AATCTGTGAA TTAAAAATCT CAATGCAGTG TCTTGTGGAA    2924

GATGAATGAA CGTGATCAGT GAGACGCCTG CTTGGTTTCT GGCTCTTTCA GAGACGTCTG    2984

AGGTCCTTTG CTCGGAGACT CCTCAGATCT GGAAACAGTG TGGTCCTTCC CATGCTGTAT    3044

TCTGAAAAGA TCTCATATGG ATGTTGTGCT CTGAGCACCA CAGATGTGAT CTGCAGCTCG    3104

TTTCTGAAAT GATGGAGTTC ATGGTGATCA GTGTGAGACT GGCCTCTCCC AGCAGGTAA     3164

AAATGGAGTT TTAAATTATA CTGTAGCTGA CAGTACTTCT GATTTTATAT TTATTTAGTC    3224

TGAGTTGTAG AACTTTGCAA TCTAAGTTTA TTTTTTGTAA CCTAATAATT CATTTGGTGC    3284

TGGTCTATTG ATTTTTGGGG GTAAACAATA TTATTCTTCA GAAGGGGACC TACTTCTTCA    3344

TGGGAAGAAT TACTTTTATT CTCAAACTAC AGAACAATGT GCTAAGCAGT GCTAAATTGT    3404

TCTCATGAAG AAAACAGTCA CTGCATTTAT CTCTGTAGGC CTTTTTTCAG.AGAGGCCTTG   3464
```

Figure 2I

```
TCTAGATTTT  TGCCAGCTAG  GCTACTGCAT  GTCTTAGTGT  CAGGCCTTAG  GAAAGTGCCA  3524
CGCTCTGCAC  TAAAGATATC  AGAGCTCTTG  GTGTTACTTA  GACAAGAGTA  TGAGCAAGTC  3584
GGACCTCTCA  GAGTGTGGGA  ACACAGTTTT  GAAAGAAAAA  CCATTTCTCT  AAGCCAATTT  3644
TCTTTAAAGA  CATTTTAACT  TATTTAGCTG  AGTTCTAGAT  TTTTCGGGTA  AACTATCAAA  3704
TCTGTATATG  TTGTAATAAA  GTGTCTTATG  CTAGGAGTTT  ATTCAAAGTG  TTTAAGTAAT  3764
AAAGGACTC   AAATTTACAC  TGATAAAATA  CCTGCTTGCT  GGCCAGAGAA  GACAGTGCTC  3824
ATTAGCGTTG  TCCAGGAAAC  CCTGCTTGCT  TGCCAAGCCT  AATGAAGGA   AAGTCAGCTT  3884
TCAGAGCCAA  TGATGGAGGC  CACATGAATG  GCCCTGGAGC  TGTGTGCCTT  GTTCTGTGGC  3944
CAGGAGCTTG  GTGACTGAAT  CATTTACGGG  CTCCCTTTGAT GGACCCATAA  AAGCTCTTAG  4004
CTTCCTCAGG  GGGTCAGCAG  AGTTGTTGAA  TCTTAATTTT  TTTTTTAATG  TACCAGTTTT  4064
GTATAAATAA  TAATAAAGAG  CTCCTTATTT  TGTATTCTAT  CTAATGCTTC  GAGTTCAGTC  4124
TTGGGAAGCT  GACATCTCAT  GTAGAAGATG  GACTCTGAAA  GACATTCCAA  GAGTGCAGCG  4184
GCATCATGGG  AGCCTCTTAG  TGATTGTGTG  TCAGTATTAT  TGTGGAAGAT  TGACTTTGCT  4244
TTTGTATGTG  AAGTTTCAGA  TTGCTCCCTCT TGTGACTTTT TAGCCAGTAA  CATTTTATTT  4304
```

Figure 2J

```
ACCTGAGCTT GTCATGGAAG TGGCAGTGAA AAGTATTGAG TATTCATGCT GGTGACTGTA    4364

ACCAATGTCA TCTTGCTAAA AACTCATGTT TTGTACAATT ACTAAATTGT ATACATTTTG    4424

TTATAGAATA CTTTTTCCAG TTGAGTAAAT TATGAAAGGA AGTTAACATT AACAGGTGTA    4484

AGCGGTGGCT TTTTAAAAT GAAGGATTAA CCCTAAGCCC GAGACCCAGA AGCTAGCAAA     4544

GTCTGGCAGA GTGGTAAACT. GTCCTGCTGG GGCCATCCAA TCATCTCTCT CCATTACACT   4604

TTCTAACTTT GCAGCATTGG TGCTGGCCAG TGTATTGTTT CATTGATCTT CCTTACGCTT    4664

AGAGGGTTTG ATTGGTTCAG ATCTATAATC TCAGCCACAT TGTCTTGGTA TCAGCTGGAG    4724

AGAGTTAAGA GGAAGGGAAA ATAAAGTTCA GATAGCCAAA ACAC                     4768
```

Figure 2K

```
TTTATTAACT TATTTTTTC TTCTTTCTAC CCAATTCTAG TCAGGAAAAG ACTAAGGCT          60

GGAACATAGT GTATCATTGT CTAATTGTTG ATACAAAGTA GATAAATACA TAAAACAAGC       120

ATG CCG CCG CTA TTC AAG GGA CTG AAA CAG ATG GCA AAG CCA ATT GCC        168
Met Pro Pro Leu Phe Lys Gly Leu Lys Gln Met Ala Lys Pro Ile Ala
 1                   5                  10                  15

TAT GTT TCA AGA TTT TCG GCG AAA CGA CCA ATT CAT ATA ATA CTT TTT        216
Tyr Val Ser Arg Phe Ser Ala Lys Arg Pro Ile His Ile Ile Leu Phe
            20                  25                  30

TCT CTA ATC ATA TCC GCA TTC GCT TAT CTA TCC GTC ATT CAG TAT TAC        264
Ser Leu Ile Ile Ser Ala Phe Ala Tyr Leu Ser Val Ile Gln Tyr Tyr
        35                  40                  45

TTC AAT GGT TGG CAA CTA GAT TCA AAT AGT GTT TTT GAA ACT GCT CCA        312
Phe Asn Gly Trp Gln Leu Asp Ser Asn Ser Val Phe Glu Thr Ala Pro
    50                  55                  60

AAT AAA GAC TCC AAC ACT CTA TTT CAA GAA TGT TCC CAT TAC TAC AGA        360
Asn Lys Asp Ser Asn Thr Leu Phe Gln Glu Cys Ser His Tyr Tyr Arg
65                  70                  75                  80

GAT TCC TCT CTA GAT GGT TGG GTA TCA ATC ACC GCG CAT GAA GCT AGT        408
Asp Ser Ser Leu Asp Gly Trp Val Ser Ile Thr Ala His Glu Ala Ser
                85                  90                  95
```

Figure 3A

| | | | | | | | |
|---|---|---|---|---|---|---|---|
| GAG | TTA | CCA | GCC | CCA | CAC | CAT | TAC | TAT | CTA | TTA | AAC | CTG | AAC | TTC | AAT |
| Glu | Leu | Pro | Ala | Pro | His | His | Tyr | Tyr | Leu | Leu | Asn | Leu | Asn | Phe | Asn |
| | | 100 | | | | | 105 | | | | 110 | | | | |

456

| AGT | CCT | AAT | GAA | ACT | GAC | TCC | ATT | CCA | GAA | CTA | GCT | AAC | ACG | GTT | TTT |
|---|---|---|---|---|---|---|---|---|---|---|---|---|---|---|---|
| Ser | Pro | Asn | Glu | Thr | Asp | Ser | Ile | Pro | Glu | Leu | Ala | Asn | Thr | Val | Phe |
| | | 115 | | | | | 120 | | | | | 125 | | | |

504

| GAG | AAA | ACA | AAA | TAT | ATT | CTG | CAA | GAA | GAT | CTC | AGT | GTT | TCC |
|---|---|---|---|---|---|---|---|---|---|---|---|---|---|
| Glu | Lys | Asp | Asn | Thr | Lys | Tyr | Ile | Leu | Gln | Glu | Asp | Leu | Ser | Val | Ser |
| 130 | | | | | 135 | | | | | 140 | | | | | |

552

| AAA | GAA | ATT | TCT | TCT | ACT | GAT | GGA | ACG | AAA | TGG | AGG | TTA | AGA | AGT | GAC |
|---|---|---|---|---|---|---|---|---|---|---|---|---|---|---|---|
| Lys | Glu | Ile | Ser | Ser | Thr | Asp | Gly | Thr | Lys | Trp | Arg | Leu | Arg | Ser | Asp |
| 145 | | | | | 150 | | | | | 155 | | | | | 160 |

600

| AGA | AAA | AGT | CTT | TTC | GAC | GTA | AAG | ACG | TTA | GCA | TAT | TCT | CTC | TAC | GAT |
|---|---|---|---|---|---|---|---|---|---|---|---|---|---|---|---|
| Arg | Lys | Ser | Leu | Phe | Asp | Val | Lys | Thr | Leu | Ala | Tyr | Ser | Leu | Tyr | Asp |
| | | | | 165 | | | | | 170 | | | | | 175 | |

648

| GTA | TTT | TCA | GAA | AAT | GTA | ACC | CAA | GCA | GAC | CCG | TTT | GAC | GTC | CTT | ATT |
|---|---|---|---|---|---|---|---|---|---|---|---|---|---|---|---|
| Val | Phe | Ser | Glu | Asn | Val | Thr | Gln | Ala | Asp | Pro | Phe | Asp | Val | Leu | Ile |
| | 180 | | | | | 185 | | | | | 190 | | | | |

696

| ATG | GTT | ACT | GCC | TAC | CTA | ATG | ATG | TTC | TAC | ACC | ATA | TTC | GGC | CTC | TTC |
|---|---|---|---|---|---|---|---|---|---|---|---|---|---|---|---|
| Met | Val | Thr | Ala | Tyr | Leu | Met | Met | Phe | Tyr | Thr | Ile | Phe | Gly | Leu | Phe |
| | 195 | | | | | 200 | | | | | 205 | | | | |

```
AAT GAC ATG AGG AAG ACC GGG TCA AAT TTT TGG TTG AGC GCC TCT ACA   792
Asn Asp Met Arg Lys Thr Gly Ser Asn Phe Trp Leu Ser Ala Ser Thr
            210                 215                 220

GTG GTC AAT TCT GCA TCA CTT TTC TTA GCA TTG TAT GTC ACC CAA       840
Val Val Asn Ser Ala Ser Leu Phe Leu Ala Leu Tyr Val Thr Gln
225                 230                 235             240

TGT ATT CTA GGC AAA GAA GTT TCC GCA TTA ACT CTT TTT GAA GGT TTG   888
Cys Ile Leu Gly Lys Glu Val Ser Ala Leu Thr Leu Phe Glu Gly Leu
            245                 250                 255

CCT TTC ATT GTA GTT GGT GTT TTC AAG CAC AAA ATC AAG ATT GCC       936
Pro Phe Ile Val Val Gly Val Phe Lys His Lys Ile Lys Ile Ala
        260                 265                 270

CAG TAT GCC CTG GAG AAA TTT GAA AGA GTC GGT TTA TCT AAA AGG ATT  1032
Gln Tyr Ala Leu Glu Lys Phe Glu Arg Val Gly Leu Ser Lys Arg Ile
275                 280                 285

ACT ACC GAT GAA ATC GTT TTT GAA TCC GTG AGC GAA GGT GGT CGT      1032
Thr Thr Asp Glu Ile Val Phe Glu Ser Val Ser Glu Gly Gly Arg
        290                 295                 300

TTG ATT CAA GAC CAT TTG CTT TGT ATT TTT GCC TTT ATC GGA TGC TCT  1080
Leu Ile Gln Asp His Leu Leu Cys Ile Phe Ala Phe Ile Gly Cys Ser
305                 310                 315                 320
```

Figure 3C

```
ATG TAT GCT CAC CAA TTG AAG ACT TTG ACA AAC TTC TGC ATA TTA TCA   1128
Met Tyr Ala His Gln Leu Lys Thr Leu Thr Asn Phe Cys Ile Leu Ser
            325                 330                 335

GCA TTT ATC CTA ATT TTT GAA TTG ATT TTA ACT CCT ACA TTT TAT TCT   1176
Ala Phe Ile Leu Ile Phe Glu Leu Ile Leu Thr Pro Thr Phe Tyr Ser
            340                 345                 350

GCT ATC TTA GCG CTT AGA CTG GAA ATG AAT GTT ATC CAC AGA TCT ACT   1224
Ala Ile Leu Ala Leu Arg Leu Glu Met Asn Val Ile His Arg Ser Thr
            355                 360                 365

ATT ATC AAG CAA ACA TTA GAA GAC GGT GTT CCA GTT ACA GCA           1272
Ile Ile Lys Gln Thr Leu Glu Asp Gly Val Val Pro Ser Thr Ala
            370                 375                 380

AGA ATC ATT TCT AAA GCA GAA AAG AAA CTC GTA TCT TCT TTC TTA AAT   1320
Arg Ile Ile Ser Lys Ala Glu Lys Lys Leu Val Ser Ser Phe Leu Asn
   385                 390                 395                 400

CTC AGT GTG GTT GTC ATT ATG ATC ATG AAA CTC TCT GTC ATA CTG TTT   1368
Leu Ser Val Val Val Ile Ile Met Ile Met Lys Leu Leu Ser Val Ile Leu Leu Phe
            405                 410                 415

GTT TTC ATC AAC TTT TAT AAC TTT GGT GCA AAT TGG GTC AAT GAT GCC   1416
Val Phe Ile Asn Phe Tyr Asn Phe Gly Ala Asn Trp Val Asn Asp Ala
            420                 425                 430
```

Figure 3D

| | | | | | | | | | | |
|---|---|---|---|---|---|---|---|---|---|---|
| TTC Phe | AAT Asn | TCA Ser | TTG Leu | TAC Tyr | TTC Phe | GAT Asp | AAG Lys 440 | GAA Glu | CGT Arg | GTT Val | TCT Ser | CTA Leu 445 | CCA Pro | GAT Asp | TTT Phe | 1464 |
| ATT Ile | ACC Thr 450 | TCG Ser | AAT Asn | GCC Ala | TCT Ser | GAA Glu 455 | AAC Asn | TTT Phe | AAA Lys | GAG Glu | CAA Gln 460 | GCT Ala | ATT Ile | GTT Val | AGT Ser | 1512 |
| GTC Val 465 | ACC Thr | CCA Pro | TTA Leu | TAT Tyr 470 | TAC Tyr | AAA Lys | CCC Pro | ATT Ile | AAG Lys 475 | TCC Ser | TAC Tyr | CAA Gln | CGC Arg | ATT Ile 480 | | 1560 |
| GAG Glu | GAT Asp | ATG Met | GTT Val | CTT Leu 485 | CGT Arg | AAT Asn | GTC Val | AGT Ser 490 | GCC Ala | GTT Val | GCA Ala | ATT Ile | CGT Arg 495 | | | 1608 |
| GAT Asp | AGG Arg | TTC Phe | AGT Ser 500 | AAA Lys | TTA Leu | GTT Val | CTT Leu 505 | TCC Ser | GCC Ala | TTA Leu | GTA Val | TGC Cys 510 | AGT Ser | GCT Ala | | 1656 |
| GTC Val | ATC Ile 515 | AAT Asn | GTG Val | TAT Tyr | TTA Leu | TTG Leu 520 | AAT Asn | GCT Ala | GCT Ala | AGA Arg | ATT Ile 525 | CAT His | ACC Thr | AGT Ser | TAT Tyr | 1704 |
| ACT Thr 530 | GCA Ala | GAC Asp | CAA Gln | TTG Leu | GTG Val 535 | AAA Lys | ACT Thr | GAA Glu | GTC Val | ACC Thr 540 | AAG Lys | TCT Ser | TTT Phe | ACT Thr | | 1752 |

Figure 3E

```
GCT CCT GTA CAA AAG GCT TCT ACA CCA GTT TTA ACC AAT AAA ACA GTC    1800
Ala Pro Val Gln Lys Ala Ser Thr Pro Val Leu Thr Asn Lys Thr Val
545             550             555             560

ATT TCT GGA TCG AAA GTC AAA AGT TTA TCA TCT GCG CAA TCG AGC TCA    1848
Ile Ser Gly Ser Lys Val Lys Ser Leu Ser Ser Ala Gln Ser Ser Ser
        565             570             575

TCA CCT TCA TCT AGT GAG GAA GAT GAT GAT TCC CGC GAT ATT GAA        1896
Ser Gly Pro Ser Ser Ser Glu Glu Asp Asp Ser Arg Asp Ile Glu
580             585             590

AGC TTG GAT AAG AAA ATA CGT CCT TTA GAA GAA TTA GAA GCA TTA TTA    1944
Ser Leu Asp Lys Lys Ile Arg Pro Leu Glu Glu Leu Glu Ala Leu Leu
        595             600             605

AGT AGT GGA AAT ACA AAA CAA TTG AAG AAC AAA GAG GTC GCT GCC TTG    1992
Ser Ser Gly Asn Thr Lys Gln Leu Lys Asn Lys Glu Val Ala Ala Leu
610             615             620

GTT ATT CAC GGT AAG TTA CCT TTG TAC GCT TTG GAG AAA AAA TTA GGT    2040
Val Ile His Gly Lys Leu Pro Leu Tyr Ala Leu Glu Lys Lys Leu Gly
        625             630             635             640

GAT ACT ACG AGA GCG GTT GCC GTA CGT AGG AAG GCT CTT TCA ATT TTG    2088
Asp Thr Thr Arg Ala Val Ala Val Arg Arg Lys Ala Leu Ser Ile Leu
645             650             655
```

Figure 3F

| | | | | | | | | | | | | | | | |
|---|---|---|---|---|---|---|---|---|---|---|---|---|---|---|---|
| GCA | GAA | GCT | CCT | GTA | TTA | GCA | TCT | GAT | CGT | TTA | CCA | TAT | AAA | AAT | TAT | 2136 |
| Ala | Glu | Ala | Pro | Val | Leu | Ala | Ser | Asp | Arg | Leu | Pro | Tyr | Lys | Asn | Tyr |
| | | | 660 | | | | 665 | | | | 670 | | | | |
| GAC | TAC | GAC | CGC | GTA | TTT | GGC | GCT | CGT | TGT | GAA | AAT | GTT | ATA | GGT | TAC | 2184 |
| Asp | Tyr | Asp | Arg | Val | Phe | Gly | Ala | Cys | Cys | Glu | Asn | Val | Ile | Gly | Tyr |
| | 675 | | | | 680 | | | | 685 | | | | | | |
| ATG | CCT | TTG | CCC | GTT | GGT | ATA | GGC | GTT | GGT | GTT | ATC | GAT | GGT | ACA | 2232 |
| Met | Pro | Leu | Pro | Val | Gly | Ile | Gly | Val | Gly | Val | Ile | Asp | Gly | Thr |
| 690 | | | | 695 | | | | 700 | | | | | | | |
| TCT | TAT | CAT | ATA | CCA | ATG | GCA | ATA | GGC | GTT | GGT | TGT | TTG | GTA | GCT | TCT | 2280 |
| Ser | Tyr | His | Ile | Pro | Met | Ala | Ile | Gly | Val | Gly | Cys | Leu | Val | Ala | Ser |
| 705 | | | | | 710 | | | | 715 | | | | | | 720 |
| GCC | ATG | CGT | GGC | TGT | AAG | GCA | ATC | AAT | GCT | GGT | GGT | GCA | ACA | ACT | 2328 |
| Ala | Met | Arg | Gly | Cys | Lys | Ala | Ile | Asn | Ala | Gly | Gly | Ala | Thr | Thr |
| | | 725 | | | | | 730 | | | | | 735 | | | |
| GTT | TTA | ACT | AAG | GAT | GGT | ATG | ACA | AGA | GGC | GGT | CCA | GTA | GTC | CGT | TTC | CCA | 2376 |
| Val | Leu | Thr | Lys | Asp | Gly | Met | Thr | Arg | Gly | Gly | Pro | Val | Val | Arg | Phe | Pro |
| | | 740 | | | | | 745 | | | | | 750 | | | | |
| ACT | TTG | AAA | AGA | TCT | GGT | GCC | TGT | AAG | ATA | TGG | TTA | GAC | TCA | GAA | GAG | 2424 |
| Thr | Leu | Lys | Arg | Ser | Gly | Ala | Cys | Lys | Ile | Trp | Leu | Asp | Ser | Glu | Glu |
| 755 | | | | | 760 | | | | | 765 | | | | | |

Figure 3G

| | | | | | | | | | | | | | | | | |
|---|---|---|---|---|---|---|---|---|---|---|---|---|---|---|---|---|
| GGA | CAA | AAC | GCA | ATT | AAA | AAA | GCT | TTT | AAC | TCT | ACA | TCA | AGA | TTT | GCA | 2472 |
| Gly | Gln | Asn | Ala | Ile | Lys | Lys | Ala | Phe | Asn | Ser | Thr | Ser | Arg | Phe | Ala | |
| 770 | | | | | 775 | | | | | 780 | | | | | | |
| CGT | CTG | CAA | CAT | ATT | CAA | ACT | TGT | CTA | GCA | GGA | GAT | TTA | CTC | TTC | ATG | 2520 |
| Arg | Leu | Gln | His | Ile | Gln | Thr | Cys | Leu | Ala | Gly | Asp | Leu | Leu | Phe | Met | |
| 785 | | | | | 790 | | | | | 795 | | | | | 800 | |
| AGA | TTT | AGA | ACA | ACT | GGT | GAC | GCA | ATG | GGT | ATG | GGA | AAT | ATG | ATT | TCT | 2568 |
| Arg | Phe | Arg | Thr | Thr | Gly | Asp | Ala | Met | Gly | Met | Gly | Asn | Met | Ile | Ser | |
| | | 805 | | | | | 810 | | | | | 815 | | | | |
| AAA | GGT | GTC | GAA | TAC | TCA | TTA | AAG | CAA | ATG | GTA | GAA | GAG | TAT | GGC | TGG | 2616 |
| Lys | Gly | Val | Glu | Tyr | Ser | Leu | Lys | Gln | Met | Val | Glu | Glu | Tyr | Gly | Trp | |
| | 820 | | | | | 825 | | | | | 830 | | | | | |
| GAA | GAT | ATG | GAG | GTT | GTC | TCC | GTT | TCT | GGT | AAC | TAC | TGT | ACC | GAC | AAA | 2664 |
| Glu | Asp | Met | Glu | Val | Val | Ser | Val | Ser | Gly | Asn | Tyr | Cys | Thr | Asp | Lys | |
| 835 | | | | | 840 | | | | | 845 | | | | | | |
| AAA | CCA | GCT | GCC | ATC | AAC | TGG | ATC | GAA | GGT | CGT | GGT | AAG | AGT | GTC | GTC | 2712 |
| Lys | Pro | Ala | Ala | Ile | Asn | Trp | Ile | Glu | Gly | Arg | Gly | Lys | Ser | Val | Val | |
| | 850 | | | | | 855 | | | | | 860 | | | | | |
| GCA | GAA | GCT | ACT | ATT | CCT | GGT | GAT | GTT | GTC | AGA | AAA | GTG | TTA | AAA | AGT | 2760 |
| Ala | Glu | Ala | Thr | Ile | Pro | Gly | Asp | Val | Val | Arg | Lys | Val | Leu | Lys | Ser | |
| 865 | | | | | 870 | | | | | 875 | | | | | 880 | |

Figure 3H

| | | | | | | | | | | | | | | | |
|---|---|---|---|---|---|---|---|---|---|---|---|---|---|---|---|
| GAT | GTT | TCC | GCA | TTG | GTT | GAG | TTG | AAC | ATT | GCT | AAG | AAT | TTG | GTT | GGA |
| Asp | Val | Ser | Ala | Leu | Val | Glu | Leu | Asn | Ile | Ala | Lys | Asn | Leu | Val | Gly |
| | | | | 885 | | | | | 890 | | | | | 895 | |

2808

| TCT | GCA | ATG | GCT | GTT | GGT | GGG | TCT | GTT | GGT | TTT | AAC | GCA | CAT | GCT | AAT |
|---|---|---|---|---|---|---|---|---|---|---|---|---|---|---|---|
| Ser | Ala | Met | Ala | Val | Gly | Gly | Ser | Val | Gly | Phe | Asn | Ala | His | Ala | Asn |
| | | 900 | | | | | 905 | | | | | 910 | | | |

2856

| TTA | GTG | ACA | GCT | GTT | TTC | TTG | GCA | TTA | GGA | CAA | GAT | CCT | GCA | CAA | AAT |
|---|---|---|---|---|---|---|---|---|---|---|---|---|---|---|---|
| Leu | Val | Thr | Ala | Val | Phe | Leu | Ala | Leu | Gly | Gln | Asp | Pro | Ala | Gln | Asn |
| | 915 | | | | | 920 | | | | | 925 | | | | |

2904

| GTT | GAA | AGT | TCC | AAC | TGT | ATA | ACA | TTG | ATG | AAA | GAA | GTG | GAC | GGT | GAT |
|---|---|---|---|---|---|---|---|---|---|---|---|---|---|---|---|
| Val | Glu | Ser | Ser | Asn | Cys | Ile | Thr | Leu | Met | Lys | Glu | Val | Asp | Gly | Asp |
| 930 | | | | | 935 | | | | | 940 | | | | | |

2952

| TTG | AGA | ATT | TCC | GTA | TCC | ATG | CCA | TCC | ATC | GAA | GTA | GGT | ACC | ATC | GGT |
|---|---|---|---|---|---|---|---|---|---|---|---|---|---|---|---|
| Leu | Arg | Ile | Ser | Val | Ser | Met | Pro | Ser | Ile | Glu | Val | Gly | Thr | Ile | Gly |
| 945 | | | | | 950 | | | | | 955 | | | | | 960 |

3000

| GGT | GGT | ACT | GTT | CTA | GAA | CCA | CAA | GGT | GCC | ATG | TTG | GAC | TTA | TTA | GGT |
|---|---|---|---|---|---|---|---|---|---|---|---|---|---|---|---|
| Gly | Gly | Thr | Val | Leu | Glu | Pro | Gln | Gly | Ala | Met | Leu | Asp | Leu | Leu | Gly |
| | | 965 | | | | | 970 | | | | | 975 | | | |

3048

| GTA | AGA | GGC | CCG | CAT | GCT | ACC | GCT | CCT | GGT | ACC | AAC | GCA | CGT | CAA | TTA |
|---|---|---|---|---|---|---|---|---|---|---|---|---|---|---|---|
| Val | Arg | Gly | Pro | His | Ala | Thr | Ala | Pro | Gly | Thr | Asn | Ala | Arg | Gln | Leu |
| | 980 | | | | | 985 | | | | | 990 | | | | |

```
GCA AGA ATA GTT GCC TGT GCC GTC TTG GCA GGT GAA TTA TCC TTA TGT     3144
Ala Arg Ile Val Ala Cys Ala Val Leu Ala Gly Glu Leu Ser Leu Cys
            995                 1000                1005

GCT GCC CTA GCA GCC GGC CAT TTG GTT CAA AGT CAT ATG ACC CAC AAC     3192
Ala Ala Leu Ala Ala Gly His Leu Val Gln Ser His Met Thr His Asn
        1010                1015                1020

AGG AAA CCT GCT GAA CCA ACA AAA CCT AAC AAC AAT TTG GAC GCC ACT GAT 3240
Arg Lys Pro Ala Glu Pro Thr Lys Pro Asn Asn Asn Leu Asp Ala Thr Asp
    1025                1030                1035                1040

ATA AAT CGT TTG AAA GAT GGG TCC GTC ACC TGC ATT AAA TCC                 3282
Ile Asn Arg Leu Lys Asp Gly Ser Val Thr Cys Ile Lys Ser
        1045                1050

TAAACTTAGT CATACGTCAT TGGTATTCTC TTGAAAAAGA AGCACAACAG CACCATGTGT   3342

TACGTAAAAT ATTTACTT                                                 3360
```

Figure 3J

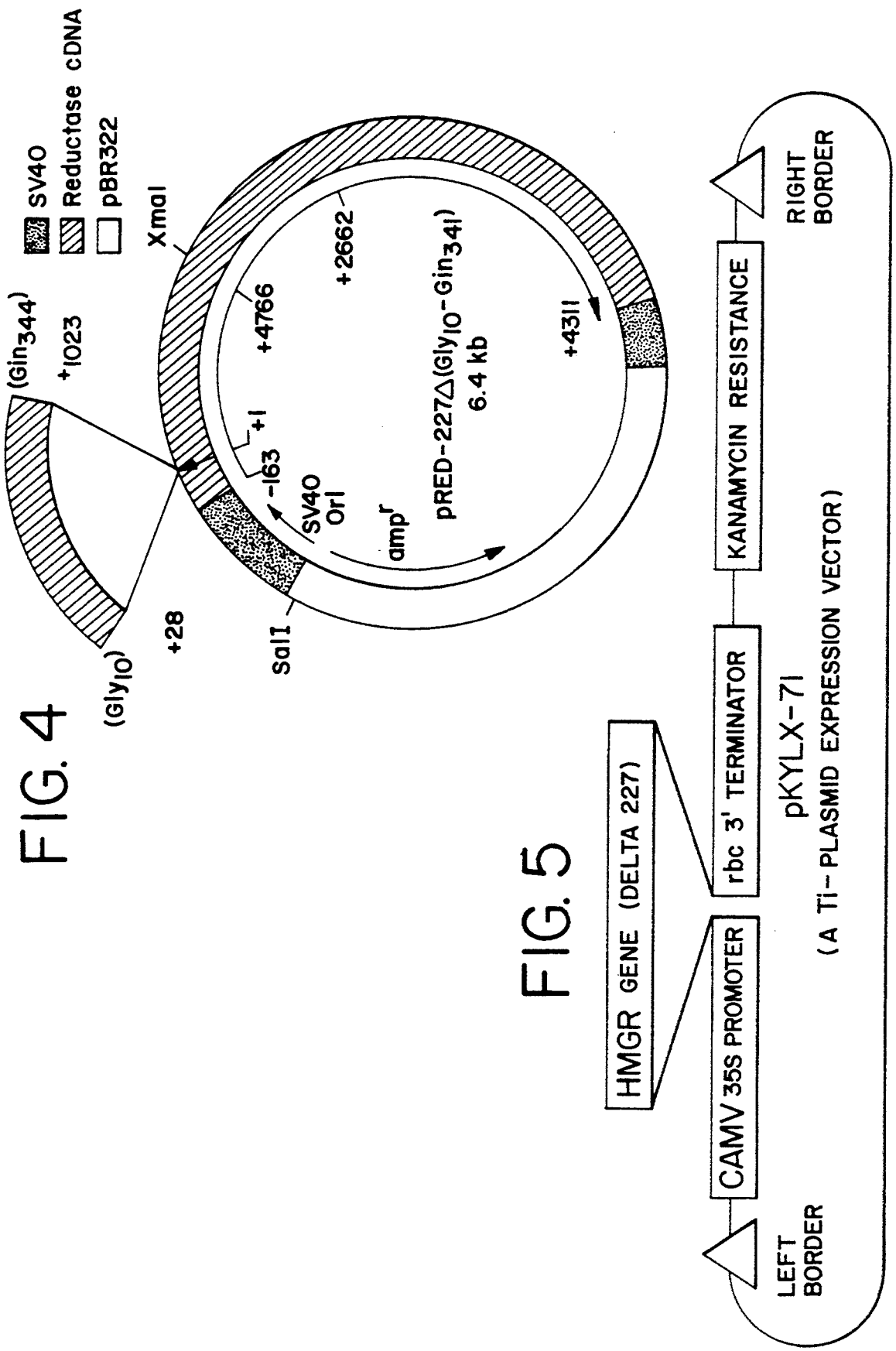

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4768 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 164..2827

( x i ) SEQUENCE DESCRIPTION: SEQ ID NO:1:

```
TGTATGTCTT  GTCTTTCTCC  TAAGGGGCGT  AGGCTCATTG  ATAACTCATG  TCCTCACCTT        60

GCACTCCTTT  TGGAATTATT  TGGTTTGAGT  GAAGAAGACC  GGACCTTCGA  GGTTCGCAAC       120

TTAAACAATA  GACTTGTGAG  GATCCAGGGA  CCGAGTGGCT  ACA ATG TTG TCA CGA          175
                                                 Met Leu Ser Arg
                                                  1

CTT TTC CGT ATG CAT GGC CTC TTT GTG GCC TCC CAT CCC TGG GAA GTT            223
Leu Phe Arg Met His Gly Leu Phe Val Ala Ser His Pro Trp Glu Val
 5              10                  15                  20

ATT GTG GGG ACG GTG ACA CTT ACC ATC TGT ATG ATG TCC ATG AAC ATG            271
Ile Val Gly Thr Val Thr Leu Thr Ile Cys Met Met Ser Met Asn Met
             25                  30                  35
```

| | | | | | | | | | | | | | | | | |
|---|---|---|---|---|---|---|---|---|---|---|---|---|---|---|---|---|
| TTC | ACT | GGC | AAC | AAC | AAG | ATC | TGT | GGT | TGG | AAT | TAC | GAG | TGC | CCA | AAA | 319 |
| Phe | Thr | Gly | Asn | Asn | Lys | Ile | Cys | Gly | Trp | Asn | Tyr | Glu | Cys | Pro | Lys | |
| | | | 40 | | | | | 45 | | | | | 50 | | | |
| TTT | GAG | GAG | GAT | GTA | TTG | AGC | AGT | GAC | ATC | ATC | ATC | CTC | ACC | ATA | ACA | 367 |
| Phe | Glu | Glu | Asp | Val | Leu | Ser | Ser | Asp | Ile | Ile | Ile | Leu | Thr | Ile | Thr | |
| | | 55 | | | | | 60 | | | | | 65 | | | | |
| CGG | TGC | ATC | GCC | ATC | CTG | TAC | ATT | TAC | TTC | CAG | TTC | CAG | AAC | TTA | CGT | 415 |
| Arg | Cys | Ile | Ala | Ile | Leu | Tyr | Ile | Tyr | Phe | Gln | Phe | Gln | Asn | Leu | Arg | |
| | | 70 | | | | 75 | | | | | 80 | | | | | |
| CAG | CTT | GGG | TCG | AAG | TAT | ATT | TTA | GGT | ATT | GCT | GGC | CTG | TTC | ACA | ATT | 463 |
| Gln | Leu | Gly | Ser | Lys | Tyr | Ile | Leu | Gly | Ile | Ala | Gly | Leu | Phe | Thr | Ile | |
| 85 | | | | | 90 | | | | | 95 | | | | | 100 | |
| TTC | TCA | AGT | TTT | GTC | TTT | AGT | ACA | GTC | GTC | ATT | CAC | TTC | TTA | GAC | AAA | 511 |
| Phe | Ser | Ser | Phe | Val | Phe | Ser | Thr | Val | Val | Ile | His | Phe | Leu | Asp | Lys | |
| | | | | 105 | | | | | 110 | | | | | 115 | | |
| GAA | CTG | ACG | GGC | TTA | AAT | GAA | GCT | TTG | CCC | TTT | TTC | CTG | CTT | TTG | ATT | 559 |
| Glu | Leu | Thr | Gly | Leu | Asn | Glu | Ala | Leu | Pro | Phe | Phe | Leu | Leu | Leu | Ile | |
| | | | 120 | | | | | 125 | | | | | 130 | | | |
| GAC | CTT | TCT | AGA | GCG | AGT | GCA | CTA | GCA | AAG | TTT | GCC | CTA | AGT | TCA | AAC | 607 |
| Asp | Leu | Ser | Arg | Ala | Ser | Ala | Leu | Ala | Lys | Phe | Ala | Leu | Ser | Ser | Asn | |
| | | 135 | | | | | 140 | | | | | 145 | | | | |
| TCT | CAG | GAT | GAA | GTA | AGG | GAA | AAT | ATA | GCT | CGC | GGA | ATG | GCA | ATT | CTG | 655 |
| Ser | Gln | Asp | Glu | Val | Arg | Glu | Asn | Ile | Ala | Arg | Gly | Met | Ala | Ile | Leu | |
| | 150 | | | | | 155 | | | | | 160 | | | | | |
| GGC | CCC | ACA | TTC | ACC | CTT | GAT | GCT | CTT | GTG | GAA | TGT | CTT | GTA | ATT | GGA | 703 |
| Gly | Pro | Thr | Phe | Thr | Leu | Asp | Ala | Leu | Val | Glu | Cys | Leu | Val | Ile | Gly | |
| 165 | | | | | 170 | | | | | 175 | | | | | 180 | |
| GTT | GGC | ACC | ATG | TCA | GGG | GTG | CGT | CAG | CTT | GAA | ATC | ATG | TGC | TGC | TTT | 751 |
| Val | Gly | Thr | Met | Ser | Gly | Val | Arg | Gln | Leu | Glu | Ile | Met | Cys | Cys | Phe | |
| | | | | 185 | | | | | 190 | | | | | 195 | | |
| GGC | TGC | ATG | TCT | GTG | CTT | GCC | AAC | TAC | TTC | GTG | TTC | ATG | ACA | TTT | TTC | 799 |
| Gly | Cys | Met | Ser | Val | Leu | Ala | Asn | Tyr | Phe | Val | Phe | Met | Thr | Phe | Phe | |
| | | | 200 | | | | | 205 | | | | | 210 | | | |
| CCA | GCG | TGT | GTG | TCC | CTG | GTC | CTT | GAG | CTT | TCT | CGG | GAA | AGT | CGA | GAG | 847 |
| Pro | Ala | Cys | Val | Ser | Leu | Val | Leu | Glu | Leu | Ser | Arg | Glu | Ser | Arg | Glu | |
| | | 215 | | | | | 220 | | | | | 225 | | | | |
| GGT | CGT | CCA | ATT | TGG | CAG | CTT | AGC | CAT | TTT | GCC | CGA | GTT | TTG | GAA | GAA | 895 |
| Gly | Arg | Pro | Ile | Trp | Gln | Leu | Ser | His | Phe | Ala | Arg | Val | Leu | Glu | Glu | |
| | 230 | | | | | 235 | | | | | 240 | | | | | |
| GAA | GAG | AAT | AAA | CCA | AAC | CCT | GTA | ACC | CAA | AGG | GTC | AAG | ATG | ATT | ATG | 943 |
| Glu | Glu | Asn | Lys | Pro | Asn | Pro | Val | Thr | Gln | Arg | Val | Lys | Met | Ile | Met | |
| 245 | | | | | 250 | | | | | 255 | | | | | 260 | |
| TCT | TTA | GGT | TTG | GTT | CTT | GTT | CAT | GCT | CAC | AGT | CGA | TGG | ATA | GCT | GAT | 991 |
| Ser | Leu | Gly | Leu | Val | Leu | Val | His | Ala | His | Ser | Arg | Trp | Ile | Ala | Asp | |
| | | | | 265 | | | | | 270 | | | | | 275 | | |
| CCT | TCC | CCT | CAG | AAT | AGC | ACA | ACA | GAA | CAT | TCT | AAA | GTC | TCC | TTG | GGA | 1039 |
| Pro | Ser | Pro | Gln | Asn | Ser | Thr | Thr | Glu | His | Ser | Lys | Val | Ser | Leu | Gly | |
| | | | 280 | | | | | 285 | | | | | 290 | | | |
| CTG | GAT | GAA | GAT | GTG | TCC | AAG | AGA | ATT | GAA | CCA | AGT | GTT | TCT | CTC | TGG | 1087 |
| Leu | Asp | Glu | Asp | Val | Ser | Lys | Arg | Ile | Glu | Pro | Ser | Val | Ser | Leu | Trp | |
| | | 295 | | | | | 300 | | | | | 305 | | | | |
| CAG | TTT | TAT | CTC | TCC | AAG | ATG | ATC | AGC | ATG | GAC | ATT | GAA | CAA | GTG | GTT | 1135 |
| Gln | Phe | Tyr | Leu | Ser | Lys | Met | Ile | Ser | Met | Asp | Ile | Glu | Gln | Val | Val | |
| | 310 | | | | | 315 | | | | | 320 | | | | | |
| ACC | CTG | AGC | TTA | GCT | TTT | CTG | TTG | GCT | GTC | AAG | TAC | ATT | TTC | TTT | GAA | 1183 |
| Thr | Leu | Ser | Leu | Ala | Phe | Leu | Leu | Ala | Val | Lys | Tyr | Ile | Phe | Phe | Glu | |
| 325 | | | | | 330 | | | | | 335 | | | | | 340 | |
| CAA | GCA | GAG | ACA | GAG | TCC | ACA | CTG | TCT | TTA | AAA | AAT | CCT | ATC | ACG | TCT | 1231 |
| Gln | Ala | Glu | Thr | Glu | Ser | Thr | Leu | Ser | Leu | Lys | Asn | Pro | Ile | Thr | Ser | |
| | | | | 345 | | | | | 350 | | | | | 355 | | |
| CCT | GTC | GTG | ACC | CCA | AAG | AAA | GCT | CCA | GAC | AAC | TGT | TGT | AGA | CGG | GAG | 1279 |
| Pro | Val | Val | Thr | Pro | Lys | Lys | Ala | Pro | Asp | Asn | Cys | Cys | Arg | Arg | Glu | |

-continued

|  |  |  |  |  |  | 360 |  |  |  | 365 |  |  |  | 370 |  |  |  |
|---|---|---|---|---|---|---|---|---|---|---|---|---|---|---|---|---|---|
| CCT | CTG | CTT | GTG | AGA | AGG | AGC | GAG | AAG | CTT | TCA | TCG | GTT | GAG | GAG | GAG |  | 1327 |
| Pro | Leu | Leu<br>375 | Val | Arg | Arg | Ser | Glu<br>380 | Lys | Leu | Ser | Ser | Val<br>385 | Glu | Glu | Glu |  |  |
| CCT | GGG | GTG | AGC | CAA | GAT | AGA | AAA | GTT | GAG | GTT | ATA | AAA | CCA | TTA | GTG |  | 1375 |
| Pro | Gly<br>390 | Val | Ser | Gln | Asp | Arg<br>395 | Lys | Val | Glu | Val | Ile<br>400 | Lys | Pro | Leu | Val |  |  |
| GTG | GAA | ACT | GAG | AGT | GCA | AGC | AGA | GCT | ACA | TTT | GTG | CTT | GGC | GCC | TCT |  | 1423 |
| Val<br>405 | Glu | Thr | Glu | Ser | Ala<br>410 | Ser | Arg | Ala | Thr | Phe<br>415 | Val | Leu | Gly | Ala | Ser<br>420 |  |  |
| GGG | ACC | AGC | CCT | CCA | GTG | GCA | GCG | AGG | ACA | CAG | GAG | CTT | GAA | ATT | GAA |  | 1471 |
| Gly | Thr | Ser | Pro | Pro<br>425 | Val | Ala | Ala | Arg | Thr<br>430 | Gln | Glu | Leu | Glu | Ile<br>435 | Glu |  |  |
| CTC | CCC | AGT | GAG | CCT | CGG | CCT | AAT | GAA | GAA | TGT | CTG | CAG | ATA | CTG | GAG |  | 1519 |
| Leu | Pro | Ser | Glu<br>440 | Pro | Arg | Pro | Asn | Glu<br>445 | Glu | Cys | Leu | Gln | Ile<br>450 | Leu | Glu |  |  |
| AGT | GCC | GAG | AAA | GGT | GCA | AAG | TTC | CTT | AGC | GAT | GCA | GAG | ATC | ATC | CAG |  | 1567 |
| Ser | Ala | Glu | Lys<br>455 | Gly | Ala | Lys | Phe | Leu<br>460 | Ser | Asp | Ala | Glu | Ile<br>465 | Ile | Gln |  |  |
| TTG | GTC | AAT | GCC | AAG | CAC | ATC | CCA | GCC | TAC | AAA | TTG | GAA | ACC | TTA | ATG |  | 1615 |
| Leu | Val | Asn<br>470 | Ala | Lys | His | Ile | Pro<br>475 | Ala | Tyr | Lys | Leu | Glu<br>480 | Thr | Leu | Met |  |  |
| GAA | ACT | CAT | GAA | CGT | GGT | GTA | TCT | ATT | CGC | CGG | CAG | CTC | CTC | TCC | ACA |  | 1663 |
| Glu<br>485 | Thr | His | Glu | Arg | Gly<br>490 | Val | Ser | Ile | Arg | Arg<br>495 | Gln | Leu | Leu | Ser | Thr<br>500 |  |  |
| AAG | CTT | CCA | GAG | CCT | TCT | TCT | CTG | CAG | TAC | CTG | CCT | TAC | AGA | GAT | TAT |  | 1711 |
| Lys | Leu | Pro | Glu | Pro<br>505 | Ser | Ser | Leu | Gln | Tyr<br>510 | Leu | Pro | Tyr | Arg | Asp<br>515 | Tyr |  |  |
| AAT | TAT | TCC | CTG | GTG | ATG | GGA | GCT | TGC | TGT | GAG | AAT | GTG | ATC | GGA | TAT |  | 1759 |
| Asn | Tyr | Ser | Leu<br>520 | Val | Met | Gly | Ala | Cys<br>525 | Cys | Glu | Asn | Val | Ile<br>530 | Gly | Tyr |  |  |
| ATG | CCC | ATC | CCT | GTC | GGA | GTA | GCA | GGG | CCT | CTG | TGC | CTG | GAT | GGT | AAA |  | 1807 |
| Met | Pro | Ile<br>535 | Pro | Val | Gly | Val | Ala<br>540 | Gly | Pro | Leu | Cys | Leu<br>545 | Asp | Gly | Lys |  |  |
| GAG | TAC | CAG | GTT | CCA | ATG | GCA | ACA | ACG | GAA | GGC | TGT | CTG | GTG | GCC | AGC |  | 1855 |
| Glu | Tyr<br>550 | Gln | Val | Pro | Met | Ala<br>555 | Thr | Thr | Glu | Gly | Cys<br>560 | Leu | Val | Ala | Ser |  |  |
| ACC | AAC | AGA | GGC | TGC | AGG | GCA | ATA | GGT | CTT | GGT | GGA | GGT | GCC | AGC | AGC |  | 1903 |
| Thr<br>565 | Asn | Arg | Gly | Cys | Arg<br>570 | Ala | Ile | Gly | Leu | Gly<br>575 | Gly | Gly | Ala | Ser | Ser<br>580 |  |  |
| CGG | GTC | CTT | GCA | GAT | GGG | ATG | ACC | CGG | GGC | CCA | GTG | GTG | CGT | CTT | CCT |  | 1951 |
| Arg | Val | Leu | Ala | Asp<br>585 | Gly | Met | Thr | Arg | Gly<br>590 | Pro | Val | Val | Arg | Leu<br>595 | Pro |  |  |
| CGT | GCT | TGT | GAT | TCT | GCA | GAA | GTG | AAG | GCC | TGG | CTT | GAA | ACA | CCC | GAA |  | 1999 |
| Arg | Ala | Cys | Asp<br>600 | Ser | Ala | Glu | Val | Lys<br>605 | Ala | Trp | Leu | Glu | Thr<br>610 | Pro | Glu |  |  |
| GGG | TTT | GCG | GTG | ATA | AAG | GAC | GCC | TTT | GAT | AGC | ACT | AGC | AGA | TTT | GCA |  | 2047 |
| Gly | Phe | Ala<br>615 | Val | Ile | Lys | Asp | Ala<br>620 | Phe | Asp | Ser | Thr | Ser<br>625 | Arg | Phe | Ala |  |  |
| CGT | CTA | CAG | AAG | CTT | CAT | GTG | ACC | ATG | GCA | GGG | CGC | AAC | CTG | TAC | ATC |  | 2095 |
| Arg | Leu | Gln<br>630 | Lys | Leu | His | Val | Thr<br>635 | Met | Ala | Gly | Arg | Asn<br>640 | Leu | Tyr | Ile |  |  |
| CGT | TTC | CAG | TCC | AAG | ACA | GGG | GAT | GCC | ATG | GGG | ATG | AAC | ATG | ATT | TCC |  | 2143 |
| Arg | Phe | Gln | Ser | Lys<br>650 | Thr | Gly | Asp | Ala | Met<br>655 | Gly | Met | Asn | Met | Ile<br>660 | Ser |  |  |
| Arg<br>645 |  |  |  |  |  |  |  |  |  |  |  |  |  |  |  |  |  |
| AAG | GGC | ACT | GAG | AAA | GCA | CTT | CTG | AAG | CTT | CAG | GAG | TTC | TTT | CCT | GAA |  | 2191 |
| Lys | Gly | Thr | Glu | Lys<br>665 | Ala | Leu | Leu | Lys | Leu<br>670 | Gln | Glu | Phe | Phe | Pro<br>675 | Glu |  |  |
| ATG | CAG | ATT | CTG | GCA | GTT | AGT | GGT | AAC | TAC | TGC | ACT | GAC | AAG | AAA | CCT |  | 2239 |
| Met | Gln | Ile | Leu<br>680 | Ala | Val | Ser | Gly<br>685 | Asn | Tyr | Cys | Thr | Asp<br>690 | Lys | Lys | Pro |  |  |

| | | | | | | | | | | | | | | | | |
|---|---|---|---|---|---|---|---|---|---|---|---|---|---|---|---|---|
| GCC | GCC | ATA | AAC | TGG | ATC | GAG | GGA | AGA | GGA | AAG | ACA | GTT | GTG | TGT | GAA | 2287 |
| Ala | Ala | Ile | Asn | Trp | Ile | Glu | Gly | Arg | Gly | Lys | Thr | Val | Val | Cys | Glu | |
| | | 695 | | | | 700 | | | | | 705 | | | | | |
| GCT | GTT | ATT | CCA | GCC | AAG | GTG | GTG | AGA | GAA | GTA | TTA | AAG | ACA | ACT | ACG | 2335 |
| Ala | Val | Ile | Pro | Ala | Lys | Val | Val | Arg | Glu | Val | Leu | Lys | Thr | Thr | Thr | |
| | | 710 | | | | 715 | | | | | 720 | | | | | |
| GAA | GCT | ATG | ATT | GAC | GTA | AAC | ATT | AAC | AAG | AAT | CTT | GTG | GGT | TCT | GCC | 2383 |
| Glu | Ala | Met | Ile | Asp | Val | Asn | Ile | Asn | Lys | Asn | Leu | Val | Gly | Ser | Ala | |
| 725 | | | | | 730 | | | | | 735 | | | | | 740 | |
| ATG | GCT | GGG | AGC | ATA | GGA | GGC | TAC | AAT | GCC | CAT | GCA | GCA | AAC | ATC | GTC | 2431 |
| Met | Ala | Gly | Ser | Ile | Gly | Gly | Tyr | Asn | Ala | His | Ala | Ala | Asn | Ile | Val | |
| | | | | 745 | | | | | 750 | | | | | 755 | | |
| ACT | GCT | ATC | TAC | ATT | GCA | TGT | GGC | CAG | GAT | GCA | GCA | CAG | AAT | GTG | GGG | 2479 |
| Thr | Ala | Ile | Tyr | Ile | Ala | Cys | Gly | Gln | Asp | Ala | Ala | Gln | Asn | Val | Gly | |
| | | | 760 | | | | | 765 | | | | | 770 | | | |
| AGT | TCA | AAC | TGT | ATT | ACT | TTA | ATG | GAA | GCA | AGT | GGT | CCC | ACG | AAT | GAA | 2527 |
| Ser | Ser | Asn | Cys | Ile | Thr | Leu | Met | Glu | Ala | Ser | Gly | Pro | Thr | Asn | Glu | |
| | | 775 | | | | | 780 | | | | | 785 | | | | |
| GAC | TTG | TAT | ATC | AGC | TGC | ACC | ATG | CCA | TCT | ATA | GAG | ATA | GGA | ACT | GTG | 2575 |
| Asp | Leu | Tyr | Ile | Ser | Cys | Thr | Met | Pro | Ser | Ile | Glu | Ile | Gly | Thr | Val | |
| | 790 | | | | | 795 | | | | | 800 | | | | | |
| GGT | GGT | GGG | ACC | AAC | CTC | CTA | CCA | CAG | CAG | GCC | TGT | CTG | CAG | ATG | CTA | 2623 |
| Gly | Gly | Gly | Thr | Asn | Leu | Leu | Pro | Gln | Gln | Ala | Cys | Leu | Gln | Met | Leu | |
| 805 | | | | | 810 | | | | | 815 | | | | | 820 | |
| GGT | GTT | CAA | GGA | GCG | TGC | AAA | GAC | AAT | CCT | GGA | GAA | AAT | GCA | CGG | CAA | 2671 |
| Gly | Val | Gln | Gly | Ala | Cys | Lys | Asp | Asn | Pro | Gly | Glu | Asn | Ala | Arg | Gln | |
| | | | | 825 | | | | | 830 | | | | | 835 | | |
| CTT | GCC | CGA | ATT | GTG | TGT | GGT | ACT | GTA | ATG | GCT | GGG | GAG | TTG | TCC | TTG | 2719 |
| Leu | Ala | Arg | Ile | Val | Cys | Gly | Thr | Val | Met | Ala | Gly | Glu | Leu | Ser | Leu | |
| | | | 840 | | | | | 845 | | | | | 850 | | | |
| ATG | GCA | GCA | TTG | GCA | GCA | GGA | CAT | CTT | GTT | AGA | AGT | CAC | ATG | GTT | CAT | 2767 |
| Met | Ala | Ala | Leu | Ala | Ala | Gly | His | Leu | Val | Arg | Ser | His | Met | Val | His | |
| | | 855 | | | | | 860 | | | | | 865 | | | | |
| AAC | AGA | TCG | AAG | ATA | AAT | TTA | CAA | GAT | CTG | CAA | GGA | ACG | TGC | ACC | AAG | 2815 |
| Asn | Arg | Ser | Lys | Ile | Asn | Leu | Gln | Asp | Leu | Gln | Gly | Thr | Cys | Thr | Lys | |
| | 870 | | | | | 875 | | | | | 880 | | | | | |
| AAG | TCA | GCT | TGAGCAGCCT | | GACAGTATTG | | AACTGAAACA | | CGGGCATTGG | | | | | | | 2864 |
| Lys | Ser | Ala | | | | | | | | | | | | | | |
| 885 | | | | | | | | | | | | | | | | |

| | |
|---|---|
| GTTCTCAAGG ACTAACATGA AATCTGTGAA TTAAAAATCT CAATGCAGTG TCTTGTGGAA | 2924 |
| GATGAATGAA CGTGATCAGT GAGACGCCTG CTTGGTTTCT GGCTCTTTCA GAGACGTCTG | 2984 |
| AGGTCCTTTG CTCGGAGACT CCTCAGATCT GGAACAGTG TGGTCCTTCC CATGCTGTAT | 3044 |
| TCTGAAAAGA TCTCATATGG ATGTTGTGCT CTGAGCACCA CAGATGTGAT CTGCAGCTCG | 3104 |
| TTTCTGAAAT GATGGAGTTC ATGGTGATCA GTGTGAGACT GGCCTCTCCC AGCAGGTTAA | 3164 |
| AAATGGAGTT TTAAATTATA CTGTAGCTGA CAGTACTTCT GATTTTATAT TTATTTAGTC | 3224 |
| TGAGTTGTAG AACTTTGCAA TCTAAGTTTA TTTTTTGTAA CCTAATAATT CATTTGGTGC | 3284 |
| TGGTCTATTG ATTTTTGGGG GTAAACAATA TTATTCTTCA GAAGGGGACC TACTTCTTCA | 3344 |
| TGGGAAGAAT TACTTTTATT CTCAAACTAC AGAACAATGT GCTAAGCAGT GCTAAATTGT | 3404 |
| TCTCATGAAG AAAACAGTCA CTGCATTTAT CTCTGTAGGC CTTTTTTCAG AGAGGCCTTG | 3464 |
| TCTAGATTTT TGCCAGCTAG GCTACTGCAT GTCTTAGTGT CAGGCCTTAG GAAAGTGCCA | 3524 |
| CGCTCTGCAC TAAAGATATC AGAGCTCTTG GTGTTACTTA GACAAGAGTA TGAGCAAGTC | 3584 |
| GGACCTCTCA GAGTGTGGGA ACACAGTTTT GAAAGAAAAA CCATTTCTCT AAGCCAATTT | 3644 |
| TCTTTAAAGA CATTTTAACT TATTTAGCTG AGTTCTAGAT TTTCGGGTA AACTATCAAA | 3704 |
| TCTGTATATG TTGTAATAAA GTGTCTTATG CTAGGAGTTT ATTCAAAGTG TTTAAGTAAT | 3764 |

| | | | | | |
|---|---|---|---|---|---|
| AAAAGGACTC | AAATTTACAC | TGATAAAATA | CTCTAGCTTG | GGCCAGAGAA | GACAGTGCTC | 3824
| ATTAGCGTTG | TCCAGGAAAC | CCTGCTTGCT | TGCCAAGCCT | AATGAAGGGA | AAGTCAGCTT | 3884
| TCAGAGCCAA | TGATGGAGGC | CACATGAATG | GCCCTGGAGC | TGTGTGCCTT | GTTCTGTGGC | 3944
| CAGGAGCTTG | GTGACTGAAT | CATTTACGGG | CTCCTTTGAT | GGACCCATAA | AGCTCTTAG | 4004
| CTTCCTCAGG | GGGTCAGCAG | AGTTGTTGAA | TCTTAATTTT | TTTTTAATG | TACCAGTTTT | 4064
| GTATAAATAA | TAATAAAGAG | CTCCTTATTT | TGTATTCTAT | CTAATGCTTC | GAGTTCAGTC | 4124
| TTGGGAAGCT | GACATCTCAT | GTAGAAGATG | GACTCTGAAA | GACATTCCAA | GAGTGCAGCG | 4184
| GCATCATGGG | AGCCTCTTAG | TGATTGTGTG | TCAGTATTAT | TGTGGAAGAT | TGACTTTGCT | 4244
| TTTGTATGTG | AAGTTTCAGA | TTGCTCCTCT | TGTGACTTTT | TAGCCAGTAA | CATTTTATTT | 4304
| ACCTGAGCTT | GTCATGGAAG | TGGCAGTGAA | AAGTATTGAG | TATTCATGCT | GGTGACTGTA | 4364
| ACCAATGTCA | TCTTGCTAAA | AACTCATGTT | TTGTACAATT | ACTAAATTGT | ATACATTTG | 4424
| TTATAGAATA | CTTTTTCCAG | TTGAGTAAAT | TATGAAAGGA | AGTTAACATT | AACAGGTGTA | 4484
| AGCGGTGGCT | TTTTTAAAAT | GAAGGATTAA | CCCTAAGCCC | GAGACCCAGA | AGCTAGCAAA | 4544
| GTCTGGCAGA | GTGGTAAACT | GTCCTGCTGG | GGCCATCCAA | TCATCTCTCT | CCATTACACT | 4604
| TTCTAACTTT | GCAGCATTGG | TGCTGGCCAG | TGTATTGTTT | CATTGATCTT | CCTTACGCTT | 4664
| AGAGGGTTTG | ATTGGTTCAG | ATCTATAATC | TCAGCCACAT | TGTCTTGGTA | TCAGCTGGAG | 4724
| AGAGTTAAGA | GGAAGGGAAA | ATAAAGTTCA | GATAGCCAAA | ACAC | | 4768

(2) INFORMATION FOR SEQ ID NO:2:

(i) SEQUENCE CHARACTERISTICS:
  (A) LENGTH: 887 amino acids
  (B) TYPE: amino acid
  (D) TOPOLOGY: linear (ii) MOLECULE TYPE: protein (xi) SEQUENCE DESCRIPTION: SEQ ID NO:2:

```
Met Leu Ser Arg Leu Phe Arg Met His Gly Leu Phe Val Ala Ser His
 1               5                  10                  15

Pro Trp Glu Val Ile Val Gly Thr Val Thr Leu Thr Ile Cys Met Met
                20                  25                  30

Ser Met Asn Met Phe Thr Gly Asn Asn Lys Ile Cys Gly Trp Asn Tyr
            35                  40                  45

Glu Cys Pro Lys Phe Glu Glu Asp Val Leu Ser Ser Asp Ile Ile Ile
    50                  55                  60

Leu Thr Ile Thr Arg Cys Ile Ala Ile Leu Tyr Ile Tyr Phe Gln Phe
 65                  70                  75                  80

Gln Asn Leu Arg Gln Leu Gly Ser Lys Tyr Ile Leu Gly Ile Ala Gly
                85                  90                  95

Leu Phe Thr Ile Phe Ser Ser Phe Val Phe Ser Thr Val Val Ile His
            100                 105                 110

Phe Leu Asp Lys Glu Leu Thr Gly Leu Asn Glu Ala Leu Pro Phe Phe
        115                 120                 125

Leu Leu Leu Ile Asp Leu Ser Arg Ala Ser Ala Leu Ala Lys Phe Ala
    130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
            180                 185                 190
```

-continued

| | | | | | | | | | | | | | | |
|---|---|---|---|---|---|---|---|---|---|---|---|---|---|---|
| Met | Cys | Cys 195 | Phe | Gly | Cys | Met 200 | Ser | Val | Leu | Ala | Asn 205 | Tyr | Phe | Phe |
| Met | Thr 210 | Phe | Phe | Pro | Ala | Cys 215 | Val | Ser | Leu | Val | Leu 220 | Glu | Leu | Ser | Arg |
| Glu 225 | Ser | Arg | Glu | Gly | Arg 230 | Pro | Ile | Trp | Gln | Leu 235 | Ser | His | Phe | Ala | Arg 240 |
| Val | Leu | Glu | Glu | Glu 245 | Glu | Asn | Lys | Pro | Asn 250 | Pro | Val | Thr | Gln | Arg 255 | Val |
| Lys | Met | Ile | Met 260 | Ser | Leu | Gly | Leu | Val 265 | Leu | Val | His | Ala | His 270 | Ser | Arg |
| Trp | Ile | Ala 275 | Asp | Pro | Ser | Pro | Gln 280 | Asn | Ser | Thr | Thr | Glu 285 | His | Ser | Lys |
| Val | Ser 290 | Leu | Gly | Leu | Asp | Glu 295 | Asp | Val | Ser | Lys | Arg 300 | Ile | Glu | Pro | Ser |
| Val 305 | Ser | Leu | Trp | Gln | Phe 310 | Tyr | Leu | Ser | Lys | Met 315 | Ile | Ser | Met | Asp | Ile 320 |
| Glu | Gln | Val | Val | Thr 325 | Leu | Ser | Leu | Ala | Phe 330 | Leu | Leu | Ala | Val | Lys 335 | Tyr |
| Ile | Phe | Phe | Glu 340 | Gln | Ala | Glu | Thr | Glu 345 | Ser | Thr | Leu | Ser | Leu 350 | Lys | Asn |
| Pro | Ile | Thr 355 | Ser | Pro | Val | Val | Thr 360 | Pro | Lys | Lys | Ala | Pro 365 | Asp | Asn | Cys |
| Cys | Arg 370 | Arg | Glu | Pro | Leu | Leu 375 | Val | Arg | Arg | Ser | Glu 380 | Lys | Leu | Ser | Ser |
| Val 385 | Glu | Glu | Glu | Pro | Gly 390 | Val | Ser | Gln | Asp | Arg 395 | Lys | Val | Glu | Val | Ile 400 |
| Lys | Pro | Leu | Val | Val 405 | Glu | Thr | Glu | Ser | Ala 410 | Ser | Arg | Ala | Thr | Phe 415 | Val |
| Leu | Gly | Ala | Ser | Gly 420 | Thr | Ser | Pro | Pro | Val 425 | Ala | Ala | Arg | Thr 430 | Gln | Glu |
| Leu | Glu | Ile 435 | Glu | Leu | Pro | Ser | Glu 440 | Pro | Arg | Pro | Asn | Glu 445 | Glu | Cys | Leu |
| Gln | Ile 450 | Leu | Glu | Ser | Ala | Glu 455 | Lys | Gly | Ala | Lys | Phe 460 | Leu | Ser | Asp | Ala |
| Glu 465 | Ile | Ile | Gln | Leu | Val 470 | Asn | Ala | Lys | His | Ile 475 | Pro | Ala | Tyr | Lys | Leu 480 |
| Glu | Thr | Leu | Met | Glu 485 | Thr | His | Glu | Arg | Gly 490 | Val | Ser | Ile | Arg | Arg 495 | Gln |
| Leu | Leu | Ser | Thr 500 | Lys | Leu | Pro | Glu | Pro 505 | Ser | Ser | Leu | Gln | Tyr 510 | Leu | Pro |
| Tyr | Arg | Asp 515 | Tyr | Asn | Tyr | Ser | Leu 520 | Val | Met | Gly | Ala | Cys 525 | Cys | Glu | Asn |
| Val | Ile 530 | Gly | Tyr | Met | Pro | Ile 535 | Pro | Val | Gly | Val | Ala 540 | Gly | Pro | Leu | Cys |
| Leu 545 | Asp | Gly | Lys | Glu | Tyr 550 | Gln | Val | Pro | Met | Ala 555 | Thr | Thr | Glu | Gly | Cys 560 |
| Leu | Val | Ala | Ser | Thr 565 | Asn | Arg | Gly | Cys | Arg 570 | Ala | Ile | Gly | Leu | Gly 575 | Gly |
| Gly | Ala | Ser | Ser 580 | Arg | Val | Leu | Ala | Asp 585 | Gly | Met | Thr | Arg | Gly 590 | Pro | Val |
| Val | Arg | Leu 595 | Pro | Arg | Ala | Cys | Asp 600 | Ser | Ala | Glu | Val | Lys 605 | Ala | Trp | Leu |
| Glu | Thr 610 | Pro | Glu | Gly | Phe | Ala 615 | Val | Ile | Lys | Asp | Ala 620 | Phe | Asp | Ser | Thr |
| Ser | Arg | Phe | Ala | Arg | Leu | Gln | Lys | Leu | His | Val | Thr | Met | Ala | Gly | Arg |

```
                625              630              635              640
        Asn  Leu  Tyr  Ile  Arg  Phe  Gln  Ser  Lys  Thr  Gly  Asp  Ala  Met  Gly  Met
                           645                   650                   655
        Asn  Met  Ile  Ser  Lys  Gly  Thr  Glu  Lys  Ala  Leu  Leu  Lys  Leu  Gln  Glu
                           660                   665                   670
        Phe  Phe  Pro  Glu  Met  Gln  Ile  Leu  Ala  Val  Ser  Gly  Asn  Tyr  Cys  Thr
                       675                   680                   685
        Asp  Lys  Lys  Pro  Ala  Ala  Ile  Asn  Trp  Ile  Glu  Gly  Arg  Gly  Lys  Thr
                  690                   695                   700
        Val  Val  Cys  Glu  Ala  Val  Ile  Pro  Ala  Lys  Val  Val  Arg  Glu  Val  Leu
        705                   710                   715                   720
        Lys  Thr  Thr  Thr  Glu  Ala  Met  Ile  Asp  Val  Asn  Ile  Asn  Lys  Asn  Leu
                            725                   730                   735
        Val  Gly  Ser  Ala  Met  Ala  Gly  Ser  Ile  Gly  Gly  Tyr  Asn  Ala  His  Ala
                       740                   745                   750
        Ala  Asn  Ile  Val  Thr  Ala  Ile  Tyr  Ile  Ala  Cys  Gly  Gln  Asp  Ala  Ala
                       755                   760                   765
        Gln  Asn  Val  Gly  Ser  Ser  Asn  Cys  Ile  Thr  Leu  Met  Glu  Ala  Ser  Gly
                 770                   775                   780
        Pro  Thr  Asn  Glu  Asp  Leu  Tyr  Ile  Ser  Cys  Thr  Met  Pro  Ser  Ile  Glu
        785                   790                   795                   800
        Ile  Gly  Thr  Val  Gly  Gly  Gly  Thr  Asn  Leu  Leu  Pro  Gln  Gln  Ala  Cys
                            805                   810                   815
        Leu  Gln  Met  Leu  Gly  Val  Gln  Gly  Ala  Cys  Lys  Asp  Asn  Pro  Gly  Glu
                       820                   825                   830
        Asn  Ala  Arg  Gln  Leu  Ala  Arg  Ile  Val  Cys  Gly  Thr  Val  Met  Ala  Gly
                  835                   840                   845
        Glu  Leu  Ser  Leu  Met  Ala  Ala  Leu  Ala  Ala  Gly  His  Leu  Val  Arg  Ser
        850                   855                   860
        His  Met  Val  His  Asn  Arg  Ser  Lys  Ile  Asn  Leu  Gln  Asp  Leu  Gln  Gly
        865                   870                   875                   880
        Thr  Cys  Thr  Lys  Lys  Ser  Ala
                            885
```

( 2 ) INFORMATION FOR SEQ ID NO:3:

( i ) SEQUENCE CHARACTERISTICS:
        ( A ) LENGTH: 3360 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 121..3282

( x i ) SEQUENCE DESCRIPTION: SEQ ID NO:3:

```
TTTATTAACT  TATTTTTTC  TTCTTTCTAC  CCAATTCTAG  TCAGGAAAAG  ACTAAGGGCT      60

GGAACATAGT  GTATCATTGT  CTAATTGTTG  ATACAAAGTA  GATAAATACA  TAAAACAAGC    120

ATG  CCG  CCG  CTA  TTC  AAG  GGA  CTG  AAA  CAG  ATG  GCA  AAG  CCA  ATT  GCC    168
Met  Pro  Pro  Leu  Phe  Lys  Gly  Leu  Lys  Gln  Met  Ala  Lys  Pro  Ile  Ala
 1                  5                   10                  15

TAT  GTT  TCA  AGA  TTT  TCG  GCG  AAA  CGA  CCA  ATT  CAT  ATA  ATA  CTT  TTT    216
Tyr  Val  Ser  Arg  Phe  Ser  Ala  Lys  Arg  Pro  Ile  His  Ile  Ile  Leu  Phe
                20                  25                  30

TCT  CTA  ATC  ATA  TCC  GCA  TTC  GCT  TAT  CTA  TCC  GTC  ATT  CAG  TAT  TAC    264
Ser  Leu  Ile  Ile  Ser  Ala  Phe  Ala  Tyr  Leu  Ser  Val  Ile  Gln  Tyr  Tyr
           35                  40                  45
```

| | | | | | | | | | | | | | | | | |
|---|---|---|---|---|---|---|---|---|---|---|---|---|---|---|---|---|
| TTC | AAT | GGT | TGG | CAA | CTA | GAT | TCA | AAT | AGT | GTT | TTT | GAA | ACT | GCT | CCA | 312 |
| Phe | Asn 50 | Gly | Trp | Gln | Leu | Asp 55 | Ser | Asn | Ser | Val | Phe 60 | Glu | Thr | Ala | Pro | |
| AAT | AAA | GAC | TCC | AAC | ACT | CTA | TTT | CAA | GAA | TGT | TCC | CAT | TAC | TAC | AGA | 360 |
| Asn 65 | Lys | Asp | Ser | Asn | Thr 70 | Leu | Phe | Gln | Glu | Cys 75 | Ser | His | Tyr | Tyr | Arg 80 | |
| GAT | TCC | TCT | CTA | GAT | GGT | TGG | GTA | TCA | ATC | ACC | GCG | CAT | GAA | GCT | AGT | 408 |
| Asp | Ser | Ser | Leu | Asp 85 | Gly | Trp | Val | Ser | Ile 90 | Thr | Ala | His | Glu | Ala 95 | Ser | |
| GAG | TTA | CCA | GCC | CCA | CAC | CAT | TAC | TAT | CTA | TTA | AAC | CTG | AAC | TTC | AAT | 456 |
| Glu | Leu | Pro | Ala 100 | Pro | His | His | Tyr | Tyr 105 | Leu | Leu | Asn | Leu 110 | Asn | Phe | Asn | |
| AGT | CCT | AAT | GAA | ACT | GAC | TCC | ATT | CCA | GAA | CTA | GCT | AAC | ACG | GTT | TTT | 504 |
| Ser | Pro | Asn 115 | Glu | Thr | Asp | Ser | Ile 120 | Pro | Glu | Leu | Ala | Asn 125 | Thr | Val | Phe | |
| GAG | AAA | GAT | AAT | ACA | AAA | TAT | ATT | CTG | CAA | GAA | GAT | CTC | AGT | GTT | TCC | 552 |
| Glu | Lys 130 | Asp | Asn | Thr | Lys | Tyr 135 | Ile | Leu | Gln | Glu | Asp 140 | Leu | Ser | Val | Ser | |
| AAA | GAA | ATT | TCT | TCT | ACT | GAT | GGA | ACG | AAA | TGG | AGG | TTA | AGA | AGT | GAC | 600 |
| Lys 145 | Glu | Ile | Ser | Ser | Thr 150 | Asp | Gly | Thr | Lys | Trp 155 | Arg | Leu | Arg | Ser | Asp 160 | |
| AGA | AAA | AGT | CTT | TTC | GAC | GTA | AAG | ACG | TTA | GCA | TAT | TCT | CTC | TAC | GAT | 648 |
| Arg | Lys | Ser | Leu | Phe 165 | Asp | Val | Lys | Thr | Leu 170 | Ala | Tyr | Ser | Leu | Tyr 175 | Asp | |
| GTA | TTT | TCA | GAA | AAT | GTA | ACC | CAA | GCA | GAC | CCG | TTT | GAC | GTC | CTT | ATT | 696 |
| Val | Phe | Ser | Glu 180 | Asn | Val | Thr | Gln | Ala 185 | Asp | Pro | Phe | Asp | Val 190 | Leu | Ile | |
| ATG | GTT | ACT | GCC | TAC | CTA | ATG | ATG | TTC | TAC | ACC | ATA | TTC | GGC | CTC | TTC | 744 |
| Met | Val | Thr | Ala 195 | Tyr | Leu | Met | Met | Phe 200 | Tyr | Thr | Ile | Phe | Gly 205 | Leu | Phe | |
| AAT | GAC | ATG | AGG | AAG | ACC | GGG | TCA | AAT | TTT | TGG | TTG | AGC | GCC | TCT | ACA | 792 |
| Asn | Asp | Met 210 | Arg | Lys | Thr | Gly | Ser 215 | Asn | Phe | Trp | Leu | Ser 220 | Ala | Ser | Thr | |
| GTG | GTC | AAT | TCT | GCA | TCA | TCA | CTT | TTC | TTA | GCA | TTG | TAT | GTC | ACC | CAA | 840 |
| Val 225 | Val | Asn | Ser | Ala | Ser 230 | Ser | Leu | Phe | Leu | Ala 235 | Leu | Tyr | Val | Thr | Gln 240 | |
| TGT | ATT | CTA | GGC | AAA | GAA | GTT | TCC | GCA | TTA | ACT | CTT | TTT | GAA | GGT | TTG | 888 |
| Cys | Ile | Leu | Gly | Lys 245 | Glu | Val | Ser | Ala | Leu 250 | Thr | Leu | Phe | Glu | Gly 255 | Leu | |
| CCT | TTC | ATT | GTA | GTT | GTT | GGT | TTC | AAG | CAC | AAA | ATC | AAG | ATT | GCC | | 936 |
| Pro | Phe | Ile | Val 260 | Val | Val | Val | Gly | Phe 265 | Lys | His | Lys | Ile | Lys 270 | Ile | Ala | |
| CAG | TAT | GCC | CTG | GAG | AAA | TTT | GAA | AGA | GTC | GGT | TTA | TCT | AAA | AGG | ATT | 984 |
| Gln | Tyr | Ala | Leu 275 | Glu | Lys | Phe | Glu | Arg 280 | Val | Gly | Leu | Ser | Lys 285 | Arg | Ile | |
| ACT | ACC | GAT | GAA | ATC | GTT | TTT | GAA | TCC | GTG | AGC | GAA | GAG | GGT | GGT | CGT | 1032 |
| Thr | Thr | Asp 290 | Glu | Ile | Val | Phe | Glu 295 | Ser | Val | Ser | Glu | Glu 300 | Gly | Gly | Arg | |
| TTG | ATT | CAA | GAC | CAT | TTG | CTT | TGT | ATT | TTT | GCC | TTT | ATC | GGA | TGC | TCT | 1080 |
| Leu 305 | Ile | Gln | Asp | His | Leu 310 | Leu | Cys | Ile | Phe | Ala 315 | Phe | Ile | Gly | Cys | Ser 320 | |
| ATG | TAT | GCT | CAC | CAA | TTG | AAG | ACT | TTG | ACA | AAC | TTC | TGC | ATA | TTA | TCA | 1128 |
| Met | Tyr | Ala | His | Gln 325 | Leu | Lys | Thr | Leu | Thr 330 | Asn | Phe | Cys | Ile | Leu 335 | Ser | |
| GCA | TTT | ATC | CTA | ATT | TTT | GAA | TTG | ATT | TTA | ACT | CCT | ACA | TTT | TAT | TCT | 1176 |
| Ala | Phe | Ile | Leu 340 | Ile | Phe | Glu | Leu | Ile 345 | Leu | Thr | Pro | Thr | Phe 350 | Tyr | Ser | |
| GCT | ATC | TTA | GCG | CTT | AGA | CTG | GAA | ATG | AAT | GTT | ATC | CAC | AGA | TCT | ACT | 1224 |
| Ala | Ile | Leu 355 | Ala | Leu | Arg | Leu | Glu 360 | Met | Asn | Val | Ile | His 365 | Arg | Ser | Thr | |
| ATT | ATC | AAG | CAA | ACA | TTA | GAA | GAA | GAC | GGT | GTT | GTT | CCA | TCT | ACA | GCA | 1272 |

|  |  |  |  |  |  |  |  |  |  |  |  |  |  |  |  |
|---|---|---|---|---|---|---|---|---|---|---|---|---|---|---|---|
| Ile | Ile<br>370 | Lys | Gln | Thr | Leu<br>375 | Glu | Glu | Asp | Gly | Val<br>380 | Val | Pro | Ser | Thr | Ala |

| AGA | ATC | ATT | TCT | AAA | GCA | GAA | AAG | AAA | TCC | GTA | TCT | TCT | TTC | TTA | AAT | 1320 |
|---|---|---|---|---|---|---|---|---|---|---|---|---|---|---|---|---|
| Arg<br>385 | Ile | Ile | Ser | Lys | Ala<br>390 | Glu | Lys | Lys | Ser | Val<br>395 | Ser | Ser | Phe | Leu | Asn<br>400 | |

| CTC | AGT | GTG | GTT | GTC | ATT | ATC | ATG | AAA | CTC | TCT | GTC | ATA | CTG | TTG | TTT | 1368 |
|---|---|---|---|---|---|---|---|---|---|---|---|---|---|---|---|---|
| Leu | Ser | Val | Val | Val<br>405 | Ile | Ile | Met | Lys | Leu<br>410 | Ser | Val | Ile | Leu | Leu<br>415 | Phe | |

| GTT | TTC | ATC | AAC | TTT | TAT | AAC | TTT | GGT | GCA | AAT | TGG | GTC | AAT | GAT | GCC | 1416 |
|---|---|---|---|---|---|---|---|---|---|---|---|---|---|---|---|---|
| Val | Phe | Ile | Asn<br>420 | Phe | Tyr | Asn | Phe | Gly<br>425 | Ala | Asn | Trp | Val | Asn<br>430 | Asp | Ala | |

| TTC | AAT | TCA | TTG | TAC | TTC | GAT | AAG | GAA | CGT | GTT | TCT | CTA | CCA | GAT | TTT | 1464 |
|---|---|---|---|---|---|---|---|---|---|---|---|---|---|---|---|---|
| Phe | Asn | Ser<br>435 | Leu | Tyr | Phe | Asp | Lys<br>440 | Glu | Arg | Val | Ser | Leu<br>445 | Pro | Asp | Phe | |

| ATT | ACC | TCG | AAT | GCC | TCT | GAA | AAC | TTT | AAA | GAG | CAA | GCT | ATT | GTT | AGT | 1512 |
|---|---|---|---|---|---|---|---|---|---|---|---|---|---|---|---|---|
| Ile | Thr | Ser<br>450 | Asn | Ala | Ser | Glu | Asn<br>455 | Phe | Lys | Glu | Gln | Ala<br>460 | Ile | Val | Ser | |

| GTC | ACC | CCA | TTA | TTA | TAT | TAC | AAA | CCC | ATT | AAG | TCC | TAC | CAA | CGC | ATT | 1560 |
|---|---|---|---|---|---|---|---|---|---|---|---|---|---|---|---|---|
| Val<br>465 | Thr | Pro | Leu | Leu<br>470 | Tyr | Tyr | Lys | Pro | Ile<br>475 | Lys | Ser | Tyr | Gln | Arg<br>480 | Ile | |

| GAG | GAT | ATG | GTT | CTT | CTA | TTG | CTT | CGT | AAT | GTC | AGT | GTT | GCC | ATT | CGT | 1608 |
|---|---|---|---|---|---|---|---|---|---|---|---|---|---|---|---|---|
| Glu | Asp | Met | Val | Leu<br>485 | Leu | Leu | Leu | Arg | Asn<br>490 | Val | Ser | Val | Ala | Ile<br>495 | Arg | |

| GAT | AGG | TTC | GTC | AGT | AAA | TTA | GTT | CTT | TCC | GCC | TTA | GTA | TGC | AGT | GCT | 1656 |
|---|---|---|---|---|---|---|---|---|---|---|---|---|---|---|---|---|
| Asp | Arg | Phe | Val<br>500 | Ser | Lys | Leu | Val | Leu<br>505 | Ser | Ala | Leu | Val | Cys<br>510 | Ser | Ala | |

| GTC | ATC | AAT | GTG | TAT | TTA | TTG | AAT | GCT | GCT | AGA | ATT | CAT | ACC | AGT | TAT | 1704 |
|---|---|---|---|---|---|---|---|---|---|---|---|---|---|---|---|---|
| Val | Ile | Asn<br>515 | Val | Tyr | Leu | Leu | Asn<br>520 | Ala | Ala | Arg | Ile | His<br>525 | Thr | Ser | Tyr | |

| ACT | GCA | GAC | CAA | TTG | GTG | AAA | ACT | GAA | GTC | ACC | AAG | AAG | TCT | TTT | ACT | 1752 |
|---|---|---|---|---|---|---|---|---|---|---|---|---|---|---|---|---|
| Thr | Ala<br>530 | Asp | Gln | Leu | Val | Lys<br>535 | Thr | Glu | Val | Thr | Lys<br>540 | Lys | Ser | Phe | Thr | |

| GCT | CCT | GTA | CAA | AAG | GCT | TCT | ACA | CCA | GTT | TTA | ACC | AAT | AAA | ACA | GTC | 1800 |
|---|---|---|---|---|---|---|---|---|---|---|---|---|---|---|---|---|
| Ala | Pro<br>545 | Val | Gln | Lys | Ala<br>550 | Ser | Thr | Pro | Val | Leu<br>555 | Thr | Asn | Lys | Thr | Val<br>560 | |

| ATT | TCT | GGA | TCG | AAA | GTC | AAA | AGT | TTA | TCA | TCT | GCG | CAA | TCG | AGC | TCA | 1848 |
|---|---|---|---|---|---|---|---|---|---|---|---|---|---|---|---|---|
| Ile | Ser | Gly | Ser | Lys<br>565 | Val | Lys | Ser | Leu | Ser<br>570 | Ser | Ala | Gln | Ser | Ser<br>575 | Ser | |

| TCA | GGA | CCT | TCA | TCA | TCT | AGT | GAG | GAA | GAT | GAT | TCC | CGC | GAT | ATT | GAA | 1896 |
|---|---|---|---|---|---|---|---|---|---|---|---|---|---|---|---|---|
| Ser | Gly | Pro | Ser<br>580 | Ser | Ser | Ser | Glu | Glu<br>585 | Asp | Asp | Ser | Arg | Asp<br>590 | Ile | Glu | |

| AGC | TTG | GAT | AAG | AAA | ATA | CGT | CCT | TTA | GAA | GAA | TTA | GAA | GCA | TTA | TTA | 1944 |
|---|---|---|---|---|---|---|---|---|---|---|---|---|---|---|---|---|
| Ser | Leu | Asp<br>595 | Lys | Lys | Ile | Arg | Pro<br>600 | Leu | Glu | Glu | Leu | Glu<br>605 | Ala | Leu | Leu | |

| AGT | AGT | GGA | AAT | ACA | AAA | CAA | TTG | AAG | AAC | AAA | GAG | GTC | GCT | GCC | TTG | 1992 |
|---|---|---|---|---|---|---|---|---|---|---|---|---|---|---|---|---|
| Ser | Ser<br>610 | Gly | Asn | Thr | Lys | Gln<br>615 | Leu | Lys | Asn | Lys | Glu<br>620 | Val | Ala | Ala | Leu | |

| GTT | ATT | CAC | GGT | AAG | TTA | CCT | TTG | TAC | GCT | TTG | GAG | AAA | AAA | TTA | GGT | 2040 |
|---|---|---|---|---|---|---|---|---|---|---|---|---|---|---|---|---|
| Val<br>625 | Ile | His | Gly | Lys | Leu<br>630 | Pro | Leu | Tyr | Ala | Leu<br>635 | Glu | Lys | Lys | Leu | Gly<br>640 | |

| GAT | ACT | ACG | AGA | GCG | GTT | GCG | GTA | CGT | AGG | AAG | GCT | CTT | TCA | ATT | TTG | 2088 |
|---|---|---|---|---|---|---|---|---|---|---|---|---|---|---|---|---|
| Asp | Thr | Thr | Arg | Ala<br>645 | Val | Ala | Val | Arg | Arg<br>650 | Lys | Ala | Leu | Ser | Ile<br>655 | Leu | |

| GCA | GAA | GCT | CCT | GTA | TTA | GCA | TCT | GAT | CGT | TTA | CCA | TAT | AAA | AAT | TAT | 2136 |
|---|---|---|---|---|---|---|---|---|---|---|---|---|---|---|---|---|
| Ala | Glu | Ala | Pro<br>660 | Val | Leu | Ala | Ser | Asp<br>665 | Arg | Leu | Pro | Tyr | Lys<br>670 | Asn | Tyr | |

| GAC | TAC | GAC | CGC | GTA | TTT | GGC | GCT | TGT | TGT | GAA | AAT | GTT | ATA | GGT | TAC | 2184 |
|---|---|---|---|---|---|---|---|---|---|---|---|---|---|---|---|---|
| Asp | Tyr | Asp | Arg<br>675 | Val | Phe | Gly | Ala | Cys<br>680 | Cys | Glu | Asn | Val | Ile<br>685 | Gly | Tyr | |

| ATG | CCT | TTG | CCC | GTT | GGT | GTT | ATA | GGC | CCC | TTG | GTT | ATC | GAT | GGT | ACA | 2232 |
|---|---|---|---|---|---|---|---|---|---|---|---|---|---|---|---|---|
| Met | Pro | Leu<br>690 | Pro | Val | Gly | Val | Ile<br>695 | Gly | Pro | Leu | Val | Ile<br>700 | Asp | Gly | Thr | |

| | | | | | | | | | | | | | | | | |
|---|---|---|---|---|---|---|---|---|---|---|---|---|---|---|---|---|
| TCT | TAT | CAT | ATA | CCA | ATG | GCA | ACT | ACA | GAG | GGT | TGT | TTG | GTA | GCT | TCT | 2280 |
| Ser 705 | Tyr | His | Ile | Pro | Met 710 | Ala | Thr | Thr | Glu 715 | Gly | Cys | Leu | Val | Ala | Ser 720 | |
| GCC | ATG | CGT | GGC | TGT | AAG | GCA | ATC | AAT | GCT | GGC | GGT | GGT | GCA | ACA | ACT | 2328 |
| Ala | Met | Arg | Gly | Cys 725 | Lys | Ala | Ile | Asn | Ala 730 | Gly | Gly | Gly | Ala | Thr 735 | Thr | |
| GTT | TTA | ACT | AAG | GAT | GGT | ATG | ACA | AGA | GGC | CCA | GTA | GTC | CGT | TTC | CCA | 2376 |
| Val | Leu | Thr | Lys 740 | Asp | Gly | Met | Thr | Arg 745 | Gly | Pro | Val | Val | Arg 750 | Phe | Pro | |
| ACT | TTG | AAA | AGA | TCT | GGT | GCC | TGT | AAG | ATA | TGG | TTA | GAC | TCA | GAA | GAG | 2424 |
| Thr | Leu | Lys 755 | Arg | Ser | Gly | Ala | Cys 760 | Lys | Ile | Trp | Leu | Asp 765 | Ser | Glu | Glu | |
| GGA | CAA | AAC | GCA | ATT | AAA | AAA | GCT | TTT | AAC | TCT | ACA | TCA | AGA | TTT | GCA | 2472 |
| Gly | Gln | Asn 770 | Ala | Ile | Lys | Lys 775 | Ala | Phe | Asn | Ser | Thr 780 | Ser | Arg | Phe | Ala | |
| CGT | CTG | CAA | CAT | ATT | CAA | ACT | TGT | CTA | GCA | GGA | GAT | TTA | CTC | TTC | ATG | 2520 |
| Arg 785 | Leu | Gln | His | Ile 790 | Gln | Thr | Cys | Leu | Ala 795 | Gly | Asp | Leu | Leu | Phe | Met 800 | |
| AGA | TTT | AGA | ACA | ACT | ACT | GGT | GAC | GCA | ATG | GGT | ATG | AAT | ATG | ATT | TCT | 2568 |
| Arg | Phe | Arg | Thr | Thr 805 | Thr | Gly | Asp | Ala | Met 810 | Gly | Met | Asn | Met | Ile 815 | Ser | |
| AAA | GGT | GTC | GAA | TAC | TCA | TTA | AAG | CAA | ATG | GTA | GAA | GAG | TAT | GGC | TGG | 2616 |
| Lys | Gly | Val | Glu 820 | Tyr | Ser | Leu | Lys | Gln 825 | Met | Val | Glu | Glu | Tyr 830 | Gly | Trp | |
| GAA | GAT | ATG | GAG | GTT | GTC | TCC | GTT | TCT | GGT | AAC | TAC | TGT | ACC | GAC | AAA | 2664 |
| Glu | Asp | Met 835 | Glu | Val | Val | Ser | Val 840 | Ser | Gly | Asn | Tyr | Cys 845 | Thr | Asp | Lys | |
| AAA | CCA | GCT | GCC | ATC | AAC | TGG | ATC | GAA | GGT | CGT | GGT | AAG | AGT | GTC | GTC | 2712 |
| Lys | Pro 850 | Ala | Ala | Ile | Asn | Trp 855 | Ile | Glu | Gly | Arg | Gly 860 | Lys | Ser | Val | Val | |
| GCA | GAA | GCT | ACT | ATT | CCT | GGT | GAT | GTT | GTC | AGA | AAA | GTG | TTA | AAA | AGT | 2760 |
| Ala 865 | Glu | Ala | Thr | Ile | Pro 870 | Gly | Asp | Val | Val | Arg 875 | Lys | Val | Leu | Lys | Ser 880 | |
| GAT | GTT | TCC | GCA | TTG | GTT | GAG | TTG | AAC | ATT | GCT | AAG | AAT | TTG | GTT | GGA | 2808 |
| Asp | Val | Ser | Ala | Leu 885 | Val | Glu | Leu | Asn | Ile 890 | Ala | Lys | Asn | Leu | Val 895 | Gly | |
| TCT | GCA | ATG | GCT | GGG | TCT | GTT | GGT | GGA | TTT | AAC | GCA | CAT | GCA | GCT | AAT | 2856 |
| Ser | Ala | Met | Ala 900 | Gly | Ser | Val | Gly | Gly 905 | Phe | Asn | Ala | His | Ala 910 | Ala | Asn | |
| TTA | GTG | ACA | GCT | GTT | TTC | TTG | GCA | TTA | GGA | CAA | GAT | CCT | GCA | CAA | AAT | 2904 |
| Leu | Val | Thr 915 | Ala | Val | Phe | Leu | Ala 920 | Leu | Gly | Gln | Asp | Pro 925 | Ala | Gln | Asn | |
| GTT | GAA | AGT | TCC | AAC | TGT | ATA | ACA | TTG | ATG | AAA | GAA | GTG | GAC | GGT | GAT | 2952 |
| Val | Glu | Ser | Ser 930 | Asn | Cys | Ile | Thr | Leu 935 | Met | Lys | Glu | Val | Asp 940 | Gly | Asp | |
| TTG | AGA | ATT | TCC | GTA | TCC | ATG | CCA | TCC | ATC | GAA | GTA | GGT | ACC | ATC | GGT | 3000 |
| Leu 945 | Arg | Ile | Ser | Val | Ser 950 | Met | Pro | Ser | Ile | Glu 955 | Val | Gly | Thr | Ile | Gly 960 | |
| GGT | GGT | ACT | GTT | CTA | GAA | CCA | CAA | GGT | GCC | ATG | TTG | GAC | TTA | TTA | GGT | 3048 |
| Gly | Gly | Thr | Val | Leu 965 | Glu | Pro | Gln | Gly | Ala 970 | Met | Leu | Asp | Leu | Leu 975 | Gly | |
| GTA | AGA | GGC | CCG | CAT | GCT | ACC | GCT | CCT | GGT | ACC | AAC | GCA | CGT | CAA | TTA | 3096 |
| Val | Arg | Gly | Pro 980 | His | Ala | Thr | Ala | Pro 985 | Gly | Thr | Asn | Ala | Arg 990 | Gln | Leu | |
| GCA | AGA | ATA | GTT | GCC | TGT | GCC | GTC | TTG | GCA | GGT | GAA | TTA | TCC | TTA | TGT | 3144 |
| Ala | Arg | Ile 995 | Val | Ala | Cys | Ala | Val 1000 | Leu | Ala | Gly | Glu | Leu 1005 | Ser | Leu | Cys | |
| GCT | GCC | CTA | GCA | GCC | GGC | CAT | TTG | GTT | CAA | AGT | CAT | ATG | ACC | CAC | AAC | 3192 |
| Ala | Ala | Leu 1010 | Ala | Ala | Gly | His | Leu 1015 | Val | Gln | Ser | His | Met 1020 | Thr | His | Asn | |
| AGG | AAA | CCT | GCT | GAA | CCA | ACA | AAA | CCT | AAC | AAT | TTG | GAC | GCC | ACT | GAT | 3240 |

| Arg | Lys | Pro | Ala | Glu | Pro | Thr | Lys | Pro | Asn | Asn | Leu | Asp | Ala | Thr | Asp |
| 1025 | | | | 1030 | | | | | 1035 | | | | | 1040 | |

```
ATA AAT CGT TTG AAA GAT GGG TCC GTC ACC TGC ATT AAA TCC         3282
Ile Asn Arg Leu Lys Asp Gly Ser Val Thr Cys Ile Lys Ser
        1045                    1050

TAAACTTAGT CATACGTCAT TGGTATTCTC TTGAAAAAGA AGCACAACAG CACCATGTGT  3342

TACGTAAAAT ATTTACTT                                                3360
```

( 2 ) INFORMATION FOR SEQ ID NO:4:

( i ) SEQUENCE CHARACTERISTICS:
        ( A ) LENGTH: 1054 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Pro | Pro | Leu | Phe | Lys | Gly | Leu | Lys | Gln | Met | Ala | Lys | Pro | Ile | Ala |
| 1 | | | | 5 | | | | | 10 | | | | | 15 | |

| Tyr | Val | Ser | Arg | Phe | Ser | Ala | Lys | Arg | Pro | Ile | His | Ile | Ile | Leu | Phe |
| | | | 20 | | | | | 25 | | | | | 30 | | |

| Ser | Leu | Ile | Ile | Ser | Ala | Phe | Ala | Tyr | Leu | Ser | Val | Ile | Gln | Tyr | Tyr |
| | | | 35 | | | | 40 | | | | | 45 | | | |

| Phe | Asn | Gly | Trp | Gln | Leu | Asp | Ser | Asn | Ser | Val | Phe | Glu | Thr | Ala | Pro |
| | 50 | | | | | 55 | | | | | 60 | | | | |

| Asn | Lys | Asp | Ser | Asn | Thr | Leu | Phe | Gln | Glu | Cys | Ser | His | Tyr | Tyr | Arg |
| 65 | | | | | 70 | | | | | 75 | | | | | 80 |

| Asp | Ser | Ser | Leu | Asp | Gly | Trp | Val | Ser | Ile | Thr | Ala | His | Glu | Ala | Ser |
| | | | | 85 | | | | | 90 | | | | | 95 | |

| Glu | Leu | Pro | Ala | Pro | His | His | Tyr | Tyr | Leu | Leu | Asn | Leu | Asn | Phe | Asn |
| | | | 100 | | | | | 105 | | | | | 110 | | |

| Ser | Pro | Asn | Glu | Thr | Asp | Ser | Ile | Pro | Glu | Leu | Ala | Asn | Thr | Val | Phe |
| | | | 115 | | | | 120 | | | | | 125 | | | |

| Glu | Lys | Asp | Asn | Thr | Lys | Tyr | Ile | Leu | Gln | Glu | Asp | Leu | Ser | Val | Ser |
| | | | 130 | | | | | 135 | | | | | 140 | | |

| Lys | Glu | Ile | Ser | Ser | Thr | Asp | Gly | Thr | Lys | Trp | Arg | Leu | Arg | Ser | Asp |
| 145 | | | | | 150 | | | | | 155 | | | | | 160 |

| Arg | Lys | Ser | Leu | Phe | Asp | Val | Lys | Thr | Leu | Ala | Tyr | Ser | Leu | Tyr | Asp |
| | | | | 165 | | | | | 170 | | | | | 175 | |

| Val | Phe | Ser | Glu | Asn | Val | Thr | Gln | Ala | Asp | Pro | Phe | Asp | Val | Leu | Ile |
| | | | 180 | | | | | 185 | | | | | 190 | | |

| Met | Val | Thr | Ala | Tyr | Leu | Met | Met | Phe | Tyr | Thr | Ile | Phe | Gly | Leu | Phe |
| | | | 195 | | | | 200 | | | | | 205 | | | |

| Asn | Asp | Met | Arg | Lys | Thr | Gly | Ser | Asn | Phe | Trp | Leu | Ser | Ala | Ser | Thr |
| | 210 | | | | | 215 | | | | | 220 | | | | |

| Val | Val | Asn | Ser | Ala | Ser | Ser | Leu | Phe | Leu | Ala | Leu | Tyr | Val | Thr | Gln |
| 225 | | | | | 230 | | | | | 235 | | | | | 240 |

| Cys | Ile | Leu | Gly | Lys | Glu | Val | Ser | Ala | Leu | Thr | Leu | Phe | Glu | Gly | Leu |
| | | | | 245 | | | | | 250 | | | | | 255 | |

| Pro | Phe | Ile | Val | Val | Val | Gly | Phe | Lys | His | Lys | Ile | Lys | Ile | Ala |
| | | | 260 | | | | | 265 | | | | | 270 | |

| Gln | Tyr | Ala | Leu | Glu | Lys | Phe | Glu | Arg | Val | Gly | Leu | Ser | Lys | Arg | Ile |
| | | | 275 | | | | | 280 | | | | | 285 | | |

| Thr | Thr | Asp | Glu | Ile | Val | Phe | Glu | Ser | Val | Ser | Glu | Glu | Gly | Gly | Arg |
| | | | 290 | | | | | 295 | | | | | 300 | | |

| Leu | Ile | Gln | Asp | His | Leu | Leu | Cys | Ile | Phe | Ala | Phe | Ile | Gly | Cys | Ser |
| 305 | | | | | 310 | | | | | 315 | | | | | 320 |

```
Met Tyr Ala His Gln Leu Lys Thr Leu Thr Asn Phe Cys Ile Leu Ser
            325                 330                 335
Ala Phe Ile Leu Ile Phe Glu Leu Ile Leu Thr Pro Thr Phe Tyr Ser
            340                 345                 350
Ala Ile Leu Ala Leu Arg Leu Glu Met Asn Val Ile His Arg Ser Thr
            355                 360                 365
Ile Ile Lys Gln Thr Leu Glu Glu Asp Gly Val Val Pro Ser Thr Ala
            370                 375                 380
Arg Ile Ile Ser Lys Ala Glu Lys Ser Val Ser Ser Phe Leu Asn
385                 390                 395                 400
Leu Ser Val Val Ile Ile Met Lys Leu Ser Val Ile Leu Leu Phe
                405                 410                 415
Val Phe Ile Asn Phe Tyr Asn Phe Gly Ala Asn Trp Val Asn Asp Ala
            420                 425                 430
Phe Asn Ser Leu Tyr Phe Asp Lys Glu Arg Val Ser Leu Pro Asp Phe
            435                 440                 445
Ile Thr Ser Asn Ala Ser Glu Asn Phe Lys Glu Gln Ala Ile Val Ser
    450                 455                 460
Val Thr Pro Leu Leu Tyr Tyr Lys Pro Ile Lys Ser Tyr Gln Arg Ile
465                 470                 475                 480
Glu Asp Met Val Leu Leu Leu Arg Asn Val Ser Val Ala Ile Arg
                485                 490                 495
Asp Arg Phe Val Ser Lys Leu Val Leu Ser Ala Leu Val Cys Ser Ala
            500                 505                 510
Val Ile Asn Val Tyr Leu Leu Asn Ala Ala Arg Ile His Thr Ser Tyr
        515                 520                 525
Thr Ala Asp Gln Leu Val Lys Thr Glu Val Thr Lys Lys Ser Phe Thr
    530                 535                 540
Ala Pro Val Gln Lys Ala Ser Thr Pro Val Leu Thr Asn Lys Thr Val
545                 550                 555                 560
Ile Ser Gly Ser Lys Val Lys Ser Leu Ser Ser Ala Gln Ser Ser Ser
            565                         570                 575
Ser Gly Pro Ser Ser Ser Ser Glu Glu Asp Asp Ser Arg Asp Ile Glu
            580                 585                 590
Ser Leu Asp Lys Lys Ile Arg Pro Leu Glu Glu Leu Glu Ala Leu Leu
        595                 600                 605
Ser Ser Gly Asn Thr Lys Gln Leu Lys Asn Lys Glu Val Ala Ala Leu
    610                 615                 620
Val Ile His Gly Lys Leu Pro Leu Tyr Ala Leu Glu Lys Lys Leu Gly
625                 630                 635                 640
Asp Thr Thr Arg Ala Val Ala Val Arg Arg Lys Ala Leu Ser Ile Leu
            645                 650                 655
Ala Glu Ala Pro Val Leu Ala Ser Asp Arg Leu Pro Tyr Lys Asn Tyr
            660                 665                 670
Asp Tyr Asp Arg Val Phe Gly Ala Cys Cys Glu Asn Val Ile Gly Tyr
    675                 680                 685
Met Pro Leu Pro Val Gly Val Ile Gly Pro Leu Val Ile Asp Gly Thr
    690                 695                 700
Ser Tyr His Ile Pro Met Ala Thr Thr Glu Gly Cys Leu Val Ala Ser
705                 710                 715                 720
Ala Met Arg Gly Cys Lys Ala Ile Asn Ala Gly Gly Gly Ala Thr Thr
            725                 730                 735
Val Leu Thr Lys Asp Gly Met Thr Arg Gly Pro Val Val Arg Phe Pro
            740                 745                 750
```

| | | | | | | | | | | | | | | |
|---|---|---|---|---|---|---|---|---|---|---|---|---|---|---|
| Thr | Leu | Lys 755 | Arg | Ser | Gly | Ala | Cys 760 | Lys | Ile | Trp | Leu 765 | Asp | Ser | Glu Glu |
| Gly | Gln 770 | Asn | Ala | Ile | Lys 775 | Lys | Ala | Phe | Asn | Ser 780 | Thr | Ser | Arg | Phe Ala |
| Arg 785 | Leu | Gln | His | Ile | Gln 790 | Thr | Cys | Leu | Ala | Gly 795 | Asp | Leu | Leu | Phe Met 800 |
| Arg | Phe | Arg | Thr | Thr 805 | Thr | Gly | Asp | Ala | Met 810 | Gly | Met | Asn | Met | Ile Ser 815 |
| Lys | Gly | Val | Glu 820 | Tyr | Ser | Leu | Lys | Gln 825 | Met | Val | Glu | Glu | Tyr 830 | Gly Trp |
| Glu | Asp | Met 835 | Glu | Val | Val | Ser 840 | Val | Ser | Gly | Asn | Tyr 845 | Cys | Thr | Asp Lys |
| Lys | Pro 850 | Ala | Ala | Ile | Asn | Trp 855 | Ile | Glu | Gly | Arg | Gly 860 | Lys | Ser | Val Val |
| Ala 865 | Glu | Ala | Thr | Ile | Pro 870 | Gly | Asp | Val | Val | Arg 875 | Lys | Val | Leu | Lys Ser 880 |
| Asp | Val | Ser | Ala | Leu 885 | Val | Glu | Leu | Asn | Ile 890 | Ala | Lys | Asn | Leu | Val Gly 895 |
| Ser | Ala | Met | Ala 900 | Gly | Ser | Val | Gly | Gly 905 | Phe | Asn | Ala | His | Ala 910 | Ala Asn |
| Leu | Val | Thr 915 | Ala | Val | Phe | Leu | Ala 920 | Leu | Gly | Gln | Asp | Pro 925 | Ala | Gln Asn |
| Val | Glu 930 | Ser | Ser | Asn | Cys | Ile 935 | Thr | Leu | Met | Lys | Glu 940 | Val | Asp | Gly Asp |
| Leu 945 | Arg | Ile | Ser | Val | Ser 950 | Met | Pro | Ser | Ile | Glu 955 | Val | Gly | Thr | Ile Gly 960 |
| Gly | Gly | Thr | Val | Leu 965 | Glu | Pro | Gln | Gly | Ala 970 | Met | Leu | Asp | Leu | Leu Gly 975 |
| Val | Arg | Gly | Pro 980 | His | Ala | Thr | Ala | Pro 985 | Gly | Thr | Asn | Ala | Arg 990 | Gln Leu |
| Ala | Arg | Ile 995 | Val | Ala | Cys | Ala | Val 1000 | Leu | Ala | Gly | Glu | Leu 1005 | Ser | Leu Cys |
| Ala | Ala 1010 | Leu | Ala | Ala | Gly | His 1015 | Leu | Val | Gln | Ser | His 1020 | Met | Thr | His Asn |
| Arg 1025 | Lys | Pro | Ala | Glu | Pro 1030 | Thr | Lys | Pro | Asn | Asn 1035 | Leu | Asp | Ala | Thr Asp 1040 |
| Ile | Asn | Arg | Leu | Lys 1045 | Asp | Gly | Ser | Val | Thr 1050 | Cys | Ile | Lys | Ser | |

(2) INFORMATION FOR SEQ ID NO:5:

(i) SEQUENCE CHARACTERISTICS:
(A) LENGTH: 3348 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 121..3255

(xi) SEQUENCE DESCRIPTION: SEQ ID NO:5:

```
GGAATATTTT GTACGAGCAA GTTATAGTAA GACACTTCAG TGAGAAATTA ATCTGACTTA      60

CTTTTACTTA ATTGTGTTCT TTCCAAATTA GTTCAACAAG GTTCCCACAT ACAACCTCAA     120

ATG TCA CTT CCC TTA AAA ACG ATA GTA CAT TTG GTA AAG CCC TTT GCT      168
Met Ser Leu Pro Leu Lys Thr Ile Val His Leu Val Lys Pro Phe Ala
  1               5                  10                  15
```

```
TGC ACT GCT AGG TTT AGT GCG AGA TAC CCA ATC CAC GTC ATT GTT GTT        216
Cys Thr Ala Arg Phe Ser Ala Arg Tyr Pro Ile His Val Ile Val Val
         20                  25                  30

GCT GTT TTA TTG AGT GCC GCT GCT TAT CTA TCC GTG ACA CAA TCT TAC        264
Ala Val Leu Leu Ser Ala Ala Ala Tyr Leu Ser Val Thr Gln Ser Tyr
             35                  40                  45

CTT AAC GAA TGG AAG CTG GAC TCT AAT CAG TAT TCT ACA TAC TTA AGC        312
Leu Asn Glu Trp Lys Leu Asp Ser Asn Gln Tyr Ser Thr Tyr Leu Ser
         50                  55                  60

ATA AAG CCG GAT GAG TTG TTT GAA AAA TGC ACA CAC TAC TAT AGG TCT        360
Ile Lys Pro Asp Glu Leu Phe Glu Lys Cys Thr His Tyr Tyr Arg Ser
 65          70                  75                  80

CCT GTG TCT GAT ACA TGG AAG TTA CTC AGC TCT AAA GAA GCC GCC GAT        408
Pro Val Ser Asp Thr Trp Lys Leu Leu Ser Ser Lys Glu Ala Ala Asp
                 85                  90                  95

ATT TAT ACC CCT TTT CAT TAT TAT TTG TCT ACC ATA AGT TTT CAA AGT        456
Ile Tyr Thr Pro Phe His Tyr Tyr Leu Ser Thr Ile Ser Phe Gln Ser
                100                 105                 110

AAG GAC AAT TCA ACG ACT TTG CCT TCC CTT GAT GAC GTT ATT TAC AGT        504
Lys Asp Asn Ser Thr Thr Leu Pro Ser Leu Asp Asp Val Ile Tyr Ser
             115                 120                 125

GTT GAC CAT ACC AGG TAC TTA TTA AGT GAA GAG CCA AAG ATA CCA ACT        552
Val Asp His Thr Arg Tyr Leu Leu Ser Glu Glu Pro Lys Ile Pro Thr
 130                 135                 140

GAA CTA GTG TCT GAA AAC GGA ACG AAA TGG AGA TTG AGA AAC AAC AGC        600
Glu Leu Val Ser Glu Asn Gly Thr Lys Trp Arg Leu Arg Asn Asn Ser
 145                 150                 155                 160

AAT TTT ATT TTG GAC CTG CAT AAT ATT TAC CGA AAT ATG GTG AAG CAA        648
Asn Phe Ile Leu Asp Leu His Asn Ile Tyr Arg Asn Met Val Lys Gln
                 165                 170                 175

TTT TCT AAC AAA ACG AGC GAA TTT GAT CAG TTC GAT TTG TTT ATC ATC        696
Phe Ser Asn Lys Thr Ser Glu Phe Asp Gln Phe Asp Leu Phe Ile Ile
             180                 185                 190

CTA GCT GCT TAC CTT ACT CTT TTT TAT ACT CTC TGT TGC CTG TTT AAT        744
Leu Ala Ala Tyr Leu Thr Leu Phe Tyr Thr Leu Cys Cys Leu Phe Asn
         195                 200                 205

GAC ATG AGG AAA ATC GGA TCA AAG TTT TGG TTA AGC TTT TCT GCT CTT        792
Asp Met Arg Lys Ile Gly Ser Lys Phe Trp Leu Ser Phe Ser Ala Leu
     210                 215                 220

TCA AAC TCT GCA TGC GCA TTA TAT TTA TCG CTG TAC ACA ACT CAC AGT        840
Ser Asn Ser Ala Cys Ala Leu Tyr Leu Ser Leu Tyr Thr Thr His Ser
 225                 230                 235                 240

TTA TTG AAG AAA CCG GCT TCC TTA TTA AGT TTG GTC ATT GGA CTA CCA        888
Leu Leu Lys Lys Pro Ala Ser Leu Leu Ser Leu Val Ile Gly Leu Pro
                 245                 250                 255

TTT ATC GTA GTA ATT ATT GGC TTT AAG CAT AAA GTT CGA CTT GCG GCA        936
Phe Ile Val Val Ile Ile Gly Phe Lys His Lys Val Arg Leu Ala Ala
             260                 265                 270

TTC TCG CTA CAA AAA TTC CAC AGA ATT AGT ATT GAC AAG AAA ATA ACG        984
Phe Ser Leu Gln Lys Phe His Arg Ile Ser Ile Asp Lys Lys Ile Thr
         275                 280                 285

GTA AGC AAC ATT ATT TAT GAG GCT ATG TTT CAA GAA GGT GCC TAC TTA       1032
Val Ser Asn Ile Ile Tyr Glu Ala Met Phe Gln Glu Gly Ala Tyr Leu
     290                 295                 300

ATC CGC GAC TAC TTA TTT TAT ATT AGC TCC TTC ATT GGA TGT GCT ATT       1080
Ile Arg Asp Tyr Leu Phe Tyr Ile Ser Ser Phe Ile Gly Cys Ala Ile
 305                 310                 315                 320

TAT GCT AGA CAT CTT CCC GGA TTG GTC AAT TTC TGT ATT TTG TCT ACA       1128
Tyr Ala Arg His Leu Pro Gly Leu Val Asn Phe Cys Ile Leu Ser Thr
                 325                 330                 335

TTT ATG CTA GTT TTC GAC TTG CTT TTG TCT GCT ACT TTT TAT TCT GCC       1176
Phe Met Leu Val Phe Asp Leu Leu Leu Ser Ala Thr Phe Tyr Ser Ala
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 340 |     |     |     |     | 345 |     |     |     |     |     | 350 |     |     |      |
| ATT | TTA | TCA | ATG | AAG | CTG | GAA | ATT | AAC | ATC | ATT | CAC | AGA | TCA | ACC | GTC | 1224 |
| Ile | Leu | Ser | Met | Lys | Leu | Glu | Ile | Asn | Ile | Ile | His | Arg | Ser | Thr | Val |      |
|     |     | 355 |     |     |     |     | 360 |     |     |     |     |     | 365 |     |     |      |
| ATC | AGA | CAG | ACT | TTG | GAA | GAG | GAC | GGA | GTT | GTC | CCA | ACT | ACA | GCA | GAT | 1272 |
| Ile | Arg | Gln | Thr | Leu | Glu | Glu | Asp | Gly | Val | Val | Pro | Thr | Thr | Ala | Asp |      |
|     | 370 |     |     |     |     | 375 |     |     |     |     | 380 |     |     |     |     |      |
| ATT | ATA | TAT | AAG | GAT | GAA | ACT | GCC | TCA | GAA | CCA | CAT | TTT | TTG | AGA | TCT | 1320 |
| Ile | Ile | Tyr | Lys | Asp | Glu | Thr | Ala | Ser | Glu | Pro | His | Phe | Leu | Arg | Ser |      |
| 385 |     |     |     |     | 390 |     |     |     |     | 395 |     |     |     |     | 400 |      |
| AAC | GTG | GCT | ATC | ATT | CTG | GGA | AAA | GCA | TCA | GTT | ATT | GGT | CTT | TTG | CTT | 1368 |
| Asn | Val | Ala | Ile | Ile | Leu | Gly | Lys | Ala | Ser | Val | Ile | Gly | Leu | Leu | Leu |      |
|     |     |     |     | 405 |     |     |     |     | 410 |     |     |     |     | 415 |     |      |
| CTG | ATC | AAC | CTT | TAT | GTT | TTC | ACA | GAT | AAG | TTA | AAT | GCT | ACA | ATA | CTA | 1416 |
| Leu | Ile | Asn | Leu | Tyr | Val | Phe | Thr | Asp | Lys | Leu | Asn | Ala | Thr | Ile | Leu |      |
|     |     |     | 420 |     |     |     |     | 425 |     |     |     |     | 430 |     |     |      |
| AAC | ACG | GTA | TAT | TTT | GAC | TCT | ACA | ATT | TAC | TCG | TTA | CCA | AAT | TTT | ATC | 1464 |
| Asn | Thr | Val | Tyr | Phe | Asp | Ser | Thr | Ile | Tyr | Ser | Leu | Pro | Asn | Phe | Ile |      |
|     |     | 435 |     |     |     |     | 440 |     |     |     |     | 445 |     |     |     |      |
| AAT | TAT | AAA | GAT | ATT | GGC | AAT | CTC | AGC | AAT | CAA | GTG | ATC | ATT | TCC | GTG | 1512 |
| Asn | Tyr | Lys | Asp | Ile | Gly | Asn | Leu | Ser | Asn | Gln | Val | Ile | Ile | Ser | Val |      |
|     | 450 |     |     |     |     | 455 |     |     |     |     | 460 |     |     |     |     |      |
| TTG | CCA | AAG | CAA | TAT | TAT | ACT | CCG | CTG | AAA | AAA | TAC | CAT | CAG | ATC | GAA | 1560 |
| Leu | Pro | Lys | Gln | Tyr | Tyr | Thr | Pro | Leu | Lys | Lys | Tyr | His | Gln | Ile | Glu |      |
| 465 |     |     |     |     | 470 |     |     |     |     | 475 |     |     |     |     | 480 |      |
| GAT | TCT | GTT | CTA | CTT | ATC | ATT | GAT | TCC | GTT | AGC | AAT | GCT | ATT | CGG | GAC | 1608 |
| Asp | Ser | Val | Leu | Leu | Ile | Ile | Asp | Ser | Val | Ser | Asn | Ala | Ile | Arg | Asp |      |
|     |     |     |     | 485 |     |     |     |     | 490 |     |     |     |     | 495 |     |      |
| CAA | TTT | ATC | AGC | AAG | TTA | CTT | TTT | TTT | GCA | TTT | GCA | GTT | AGT | ATT | TCC | 1656 |
| Gln | Phe | Ile | Ser | Lys | Leu | Leu | Phe | Phe | Ala | Phe | Ala | Val | Ser | Ile | Ser |      |
|     |     |     | 500 |     |     |     |     | 505 |     |     |     |     | 510 |     |     |      |
| ATC | AAT | GTC | TAC | TTA | CTG | AAT | GCT | GCA | AAA | ATT | CAC | ACA | GGA | TAC | ATG | 1704 |
| Ile | Asn | Val | Tyr | Leu | Leu | Asn | Ala | Ala | Lys | Ile | His | Thr | Gly | Tyr | Met |      |
|     |     | 515 |     |     |     |     | 520 |     |     |     |     | 525 |     |     |     |      |
| AAC | TTC | CAA | CCA | CAA | TCA | AAT | AAG | ATC | GAT | GAT | CTT | GTT | GTT | CAG | CAA | 1752 |
| Asn | Phe | Gln | Pro | Gln | Ser | Asn | Lys | Ile | Asp | Asp | Leu | Val | Val | Gln | Gln |      |
|     | 530 |     |     |     |     | 535 |     |     |     |     | 540 |     |     |     |     |      |
| AAA | TCG | GCA | ACG | ATT | GAG | TTT | TCA | GAA | ACT | CGA | AGT | ATG | CCT | GCT | TCT | 1800 |
| Lys | Ser | Ala | Thr | Ile | Glu | Phe | Ser | Glu | Thr | Arg | Ser | Met | Pro | Ala | Ser |      |
| 545 |     |     |     |     | 550 |     |     |     |     | 555 |     |     |     |     | 560 |      |
| TCT | GGC | CTA | GAA | ACT | CCA | GTG | ACC | GCG | AAA | GAT | ATA | ATT | ATC | TCT | GAA | 1848 |
| Ser | Gly | Leu | Glu | Thr | Pro | Val | Thr | Ala | Lys | Asp | Ile | Ile | Ile | Ser | Glu |      |
|     |     |     |     | 565 |     |     |     |     | 570 |     |     |     |     | 575 |     |      |
| GAA | ATC | CAG | AAT | AAC | GAA | TGC | GTC | TAT | GCT | TTG | AGT | TCC | CAG | GAC | GAG | 1896 |
| Glu | Ile | Gln | Asn | Asn | Glu | Cys | Val | Tyr | Ala | Leu | Ser | Ser | Gln | Asp | Glu |      |
|     |     |     | 580 |     |     |     |     | 585 |     |     |     |     | 590 |     |     |      |
| CCT | ATC | CGT | CCT | TTA | TCG | AAT | TTA | GTG | GAA | CTT | ATG | GAG | AAA | GAA | CAA | 1944 |
| Pro | Ile | Arg | Pro | Leu | Ser | Asn | Leu | Val | Glu | Leu | Met | Glu | Lys | Glu | Gln |      |
|     |     | 595 |     |     |     |     | 600 |     |     |     |     | 605 |     |     |     |      |
| TTA | AAG | AAC | ATG | AAT | AAT | ACT | GAG | GTT | TCG | AAT | CTT | GTC | GTC | AAC | GGT | 1992 |
| Leu | Lys | Asn | Met | Asn | Asn | Thr | Glu | Val | Ser | Asn | Leu | Val | Val | Asn | Gly |      |
|     | 610 |     |     |     |     | 615 |     |     |     |     | 620 |     |     |     |     |      |
| AAA | CTG | CCA | TTA | TAT | TCC | TTA | GAG | AAA | AAA | TTA | GAG | GAC | ACA | ACT | CGT | 2040 |
| Lys | Leu | Pro | Leu | Tyr | Ser | Leu | Glu | Lys | Lys | Leu | Glu | Asp | Thr | Thr | Arg |      |
| 625 |     |     |     |     | 630 |     |     |     |     | 635 |     |     |     |     | 640 |      |
| GCG | GTT | TTA | GTT | AGG | AGA | AAG | GCA | CTT | TCA | ACT | TTG | GCT | GAA | TCG | CCA | 2088 |
| Ala | Val | Leu | Val | Arg | Arg | Lys | Ala | Leu | Ser | Thr | Leu | Ala | Glu | Ser | Pro |      |
|     |     |     |     | 645 |     |     |     |     | 650 |     |     |     |     | 655 |     |      |
| ATT | TTA | GTT | TCC | GAA | AAA | TTG | CCC | TTC | AGA | AAT | TAT | GAT | TAT | GAT | CGC | 2136 |
| Ile | Leu | Val | Ser | Glu | Lys | Leu | Pro | Phe | Arg | Asn | Tyr | Asp | Tyr | Asp | Arg |      |
|     |     |     | 660 |     |     |     |     | 665 |     |     |     |     | 670 |     |     |      |

| | | | | | | | | | | | | | | | | |
|---|---|---|---|---|---|---|---|---|---|---|---|---|---|---|---|---|
| GTT | TTT | GGA | GCT | TGC | TGT | GAA | AAT | GTC | ATC | GGC | TAT | ATG | CCA | ATA | CCA | 2184 |
| Val | Phe | Gly | Ala | Cys | Cys | Glu | Asn | Val | Ile | Gly | Tyr | Met | Pro | Ile | Pro | |
| | | 675 | | | | 680 | | | | | 685 | | | | | |
| GTT | GGT | GTA | ATT | GGT | CCA | TTA | ATT | ATT | GAT | GGA | ACA | TCT | TAT | CAC | ATA | 2232 |
| Val | Gly | Val | Ile | Gly | Pro | Leu | Ile | Ile | Asp | Gly | Thr | Ser | Tyr | His | Ile | |
| | | 690 | | | | 695 | | | | | 700 | | | | | |
| CCA | ATG | GCA | ACC | ACG | GAA | GGT | TGT | TTA | GTG | GCT | TCA | GCT | ATG | CGT | GGT | 2280 |
| Pro | Met | Ala | Thr | Thr | Glu | Gly | Cys | Leu | Val | Ala | Ser | Ala | Met | Arg | Gly | |
| 705 | | | | | 710 | | | | | 715 | | | | | 720 | |
| TGC | AAA | GCC | ATC | AAT | GCT | GGT | GGT | GCA | ACA | ACT | GTT | TTA | ACC | AAA | | 2328 |
| Cys | Lys | Ala | Ile | Asn | Ala | Gly | Gly | Ala | Thr | Thr | Val | Leu | Thr | Lys | | |
| | | | | 725 | | | | | 730 | | | | | 735 | | |
| GAT | GGT | ATG | ACT | AGA | GGC | CCA | GTC | GTT | CGT | TTC | CCT | ACT | TTA | ATA | AGA | 2376 |
| Asp | Gly | Met | Thr | Arg | Gly | Pro | Val | Val | Arg | Phe | Pro | Thr | Leu | Ile | Arg | |
| | | | 740 | | | | | 745 | | | | | 750 | | | |
| TCT | GGT | GCC | TGC | AAG | ATA | TGG | TTA | GAC | TCG | GAA | GAG | GGA | CAA | AAT | TCA | 2424 |
| Ser | Gly | Ala | Cys | Lys | Ile | Trp | Leu | Asp | Ser | Glu | Glu | Gly | Gln | Asn | Ser | |
| | | | 755 | | | | | 760 | | | | | 765 | | | |
| ATT | AAA | AAA | GCT | TTT | AAT | TCT | ACA | TCA | AGG | TTT | GCA | CGT | TTG | CAA | CAT | 2472 |
| Ile | Lys | Lys | Ala | Phe | Asn | Ser | Thr | Ser | Arg | Phe | Ala | Arg | Leu | Gln | His | |
| | 770 | | | | | 775 | | | | | 780 | | | | | |
| ATT | CAA | ACC | TGT | CTA | GCA | GGC | GAT | TTG | CTT | TTT | ATG | AGA | TTT | CGG | ACA | 2520 |
| Ile | Gln | Thr | Cys | Leu | Ala | Gly | Asp | Leu | Leu | Phe | Met | Arg | Phe | Arg | Thr | |
| 785 | | | | | 790 | | | | | 795 | | | | | 800 | |
| ACT | ACC | GGT | GAC | GCA | ATG | GGT | ATG | AAC | ATG | ATA | TCG | AAA | GGT | GTC | GAA | 2568 |
| Thr | Thr | Gly | Asp | Ala | Met | Gly | Met | Asn | Met | Ile | Ser | Lys | Gly | Val | Glu | |
| | | | | 805 | | | | | 810 | | | | | 815 | | |
| TAC | TCT | TTG | AAA | CAA | ATG | GTA | GAA | GAA | TAT | GGT | TGG | GAA | GAT | ATG | GAA | 2616 |
| Tyr | Ser | Leu | Lys | Gln | Met | Val | Glu | Glu | Tyr | Gly | Trp | Glu | Asp | Met | Glu | |
| | | | 820 | | | | | 825 | | | | | 830 | | | |
| GTT | GTC | TCC | GTA | TCT | GGT | AAC | TAT | TGT | ACT | GAT | AAG | AAA | CCT | GCC | GCA | 2664 |
| Val | Val | Ser | Val | Ser | Gly | Asn | Tyr | Cys | Thr | Asp | Lys | Lys | Pro | Ala | Ala | |
| | | 835 | | | | | 840 | | | | | 845 | | | | |
| ATC | AAT | TGG | ATT | GAA | GGT | CGT | GGT | AAA | AGT | GTC | GTA | GCT | GAA | GCT | ACT | 2712 |
| Ile | Asn | Trp | Ile | Glu | Gly | Arg | Gly | Lys | Ser | Val | Val | Ala | Glu | Ala | Thr | |
| 850 | | | | | 855 | | | | | 860 | | | | | | |
| ATT | CCT | GGT | GAT | GTC | GTA | AAA | AGT | GTT | TTA | AAG | AGC | GAT | GTT | TCC | GCT | 2760 |
| Ile | Pro | Gly | Asp | Val | Val | Lys | Ser | Val | Leu | Lys | Ser | Asp | Val | Ser | Ala | |
| 865 | | | | | 870 | | | | | 875 | | | | | 880 | |
| TTA | GTT | GAA | TTA | AAT | ATA | TCC | AAG | AAC | TTG | GTT | GGA | TCC | GCA | ATG | GCT | 2808 |
| Leu | Val | Glu | Leu | Asn | Ile | Ser | Lys | Asn | Leu | Val | Gly | Ser | Ala | Met | Ala | |
| | | | | 885 | | | | | 890 | | | | | 895 | | |
| GGA | TCT | GTT | GGT | GGT | TTC | AAC | GCG | CAC | GCA | GCT | AAT | TTG | GTC | ACT | GCA | 2856 |
| Gly | Ser | Val | Gly | Gly | Phe | Asn | Ala | His | Ala | Ala | Asn | Leu | Val | Thr | Ala | |
| | | | 900 | | | | | 905 | | | | | 910 | | | |
| CTT | TTC | TTG | GCA | TTA | GGC | CAA | GAT | CCT | GCG | CAG | AAC | GTC | GAA | AGT | TCC | 2904 |
| Leu | Phe | Leu | Ala | Leu | Gly | Gln | Asp | Pro | Ala | Gln | Asn | Val | Glu | Ser | Ser | |
| | | 915 | | | | | 920 | | | | | 925 | | | | |
| AAC | TGT | ATA | ACT | TTG | ATG | AAG | GAA | GTT | GAT | GGT | GAT | TTA | AGG | ATC | TCT | 2952 |
| Asn | Cys | Ile | Thr | Leu | Met | Lys | Glu | Val | Asp | Gly | Asp | Leu | Arg | Ile | Ser | |
| | 930 | | | | | 935 | | | | | 940 | | | | | |
| GTT | TCC | ATG | CCA | TCT | ATT | GAA | GTT | GGT | ACG | ATT | GGC | GGG | GGT | ACT | GTT | 3000 |
| Val | Ser | Met | Pro | Ser | Ile | Glu | Val | Gly | Thr | Ile | Gly | Gly | Gly | Thr | Val | |
| 945 | | | | | 950 | | | | | 955 | | | | | 960 | |
| CTG | GAG | CCT | CAG | GGC | GCC | ATG | CTT | GAT | CTT | CTC | GGC | GTT | CGT | GGT | CCT | 3048 |
| Leu | Glu | Pro | Gln | Gly | Ala | Met | Leu | Asp | Leu | Leu | Gly | Val | Arg | Gly | Pro | |
| | | | | 965 | | | | | 970 | | | | | 975 | | |
| CAC | CCC | ACT | GAA | CCT | GGA | GCA | AAT | GCT | AGG | CAA | TTA | GCT | AGA | ATA | ATC | 3096 |
| His | Pro | Thr | Glu | Pro | Gly | Ala | Asn | Ala | Arg | Gln | Leu | Ala | Arg | Ile | Ile | |
| | | | 980 | | | | | 985 | | | | | 990 | | | |
| GCG | TGT | GCT | GTC | TTG | GCT | GGT | GAA | CTG | TCT | CTG | TGC | TCC | GCA | CTT | GCT | 3144 |
| Ala | Cys | Ala | Val | Leu | Ala | Gly | Glu | Leu | Ser | Leu | Cys | Ser | Ala | Leu | Ala | |

-continued

```
                995                          1000                         1005
GCC GGT CAC CTG GTA CAA AGC CAT ATG ACT CAC AAC CGT AAA ACA AAC          3192
Ala Gly His Leu Val Gln Ser His Met Thr His Asn Arg Lys Thr Asn
    1010                    1015                    1020

AAA GCC AAT GAA CTG CCA CAA CCA AGT AAC AAA GGG CCC CCC TGT AAA          3240
Lys Ala Asn Glu Leu Pro Gln Pro Ser Asn Lys Gly Pro Pro Cys Lys
1025                    1030                    1035                1040

ACC TCA GCA TTA TTA TAACTCTTGT AGTTACATG GTGATACTTT ATATCTTTGT           3295
Thr Ser Ala Leu Leu
                1045

ATTGTCTAGC TATTCTAAAT CATCTGCATG TAATAAGAAG TTGATCAAAA TGA              3348
```

( 2 ) INFORMATION FOR SEQ ID NO:6:

( i ) SEQUENCE CHARACTERISTICS:
        ( A ) LENGTH: 1045 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Leu Pro Leu Lys Thr Ile Val His Leu Val Lys Pro Phe Ala
 1               5                  10                      15

Cys Thr Ala Arg Phe Ser Ala Arg Tyr Pro Ile His Val Ile Val Val
                20                  25                  30

Ala Val Leu Leu Ser Ala Ala Ala Tyr Leu Ser Val Thr Gln Ser Tyr
            35                  40                  45

Leu Asn Glu Trp Lys Leu Asp Ser Asn Gln Tyr Ser Thr Tyr Leu Ser
    50                  55                  60

Ile Lys Pro Asp Glu Leu Phe Glu Lys Cys Thr His Tyr Tyr Arg Ser
 65                 70                  75                      80

Pro Val Ser Asp Thr Trp Lys Leu Leu Ser Ser Lys Glu Ala Ala Asp
                85                  90                  95

Ile Tyr Thr Pro Phe His Tyr Tyr Leu Ser Thr Ile Ser Phe Gln Ser
            100                 105                 110

Lys Asp Asn Ser Thr Thr Leu Pro Ser Leu Asp Asp Val Ile Tyr Ser
    115                 120                 125

Val Asp His Thr Arg Tyr Leu Leu Ser Glu Glu Pro Lys Ile Pro Thr
    130                 135                 140

Glu Leu Val Ser Glu Asn Gly Thr Lys Trp Arg Leu Arg Asn Asn Ser
145                 150                 155                 160

Asn Phe Ile Leu Asp Leu His Asn Ile Tyr Arg Asn Met Val Lys Gln
                165                 170                 175

Phe Ser Asn Lys Thr Ser Glu Phe Asp Gln Phe Asp Leu Phe Ile Ile
            180                 185                 190

Leu Ala Ala Tyr Leu Thr Leu Phe Tyr Thr Leu Cys Cys Leu Phe Asn
    195                 200                 205

Asp Met Arg Lys Ile Gly Ser Lys Phe Trp Leu Ser Phe Ser Ala Leu
    210                 215                 220

Ser Asn Ser Ala Cys Ala Leu Tyr Leu Ser Leu Tyr Thr Thr His Ser
225                 230                 235                 240

Leu Leu Lys Lys Pro Ala Ser Leu Leu Ser Leu Val Ile Gly Leu Pro
                245                 250                 255

Phe Ile Val Val Ile Ile Gly Phe Lys His Lys Val Arg Leu Ala Ala
            260                 265                 270

Phe Ser Leu Gln Lys Phe His Arg Ile Ser Ile Asp Lys Lys Ile Thr
    275                 280                 285
```

-continued

| | | | | | | | | | | | | | | |
|---|---|---|---|---|---|---|---|---|---|---|---|---|---|---|
| Val | Ser | Asn | Ile | Ile | Tyr | Glu | Ala | Met | Phe | Gln | Glu | Gly | Ala | Tyr | Leu |
| | 290 | | | | 295 | | | | 300 | | | | | |
| Ile | Arg | Asp | Tyr | Leu | Phe | Tyr | Ile | Ser | Ser | Phe | Ile | Gly | Cys | Ala | Ile |
| 305 | | | | | 310 | | | | 315 | | | | | | 320 |
| Tyr | Ala | Arg | His | Leu | Pro | Gly | Leu | Val | Asn | Phe | Cys | Ile | Leu | Ser | Thr |
| | | | | 325 | | | | | 330 | | | | | 335 | |
| Phe | Met | Leu | Val | Phe | Asp | Leu | Leu | Ser | Ala | Thr | Phe | Tyr | Ser | Ala |
| | | | 340 | | | | | 345 | | | | 350 | | |
| Ile | Leu | Ser | Met | Lys | Leu | Glu | Ile | Asn | Ile | Ile | His | Arg | Ser | Thr | Val |
| | | | 355 | | | | | 360 | | | | 365 | | | |
| Ile | Arg | Gln | Thr | Leu | Glu | Glu | Asp | Gly | Val | Val | Pro | Thr | Thr | Ala | Asp |
| | 370 | | | | | 375 | | | | | 380 | | | | |
| Ile | Ile | Tyr | Lys | Asp | Glu | Thr | Ala | Ser | Glu | Pro | His | Phe | Leu | Arg | Ser |
| 385 | | | | | 390 | | | | | 395 | | | | | 400 |
| Asn | Val | Ala | Ile | Ile | Leu | Gly | Lys | Ala | Ser | Val | Ile | Gly | Leu | Leu | Leu |
| | | | | 405 | | | | | 410 | | | | | 415 | |
| Leu | Ile | Asn | Leu | Tyr | Val | Phe | Thr | Asp | Lys | Leu | Asn | Ala | Thr | Ile | Leu |
| | | | 420 | | | | | 425 | | | | | 430 | | |
| Asn | Thr | Val | Tyr | Phe | Asp | Ser | Thr | Ile | Tyr | Ser | Leu | Pro | Asn | Phe | Ile |
| | | 435 | | | | | 440 | | | | | 445 | | | |
| Asn | Tyr | Lys | Asp | Ile | Gly | Asn | Leu | Ser | Asn | Gln | Val | Ile | Ile | Ser | Val |
| | 450 | | | | | 455 | | | | | 460 | | | | |
| Leu | Pro | Lys | Gln | Tyr | Tyr | Thr | Pro | Leu | Lys | Lys | Tyr | His | Gln | Ile | Glu |
| 465 | | | | | 470 | | | | | 475 | | | | | 480 |
| Asp | Ser | Val | Leu | Leu | Ile | Ile | Asp | Ser | Val | Ser | Asn | Ala | Ile | Arg | Asp |
| | | | | 485 | | | | | 490 | | | | | 495 | |
| Gln | Phe | Ile | Ser | Lys | Leu | Leu | Phe | Phe | Ala | Phe | Ala | Val | Ser | Ile | Ser |
| | | | | 500 | | | | | 505 | | | | | 510 | |
| Ile | Asn | Val | Tyr | Leu | Leu | Asn | Ala | Ala | Lys | Ile | His | Thr | Gly | Tyr | Met |
| | | | 515 | | | | | 520 | | | | | 525 | | |
| Asn | Phe | Gln | Pro | Gln | Ser | Asn | Lys | Ile | Asp | Asp | Leu | Val | Val | Gln | Gln |
| | | 530 | | | | | 535 | | | | | 540 | | | |
| Lys | Ser | Ala | Thr | Ile | Glu | Phe | Ser | Glu | Thr | Arg | Ser | Met | Pro | Ala | Ser |
| 545 | | | | | 550 | | | | | 555 | | | | | 560 |
| Ser | Gly | Leu | Glu | Thr | Pro | Val | Thr | Ala | Lys | Asp | Ile | Ile | Ser | Glu |
| | | | | 565 | | | | | 570 | | | | | 575 |
| Glu | Ile | Gln | Asn | Asn | Glu | Cys | Val | Tyr | Ala | Leu | Ser | Ser | Gln | Asp | Glu |
| | | | | 580 | | | | | 585 | | | | | 590 | |
| Pro | Ile | Arg | Pro | Leu | Ser | Asn | Leu | Val | Glu | Leu | Met | Glu | Lys | Glu | Gln |
| | | | 595 | | | | | 600 | | | | | 605 | | |
| Leu | Lys | Asn | Met | Asn | Asn | Thr | Glu | Val | Ser | Asn | Leu | Val | Val | Asn | Gly |
| | | 610 | | | | | 615 | | | | | 620 | | | |
| Lys | Leu | Pro | Leu | Tyr | Ser | Leu | Glu | Lys | Lys | Leu | Glu | Asp | Thr | Thr | Arg |
| 625 | | | | | 630 | | | | | 635 | | | | | 640 |
| Ala | Val | Leu | Val | Arg | Arg | Lys | Ala | Leu | Ser | Thr | Leu | Ala | Glu | Ser | Pro |
| | | | | 645 | | | | | 650 | | | | | 655 | |
| Ile | Leu | Val | Ser | Glu | Lys | Leu | Pro | Phe | Arg | Asn | Tyr | Asp | Tyr | Asp | Arg |
| | | | 660 | | | | | 665 | | | | | 670 | | |
| Val | Phe | Gly | Ala | Cys | Cys | Glu | Asn | Val | Ile | Gly | Tyr | Met | Pro | Ile | Pro |
| | | 675 | | | | | 680 | | | | | 685 | | | |
| Val | Gly | Val | Ile | Gly | Pro | Leu | Ile | Ile | Asp | Gly | Thr | Ser | Tyr | His | Ile |
| | 690 | | | | | 695 | | | | | 700 | | | | |
| Pro | Met | Ala | Thr | Thr | Glu | Gly | Cys | Leu | Val | Ala | Ser | Ala | Met | Arg | Gly |
| 705 | | | | | 710 | | | | | 715 | | | | | 720 |
| Cys | Lys | Ala | Ile | Asn | Ala | Gly | Gly | Gly | Ala | Thr | Thr | Val | Leu | Thr | Lys |

|   |   |   | 725 |   |   |   |   | 730 |   |   |   |   | 735 |   |
|---|---|---|---|---|---|---|---|---|---|---|---|---|---|---|
| Asp | Gly | Met | Thr | Arg | Gly | Pro | Val | Val | Arg | Phe | Pro | Thr | Leu | Ile | Arg |
|   |   |   | 740 |   |   |   |   | 745 |   |   |   |   | 750 |   |
| Ser | Gly | Ala | Cys | Lys | Ile | Trp | Leu | Asp | Ser | Glu | Glu | Gly | Gln | Asn | Ser |
|   |   | 755 |   |   |   |   | 760 |   |   |   |   | 765 |   |   |
| Ile | Lys | Lys | Ala | Phe | Asn | Ser | Thr | Ser | Arg | Phe | Ala | Arg | Leu | Gln | His |
|   | 770 |   |   |   |   | 775 |   |   |   |   | 780 |   |   |   |
| Ile | Gln | Thr | Cys | Leu | Ala | Gly | Asp | Leu | Leu | Phe | Met | Arg | Phe | Arg | Thr |
| 785 |   |   |   |   | 790 |   |   |   |   | 795 |   |   |   |   | 800 |
| Thr | Thr | Gly | Asp | Ala | Met | Gly | Met | Asn | Met | Ile | Ser | Lys | Gly | Val | Glu |
|   |   |   |   | 805 |   |   |   | 810 |   |   |   |   |   | 815 |   |
| Tyr | Ser | Leu | Lys | Gln | Met | Val | Glu | Glu | Tyr | Gly | Trp | Glu | Asp | Met | Glu |
|   |   |   | 820 |   |   |   |   | 825 |   |   |   |   | 830 |   |   |
| Val | Val | Ser | Val | Ser | Gly | Asn | Tyr | Cys | Thr | Asp | Lys | Lys | Pro | Ala | Ala |
|   |   | 835 |   |   |   |   | 840 |   |   |   |   | 845 |   |   |   |
| Ile | Asn | Trp | Ile | Glu | Gly | Arg | Gly | Lys | Ser | Val | Val | Ala | Glu | Ala | Thr |
|   | 850 |   |   |   |   | 855 |   |   |   |   | 860 |   |   |   |   |
| Ile | Pro | Gly | Asp | Val | Val | Lys | Ser | Val | Leu | Lys | Ser | Asp | Val | Ser | Ala |
| 865 |   |   |   |   | 870 |   |   |   |   | 875 |   |   |   |   | 880 |
| Leu | Val | Glu | Leu | Asn | Ile | Ser | Lys | Asn | Leu | Val | Gly | Ser | Ala | Met | Ala |
|   |   |   |   | 885 |   |   |   |   | 890 |   |   |   |   | 895 |   |
| Gly | Ser | Val | Gly | Gly | Phe | Asn | Ala | His | Ala | Ala | Asn | Leu | Val | Thr | Ala |
|   |   |   | 900 |   |   |   |   | 905 |   |   |   |   | 910 |   |   |
| Leu | Phe | Leu | Ala | Leu | Gly | Gln | Asp | Pro | Ala | Gln | Asn | Val | Glu | Ser | Ser |
|   |   | 915 |   |   |   |   | 920 |   |   |   |   | 925 |   |   |   |
| Asn | Cys | Ile | Thr | Leu | Met | Lys | Glu | Val | Asp | Gly | Asp | Leu | Arg | Ile | Ser |
|   | 930 |   |   |   |   | 935 |   |   |   |   | 940 |   |   |   |   |
| Val | Ser | Met | Pro | Ser | Ile | Glu | Val | Gly | Thr | Ile | Gly | Gly | Gly | Thr | Val |
| 945 |   |   |   |   | 950 |   |   |   |   | 955 |   |   |   |   | 960 |
| Leu | Glu | Pro | Gln | Gly | Ala | Met | Leu | Asp | Leu | Leu | Gly | Val | Arg | Gly | Pro |
|   |   |   |   | 965 |   |   |   |   | 970 |   |   |   |   | 975 |   |
| His | Pro | Thr | Glu | Pro | Gly | Ala | Asn | Ala | Arg | Gln | Leu | Ala | Arg | Ile | Ile |
|   |   |   | 980 |   |   |   |   | 985 |   |   |   |   | 990 |   |   |
| Ala | Cys | Ala | Val | Leu | Ala | Gly | Glu | Leu | Ser | Leu | Cys | Ser | Ala | Leu | Ala |
|   |   | 995 |   |   |   |   | 1000 |   |   |   |   | 1005 |   |   |   |
| Ala | Gly | His | Leu | Val | Gln | Ser | His | Met | Thr | His | Asn | Arg | Lys | Thr | Asn |
|   |   | 1010 |   |   |   |   | 1015 |   |   |   |   | 1020 |   |   |   |
| Lys | Ala | Asn | Glu | Leu | Pro | Gln | Pro | Ser | Asn | Lys | Gly | Pro | Pro | Cys | Lys |
| 1025 |   |   |   |   | 1030 |   |   |   |   | 1035 |   |   |   |   | 1040 |
| Thr | Ser | Ala | Leu | Leu |   |   |   |   |   |   |   |   |   |   |   |
|   |   |   |   | 1045 |   |   |   |   |   |   |   |   |   |   |   |

PROCESS AND COMPOSITION FOR INCREASING SQUALENE AND STEROL ACCUMULATION IN HIGHER PLANTS

CROSS-REFERENCE TO RELATED APPLICATION

This is a continuation-in-part of application Ser. No. 07/596,467, filed Oct. 12, 1990, whose disclosures are incorporated by reference herein.

TECHNICAL FIELD

The present invention relates to processes and compositions for increasing the accumulation of squalene and sterols in higher plants, and more particularly to increasing squalene and non-delta-5 sterol accumulation by increasing the amount of a gene encoding a polypeptide having HMG-CoA reductase activity.

BACKGROUND OF THE INVENTION

Acetate is the metabolic precursor of a vast array of compounds vital for cell and organism viability. Acetyl coenzyme A (CoA) reacts with acetoacetyl CoA to form 3-hydroxy-3-methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

Sterols are derivatives of a fused, reduced ring system, cyclopenta-[a]-phenanthrene, comprising three fused cyclohexane rings (A, B and C) in a phenanthrene arrangement, and a terminal cyclopentane ring (D) having the formula and carbon atom position numbering shown below:

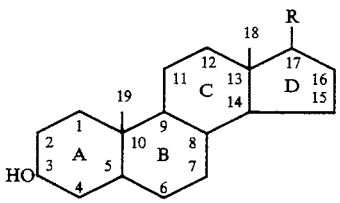

where R is an 8 to 10 carbon-atom side chain.

In plants, squalene is converted to squalene epoxide, which is then cyclized to form cycloartenol (4,4,14α-trimethyl-9β,19 cyclo-5α-cholest-24-en-3β-ol). Cycloartenol has two methyl groups at position 4, a methyl group at position 14, a methylene bridge between the carbon atoms at positions 9 and 19 that forms a disubstituted cyclopropyl group at those positions, and includes an 8 carbon sidechain of the formula: $CH_3CH(CH_2)_2CH=C(CH_3)_2$.

Cycloartenol is formed in an early stage in the biosynthetic pathway of sterol production in higher plants. Cycloartenol is formed from squalene epoxide, which is formed from squalene, a derivative of mevalonic acid (mevalonate). Squalene epoxide can alternatively be converted into pentacyclic sterols, containing five instead of four rings. Exemplary pentacyclic sterols include the phytoalexins and saponins.

Being one of the first sterols in the higher plant biosynthetic pathway, cycloartenol serves as a precursor for the production of numerous other sterols. In normal plants, cycloartenol is converted to predominantly 24-methylene cycloartenol (4,4,14α-trimethyl-9β,19 cyclo-22,23-dihydro-ergosta-24(28)-en-3-β -ol), cycloeucalenol (4,14α-dimethyl-9β,19 cyclo-5α-ergost-24(28)-en-3β-ol), obtusifoliol (4,14α-dimethyl-5α-ergosta-8,24(28)-dien-3β-ol), isofucosterol (5α-stigmasta-5-Z-24(28)-dien-3β-ol), sitosterol (5α-stigmasta-5-en-3β-ol), stigmasterol-(stigmasta-5,E-22-dien-3β-ol), campesterol (5α-ergosta-5-en-3β-ol), and cholesterol (5α-cholesta-5-en-3β-ol).

Although sterols produced by plants, and particularly higher (vascular) plants, can be grouped by the presence or absence of one or more of several functionalities, plant sterols are classified into two general groups herein; i.e., those containing a double bond between the carbon atoms at positions 5 and 6 (delta-5 or Δ5 sterols) and those not containing a double bond between the carbon atoms at positions 5 and 6 (non-delta-5 sterols).

Exemplary naturally occurring delta-5 plant sterols isofucosterol, sitosterol, stigmasterol, campesterol, cholesterol, and dihydrobrassicasterol. Exemplary naturally occurring non-delta-5 plant sterols are cycloartenol, 24-methylene cycloartenol, cycloeucalenol, and obtusifoliol.

The most abundant sterols of vascular plants are campesterol, sitosterol and stigmasterol, all of which contain a double bond between the carbon atoms at positions 5 and 6 and are classified as delta-5 sterols.

The ratio of delta-5 to non-delta-5 sterols in plants can be an important factor relating to insect pest resistance. Insect pests are unable to synthesize de novo the steroid nucleus and depend upon external sources of sterols in their food source for production of necessary steroid compounds. In particular, insect pests require an external source of delta-5 sterols. By way of example, externally provided delta-5 sterols are necessary for the production of ecdysteroids, hormones that control reproduction and development. See, e.g., Costet et al., Proc. Natl. Acad. Sci. USA, 84:643 (1987) and Corio-Costet et al., Archives of Insect Biochem. Physiol., 11:47 (1989).

Treatment of wheat with the fungicide fenpropimorph reduced delta-5 sterol content from about 93 percent of total sterol to about 1 percent of total sterol and increased non-delta-5 sterol content from about 7 percent of total sterol to about 99 percent of total sterol. Where the phytophagous grasshopper Locusta migratoria was reared feeding on wheat seedlings treated with fenpropimorph, the concentration of ecdysteroids in eggs was reduced by 80 percent. Those eggs either did not develop (meiosis is inhibited) or they developed with complex abnormalities and malfunctions. Costet et al., Proc. Natl. Acad. Sci. USA, 84:643 (1987); Corio-Costet et al., Archives of Insect Biochem. Physiol., 11:47 (1989).

Because insects can use delta-5 sterols for steroid production, those delta-5 sterols are referred to herein as "utilizable" sterols. Non-delta-5 sterols are referred to herein as "non-utilizable" sterols.

Naturally occurring higher plants typically contain an excess of utilizable over non-utilizable sterols. Costet et al., Proc. Natl. Acad. Sci. USA, 84:643 (1987); Corio-Costet et al., Archives of Insect Biochem. Physiol., 11:47

(1989). Such plants thus can provide an appropriate food supply for insect pests.

Plants having an abundance of non-utilizable sterols have also been produced by treatment with inhibitors of sterol biosynthesis such as the fungicides triarimol, tridemorph, and triparanol. Hosokawa et al., *Lipids*, 19(6):449 (1984). The use of fungicides, however, is undesirable in light of the adverse environmental effects attendant with the use of such chemicals.

All of the fungicides discussed above are known to inhibit sterol biosynthesis subsequent to the formation of cycloartenol.

As set forth above, cycloartenol is a metabolic derivative of mevalonate, which is formed from the reduction of 3-hydroxy-3-methylglutaryl coenzyme A (HMG-CoA). The reduction of HMG-CoA to mevalonate is catalyzed by the enzyme HMG-CoA reductase.

The HMG-CoA reductase enzymes of animals and yeasts are integral membrane glycoproteins of the endoplasmic reticulum. The intact enzyme comprises three regions: a catalytic region, containing the active site of the enzyme; a membrane binding region, anchoring the enzyme to the endoplasmic reticulum; and a linker region, joining the catalytic and membrane binding regions of the enzymes. The membrane binding region occupies the $NH_2$-terminal portion of the intact protein, whereas the catalytic region occupies the COOH-terminal portion of the protein, with the linker region constituting the remaining portion. Basson, M. E. et al., *Mol. Cell Biol.*, 8(9):3797–3808 (1988). At present, the subcellular localization of HMG-CoA reductase in plants is not known. Russell, D. W. et al., *Current Topics in Plant Biochemistry*, Vol. 4, ed. by D. D. Randall et al., Univ. of Missouri (1985).

The activity of HMG-CoA reductase in animals and yeasts is known to be subject to feedback inhibition by sterols. Such feedback inhibition requires the presence of the membrane binding region of the enzyme. See, e.g., Gil, G. et al., *Cell*, 41: 249–258(1985); Bard, M. and Downing, J. F. *Journal of General Microbiology*, 125:415–420(1981).

Given that mevalonate is the precursor for sterols and other isoprenoids, it might be expected that increases in the amount or activity of HMG-CoA reductase would lead to increases in the accumulation of both sterols and other isoprenoids. In yeasts and non-photosynthetic microorganisms, increases in HMG-CoA reductase activity are not associated with predictable increases in the production of sterols or other isoprenoids.

In mutant strains of the yeast *Saccharomyces cerevisiae* (S. cerevisiae) having abnormally high levels of HMG-CoA reductase activity, the production of two sterols, 4,14-dimethylzymosterol and 14-methylfecosterol, is markedly increased above normal. Downing et al., *Biochemical and Biophysical Research Communications*, 94(3): 974–979(1980).

When HMG-CoA reductase activity was increased by illumination in non-photosynthetic microorganisms, isoprenoid (carotenoid), but not sterol (ergosterol), synthesis was enhanced. Tada et al., *Plant and Cell Physiology*, 23(4): 615–621(1982). There are no studies reporting the effects of such increases in HMG-CoA reductase activity in plants.

SUMMARY OF THE INVENTION

The present invention provides a process of increasing sterol accumulation in a transgenic plant comprising:

(a) transforming a plant cell with a recombinant DNA molecule comprising a vector operatively linked to a DNA segment that encodes a polypeptide having HMG-CoA reductase activity and a promoter suitable for driving the expression of said polypeptide in said plant cell to form a transformed plant cell; and (b) regenerating the transformed plant cell into the transgenic plant.

A polypeptide having HMG-CoA reductase activity preferably comprises the catalytic region and at least a portion of the linker region but is free from the membrane binding region of a HMG-CoA reductase. In a preferred embodiment, the promoter is a promoter whose regulatory function is substantially unaffected by the level of sterol in said transgenic plant such as the CaMV 35S promoter. A preferred recombinant DNA molecule is plasmid HMGRΔ227-pKYLX71.

The plant cell is preferably obtained from plants of the group consisting of tobacco, cotton, soybean, tomato and alfalfa. A sterol whose accumulation is increased is preferably a non-delta-5 sterol and, more preferably cycloartenol.

A similar process to that set forth above is used increase squalene accumulation and to increase pest resistance in a transgenic plant.

The present invention further contemplates a transgenic plant produced in accordance with any of the above processes.

Still further, the present invention contemplates a transgenic plant that (a) has an increased amount of a structural gene that encodes a polypeptide having HMG-CoA reductase activity and (b) over accumulates sterols or squalene relative to a native, non-transgenic plant of the same strain.

The encoded polypeptide is preferably an intact HMG-CoA reductase enzyme or an active, truncated HMG-CoA reductase enzyme comprising the catalytic and at least a portion of the linker region that is free from the membrane binding region of a HMG-CoA reductase enzyme such as a hamster HMG-CoA reductase.

Preferably, the transgenic plant is a transgenic tobacco, cotton, soybean, tomato or alfalfa plant. The present invention also contemplates a transgenic tobacco plant whose seeds have ATCC accession No. 40904 and mutants, recombinants, genetically engineered derivatives thereof and hybrids derived therefrom.

In a still further aspect, the present invention contemplates a transgenic plant seed capable of germinating into a transgenic plant that over accumulates sterol or squalene relative to a native, non-transgenic plant of the same strain and mutants, recombinants, genetically engineered derivatives thereof and hybrids derived therefrom.

BRIEF DESCRIPTION OF THE DRAWINGS

In the drawings forming a portion of this disclosure:

FIG. 1 is a schematic representation of the metabolism of acetyl coenzyme A to sterols and other isoprenoids in plants as published by Russell et al., *Current*

*Topics in Plant Biochemistry*, Vol. 4, ed. by D. D. Randall et al., Univ. of Missouri (1985).

FIGS. 2A–2K shown as eleven panels designated FIGS. 2A through 2K, are the composite nucleotide sequence of the cDNA corresponding to the mRNA for hamster HMG-CoA reductase (SEQ ID NO:1), and the predicted amino acid sequence (SEQ ID NO:2) of the protein as published by Chin et al., *Nature*, 308:613–617 (1984). Nucleotides are numbered (right-hand side) in the 5' to 3' direction. The predicted amino acid sequence is shown below the nucleotide sequence. The amino acid residues are numbered below every fifth amino acid beginning with the initiator methionine.

FIGS. 3A–3J, shown as ten panels designated FIGS. 3A through 3J, are the nucleotide base sequence (SEQ ID NO:3) and derived amino acid residue sequence (SEQ ID NO:4) for *S. cerevisiae* HMG-CoA reductase 1 published by Basson, M. E. et al., *Mol. Cell Biol.*, 8(9):3797–3808 (1988). Nucleotides are shown and numbered as discussed for FIG. 2 as are the derived amino acid residues.

FIG. 4 is a schematic drawing showing the structure of a plasmid (pRed-227Δ) used to insert a truncated hamster gene encoding for hamster HMG-CoA reductase into cells lacking such hamster enzyme. Base pairs of the reductase coding sequence (nucleotides 28 to 1023) that encode amino acids 10 to 341 have been deleted and are shown externally of the plasmid. The hatched area denotes the reductase cDNA sequence portion of the plasmid. The reductase cDNA initiator methionine codon (nucleotide 1) and terminator codon (nucleotide 2662) are indicated, as are other features of the plasmid.

FIG. 5 is a schematic restriction map of plasmid HMGRΔ227-pKYLX71 used to transform the plants of the present invention.

DETAILED DESCRIPTION OF THE INVENTION

I. Definitions

The following words and phrases have the meanings set forth below.

Expression: The combination of intracellular processes, including transcription and translation undergone by a structural gene to produce a polypeptide.

Plant integrating vector: A polynucleotide having a first portion containing a structural gene and control elements that direct and regulate expression of that structural gene when operatively linked to that gene and a second portion containing polynucleotide sequences that permit the first portion to be integrated into the chromosome of a plant cell.

Operatively linked: A structural gene is covalently bonded in correct reading frame to another DNA (or RNA as appropriate) segment, such as to a plant integrating vector so that the structural gene is under the control of the plant integrating vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecule: A hybrid DNA sequence comprising at least two nucleotide sequences not normally found together in nature.

Regeneration: The process of growing a plant from a plant cell (e.g. plant protoplast or explant).

Structural gene: A DNA sequence that is expressed as a polypeptide, i.e., an amino acid residue sequence.

Transformation: A process of introducing an exogenous sequence (e.g. a vector, a recombinant DNA molecule) into a cell or protoplasts in which that exogenous DNA is incorporated into a chromosome.

Transformed plant cell: A plant cell whose DNA has been altered by the introduction of an exogenous DNA molecule into that cell or protoplast.

Transgenic plant cell: Any plant cell derived or regenerated from a transformed plant cell or protoplast or derived from a transgenic plant. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

II. The Invention

A. Processes for Increasing Sterol Accumulation

In one aspect, the present invention relates to a process for increasing sterol accumulation in transgenic plants, as well as to the transgenic plants that exhibit increased sterol accumulation relative to a native variety of the plant. Preferably, the increase in sterol accumulation is the result of an increased accumulation of non-delta-5 sterols (i.e., sterols lacking a double bond between the carbon atoms at positions 5 and 6 of the sterol nucleus).

A plant contemplated by this invention is a vascular, multicellular higher plant. Such higher plants will hereinafter be usually referred to simply as "plants". Such "plants" include both complete entities having leaves, stems, seeds, roots and the like as well as callus and cell cultures that are monocotyledonous and dicotyledonous. Dicotyledonous plants are a preferred embodiment of the present invention.

Preferred plants are members of the Solanaceae, Leguminosae, Ammiaceae, Brassicaceae, Gramineae, Carduaceae and Malvaceae families. Exemplary plant members of those families are tobacco, petunia and tomato (Solanaceae), soybean and alfalfa (Leguminosae), carrot (Ammiaceae), corn and barley (Gramineae, arabidopsis (Brassicaceae), guayule (Carduaceae), and cotton (Malvaceae). A preferred plant is tobacco of the strain *Nicotiana tabacum* (*N. tabacum*), cotton of the strain Coker line 312-5A, soybean of the strain *Glycine max*, alfalfa of the strain RYSI or tomato of the strain *Lycopersicon esculentum*.

A transgenic plant contemplated by this invention is produced by transforming a plant cell or protoplast with an added, exogenous structural gene that encodes a polypeptide having HMG-CoA reductase activity to produce a transformed plant cell, and regenerating a transgenic plant from the transformed plant cell. The encoded polypeptide is expressed both in the transformed plant cell or protoplast and the resulting transgenic plant. (The phrase "plant cell" will hereinafter be used to include a plant protoplast, except where plant protoplasts are specifically discussed.)

A non-transgenic plant that serves as the source of the plant cell that is transformed; i.e., the precursor cell, is referred to herein as a "native, non-transgenic" plant. The native, non-transgenic plant is of the same strain as the formed transgenic plant.

Sterol production in a transgenic plant of the present invention is increased by increasing the activity of the enzyme HMG-CoA reductase, which enzyme catalyzes the conversion of 3-hydroxy-3-methylglutaryl Coenzyme A (HMG-CoA) to mevalonate. As used herein, "activity" means the total catalytic activity of HMG-CoA reductase in a plant cell. As used herein, the term "specific activity" means the activity normalized to cellular protein content.

HMG-CoA reductase activity is increased by increasing the amount (copy number) of a gene encoding a polypeptide having HMG-CoA reductase catalytic activity. Expression of the increased amount of that encoded structural gene enhances the activity of that enzyme.

The amount of the expressed gene is increased by transforming a plant cell with a recombinant DNA molecule comprising a vector operatively linked to a DNA segment that encodes a polypeptide having HMG-CoA reductase activity, and a promoter suitable for driving the expression of that polypeptide in that plant cell, and culturing the transformed plant cell into a transgenic plant. Such a polypeptide includes intact as well as catalytically active, truncated HMG-CoA reductase proteins.

Thus, a transformed plant cell and a transgenic plant have one or more added, exogenous genes that encode a polypeptide having HMG-CoA reductase activity relative to a native, non-transgenic plant or untransformed plant cell of the same type. As such, a transformed plant cell or transgenic plant can be distinguished from an untransformed plant cell or native, non-transgenic plant by standard technology such as agarose separation of DNA fragments or mRNAs followed by transfer and appropriate blotting with DNA or RNA, e.g., Southern or Northern blotting, or by use of polymerase chain reaction technology, as are well known. Relative HMG-CoA reductase activity of the transformed cell or transgenic plant with untransformed cells and native, non-transgenic plants or cell cultures therefrom can also be compared, with a relative activity for that enzyme of about 1.5:1 for transgenic (transformed):native (untransformed) showing transformation. Higher relative activity ratios such as about 15:1 have also been observed.

Sterol accumulation can also be used to distinguish between native, non-transgenic and transgenic plants. A transgenic plant has at least about twice the total sterol content as a native, non-transgenic plant where a single added gene is present. Greater differences up to about forty-fold have also been observed.

The increased accumulation of sterol is preferably the result of an increase in the accumulation of non-delta-5 sterols lacking a double bond between the carbon atoms at positions 5 and 6.

By way of example, in transgenic tobacco made in accordance with a process of the present invention, the increase in sterol accumulation was found to be due predominantly to an increase in the accumulation of the non-delta-5 sterol cycloartenol (See Example 3 hereinafter). Increases in non-delta-5 sterols were also observed in transgenic cotton, soybean, tomato and alfalfa plant callus cultures (See Examples 6, 7, 8 and 9 hereinafter).

B. Processes for Increasing Squalene Accumulation

In another aspect, the present invention relates to processes for increasing squalene accumulation in transgenic plants, as well as to the transgenic plants that exhibit increased squalene accumulation relative to a native, non-transgenic plant of the same strain.

Squalene production in a transgenic plant of the present invention is increased by increasing the activity of the enzyme HMG-CoA reductase. The increase in HMG-CoA reductase activity is carried out in accordance with the processes discussed above relating to a process for increasing sterol accumulation.

Although similar processes are used to increase sterol and squalene accumulation in transgenic plants, there does not appear to be any causal or necessary relationship between the increased accumulation of those compounds. For example, observed increases in sterol accumulation of transgenic plants of the present invention do not correlate with increases in squalene accumulation in those same plants. Table 1, below, shows the increases in sterol and squalene accumulation in transgenic tobacco, cotton, soybean, tomato and alfalfa callus. The data in Table 1 are taken from the data in Tables 6, 7, 8, 9 and 10 hereinafter. The Delta values shown in Table 1 represent averages of the individual data in Tables 6–10.

TABLE 1

| Plant | Control | Transgenic | Delta[2] (Cont-Trans) |
|---|---|---|---|
| Sterol Accumulation[1] | | | |
| Tobacco | 0.21 | 0.78 | 0.57 |
| Cotton | 0.16 | 0.60 | 0.44 |
| Soybean | 0.37 | 0.85 | 0.48 |
| Tomato | 0.04 | 0.99 | 0.95 |
| Alfalfa | 0.24 | 1.26 | 1.02 |
| Squalene Accumulation[1] | | | |
| Tobacco | <0.010 | 0.126 | 0.126 |
| Cotton | <0.002 | 0.560 | 0.560 |
| Soybean | 0.022 | 0.233 | 0.211 |
| Tomato | <0.002 | 0.090 | 0.090 |
| Alfalfa | 0.002 | 0.052 | 0.050 |

[1]Sterol and squalene levels of Control and Transgenic callus are given as percentage of dry weight
[2]Delta values are calculated as control minus transgenic (Cont-Trans) levels. Where the control value is trace (tr) or <0.01, the delta value is calculated as the level in the transgenic callus.

It can be seen that there is no correlation between increases in sterol and squalene accumulation. In tobacco, the increase in sterol accumulation (0.57) was associated with an increase in squalene accumulation of 0,126. In marked contrast, in alfalfa where the increase in sterol accumulation was twice that seen in tobacco (1.02 vs. 0.57), the accumulation of squalene was only one-twentieth that seen in tobacco (0.05 vs. 0.126). These data show the likely independent effects of transformation and formation of transgenic plants on sterol and squalene accumulation.

Squalene accumulation can also be used to distinguish between transgenie and native, non-transgenic plants.

Thus, a transgenic plant contemplated herein can accumulate about 5 to about 75 times the squalene of a native, non-transformed, plant.

C. Structural Genes

The present invention contemplates transforming a plant cell with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane binding region and the linker region.

The catalytic region contains the active site of the HMG-CoA reductase enzyme and comprises about forty percent of the COOH-terminal portion of intact HMG-CoA reductase enzyme.

The membrane binding region contains hydrophobic amino acid residues and comprises about fifty percent of the $NH_2$-terminal portion of intact HMG-CoA reductase enzyme.

The linker region connects the catalytic and membrane binding regions, and constitutes the remaining about ten percent of the intact enzyme.

As discussed in greater detail below, only the catalytic region of HMG-CoA reductase is needed herein to provide the desired enzyme activity. Thus, an exogenous structural gene that encodes a polypeptide corresponding to that catalytic region is the minimal gene required for transforming plant cells. The present invention therefore contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g., Carlson et al., *Cell*, 28:145 (1982); Rine et al., *Proc. Nat. Acad. Sci. USA*, 80:6750 (1983). Exemplary of such structural genes are the mammalian and yeast genes encoding HMG-CoA reductase or the catalytic region thereof.

The mammalian genome contains a single gene encoding HMG-CoA reductase. The nucleotide base sequence of the hamster and human gene for HMG-CoA reductase have been described. A composite nucleotide sequence of cDNA corresponding to the mRNA (SEQ ID NO:1), as well as the derived amino acid residue sequence (SEQ ID NO:2), for hamster HMG-CoA reductase is provided in FIG. 2, reprinted from Chin et al., *Nature*, 308:613 (1984). The composite nucleotide sequence of FIG. 2 (SEQ ID NO:1), comprising about 4768 base pairs, includes the nucleotide sequence encoding the intact hamster HMG-CoA reductase enzyme.

Intact hamster HMG-CoA reductase comprises about 887 amino acid residues (SEQ ID NO:2). A structural gene encoding an intact hamster HMG-CoA reductase enzyme of 887 amino acid residues comprises base pairs from about nucleotide position 164 to about nucleotide position 2824 of FIG. 2 (SEQ ID NO:1).

A preferred structural gene is one that encodes a polypeptide corresponding to only the catalytic region of the enzyme. Two catalytically active segments of hamster HMG-CoA reductase have been defined. Liscum et al., *J. Biol. Chem.*, 260(1):522 (1985). One segment containing a catalytic region has an apparent molecular weight of 62 kDa and comprises amino acid residues from about position 373 to about position 887. A second segment containing a catalytic region has an apparent molecular weight of 53 kDa segment and comprises amino acid residues from about position 460 to about position 887. The 62 kDa catalytically active segment is encoded by base pairs from about nucleotide position 1280 to about nucleotide position 2824 of FIG. 2 (SEQ ID NO:1). The 53 kDa catalytically active segment is encoded by base pairs from about nucleotide position 1541 to about nucleotide position 2824 of FIG. 2 (SEQ ID NO:1).

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1180 to about nucleotide position 1283 or from about position 1180 to about position 1540 respectively of FIG. 2 (SEQ ID NO:1). The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme. A truncated hamster HMG-CoA reductase gene, designated HMGR-Δ227, comprising nucleotides 164–190 operatively linked to nucleotides 1187–2824 from FIG. 2 (SEQ ID NO:1), which encodes amino acid residues 1–9 (from the membrane binding region) and 342–887 has been used to transform plant cells. The schematic structure of the transforming plasmid (pRED-227Δ) containing the truncated gene is reprinted in FIG. 4. A structural gene encoding a polypeptide comprising a catalytically active, truncated or intact HMG-CoA reductase enzyme from other organisms such as yeast can also be used in accordance with the present invention.

Yeast cells contain two genes encoding HMG-CoA reductase. The two yeast genes, designated HMG1 and HMG2, encode two distinct forms of HMG-CoA reductase, designated HMG-CoA reductase 1 and HMG-CoA reductase 2. The nucleotide base sequence of HMG1 (SEQ ID NO:3) as well as the amino acid residue sequence of HMG-CoA reductase 1 (SEQ ID NO:4) are presented in FIG. 3, taken from Basson et al., *Mol. Cell Biol.*, 8(9):3797 (1988). The nucleotide base sequences of HMG2 (SEQ ID NO:5) as well as the amino acid residue sequence of HMG-CoA reductase 2 (SEQ ID NO:6) are set forth hereinafter in the Sequence Listing.

The entire HMG1 gene comprises about 3360 base pairs (SEQ ID NO:3). Intact HMG-CoA reductase 1 comprises an amino acid sequence of about 1054 amino acid residues (SEQ ID NO:4). Thus, the minimal portion of the HMG1 gene that encodes an intact enzyme comprises base pairs from about nucleotide position 121 to about position 3282 of FIG. 3 (SEQ ID NO:3).

The entire HMG2 gene comprises about 3348 base pairs (SEQ ID NO:5). Intact HMG-CoA reductase 2 comprises about 1045 amino acid residues (SEQ ID NO:6). Thus, the minimal portion of HMG2 gene that encodes intact HMG-CoA reductase 2 comprises base pairs from about nucleotide position 121 to about position 3255 of FIG. 3 (SEQ ID NO:5).

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about residue 1054: i.e., the COOH-terminus. A structural gene that encodes the catalytic region comprises base pairs from about nucleotide position 1974 to about position 3282 of FIG. 3.

The linker region of HMG-CoA reductase 1 comprises an amino acid sequence from about residue 525 to about residue 617. A structural gene that encodes the linker region comprises nucleotides from about position 1695 to about position 1973 of FIG. 3. A structural gene encoding a polypeptide comprising the catalytic region and at least a portion of the linker region of yeast HMG-CoA reductase 1 preferably comprises the structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane binding region of the enzyme. Such a structural gene preferably comprises base pairs from about nucleotide position 121 to about position 147 and from about position 1695 to about position 3282 of FIG. 3.

A construct similar to those above from an analogous portion of yeast HMG-CoA reductase 2 can also be utilized.

It will be apparent to those of skill in the art that the nucleic acid sequences set forth herein, either explicitly, as in the case of the sequences set forth above, or implicitly with respect to nucleic acid sequences generally known and not presented herein, can be modified due to the built-in redundancy of the genetic code and non-critical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall lengths. That minimal length defines the length of a DNA segment having a sequence that encodes a particular polypeptide having HMG-CoA reductase activity. As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, a DNA segment of the invention can be up to 15,000 base pairs in length. The maximum size of a recombinant DNA molecule, particularly a plant integrating vector, is governed mostly by convenience and the vector size that can be accommodated by a host cell, once all of the minimal DNA sequences required for replication and expression, when desired, are present. Minimal vector sizes are well known.

D. Recombinant DNA Molecules

A recombinant DNA molecule of the present invention can be produced by operatively linking a vector to a useful DNA segment discussed before to form a plasmid such as those discussed herein. A particularly preferred recombinant DNA molecule is discussed in detail in Example 1, hereafter. A vector capable of directing the expression of a polypeptide having HMG-CoA reductase activity is referred to herein as an HMG-CoA reductase "plant integrating vector".

Such plant integrating vectors contain control elements that direct and regulate expression, including a promoter, a marker, a terminator and insertion sequences (see FIG. 5). The polypeptide coding genes are operatively linked to the plant integrating vector to allow the promoter sequence to direct RNA polymerase binding and expression of the desired polypeptide coding gene.

Useful in expressing the polypeptide coding gene are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chau et al., *Science*, 244:174–181 (1989). The promoter preferably comprises a promoter sequence whose function in regulating expression of the structural gene is substantially unaffected by the amount of sterol or squalene in the cell. As used herein, the term "substantially unaffected" means that the promoter is not responsive to direct feedback control by the sterols or squalene accumulated in transformed cells or transgenic plants.

A promoter is also selected for its ability to direct the transformed plant cell's or transgenic plant's transcriptional activity to the structural gene encoding a polypeptide having HMG-CoA reductase activity. Structural genes can be driven by a variety of promoters in plant tissues. Promoters can be near-constitutive, such as the CaMV 35S promoter, or tissue specific or developmentally specific promoters affecting dicots or monocots.

As exemplified and discussed in detail hereinafter, where the near-constitutive promoter CaMV 35S is used to transform tobacco plants, increases in total sterol and squalene accumulation are found in a variety of transformed plant tissues (e.g. callus, leaf, seed and root). Alternatively, the effects of transformation (e.g. increased amount of a gene coding for HMG-CoA reductase, increased total sterol accumulation and increased squalene accumulation) can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

A plant integrating vector containing a structural gene coding for a polypeptide having HMG-CoA reductase activity is engineered to be under control of the Lectin promoter and that vector is introduced into soybean plants using a protoplast transformation method. Dhir et al., *Plant Cell Reports*, 10:97 (1991). The expression of the polypeptide having HMG-CoA reductase activity is directed specifically to the seeds of the transgenic plant. In this way, a transgenic soybean seed having increased squalene accumulation is produced. Such seeds can then be used to extract oil containing enhanced levels of squalene. As set forth hereinafter, such squalene-enhanced oil is characterized by a greater thermal stability when compared to non-squalene-enhanced oil.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci. U.S.A.*, 87:4144–48 (1990)), corn alcohol dehydrogenase 1 (Vogel et al., *J. Cell Biochem.*, (supplement 13D, 312) (1989)), corn zein 19KD gene (storage protein) (Boston et al., *Plant Physiol.*, 83:742–46), corn light harvesting complex (Simpson, *Science*, 233:34 (1986), corn heat shock protein (O'Dell et al., *Nature*, 313:810–12 (1985), pea small subunit RuBP Carboxylase (Poulsen et al., *Mol. Gen. Genet.*, 205:193–200 (1986); Cushmore et al., *Gen. Eng. of Plants*, Plenum Press, New York, 29–38 (1983), Ti plasmid mannopine synthase (Langridge et al., *Proc. Natl. Acad. Sci. USA*, 86:3219–3223 (1989), Ti plasmid nopaline synthase (Langridge et al., *Proc. Natl. Acad. Sci. USA*, 86:3219–3223 (1989), petunia chalcone isomerase (Van Tunen et al., *EMBO J.*, 7:1257 (1988), bean glycine rich protein 1 (Keller et al., *EMBO J.*, 8:1309–14 (1989), CaMV 35s transcript (O'Dell et al., *Nature*, 313:810–12 (1985) and Potato patatin (Wenzler et al., *Plant Mol. Biol.*, 12:41–50 (1989). Preferred promoters are the cauliflower mosaic virus (CaMV 35S) promoter and the S-E9 small subunit RuBP carboxylase promoter.

The choice of which plant integrating vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene, i.e., the gene encoding HMG-CoA reductase activity, included in the DNA segment to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other plant integrating vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35S promoter.

The use of retroviral plant integrating vectors to form the recombinant DNAs of the present invention is also contemplated. As used herein, the term "retroviral plant integrating vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (988).

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the plant integrating vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into a plant integrating vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

A preferred recombinant DNA molecule utilized in accordance with the present invention is plasmid HMGRΔ227-pKYLX71.

E. Transformed Plant Cells, Transgenic Plants, Processes of Transformation and Processes of Regeneration The amount of a gene coding for a polypeptide having HMG-CoA reductase activity is increased by transforming a desired plant cell with a suitable vector that contains that added exogenous structural gene. Expression of that gene in the transformed plant cell and transgenic plants developed from that transformed plant cell enhances the activity of HMG-CoA reductase.

Methods for transforming polypeptide-coding genes into plant cells include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In addition, Agrobacteria containing both armed and disarmed Ti genes can be used for the transformations. Both types of transforming systems are illustrated herein. Transformants from the former system result in callus from which the desired squalene or sterol can be obtained, whereas transformants obtained from the latter, disarmed Ti genes can be regenerated into complete transgenic plants from whose tissues, e.g. leaf, seed and root, the desired chemicals can be obtained.

In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plant strains that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. USA*, 84:5345 (1987). Therefore, commercially important cereal grains such as rice, corn, and wheat must usually be transformed using alternative methods. However, as mentioned above, the transformation of asparagus using Agrobacterium can also be achieved. See, for example, Bytebier, et al., *Proc. Natl. Acad. Sci. USA*, 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis. A transgenic plant containing a single structural gene that encodes a polypeptide having HMG-CoA reductase activity; i.e., an independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced HMG-CoA reductase activity, sterol accumulation, or squalene accumulation or all three, relative to a control (native, non-transgenic) or an independent segregant transgenic plant. A homozygous transgenic plant exhibits enhanced HMG-CoA reductase activity, sterol and squalene accumulation as compared to both a native, non-transgenic plant and an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide having HMG-CoA activity. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen, Genet.*, 204:204 (1986); Callis et al., *Genes and Development*, 1:1183 (1987); and Marcotte et al., *Nature*, 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized.

Using that latter technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell*, 2:603–618 (1990); Klein, T. M. et al., *Plant Physiol.*, 91:440–444 (1989); Klein, T. M. et al., *Proc. Natl. Acad. Sci. USA*, 85:8502–8505 (1988); and Tomes, D. T. et al., *Plant Mol. Biol.*, 14:261–268 (1990). Transformation of tissue explants eliminates the need for passage through a protoplast stage and thus speeds the production of transgenic plants.

Thus, the amount of a gene coding for a polypeptide having HMG-CoA reductase activity can be increased in monocotyledonous plants such as corn by transforming those plants using particle bombardment methods. Maddock et al., *Third International Congress of Plant Molecular Biology, Abstract* 372 (1991). By way of example, a plant integrating vector containing a structural gene for HMG-CoA reductase and an appropriate selectable marker is transformed into a suspension of embryonic maize (corn) cells using a particle gun to deliver the DNA coated on microprojectiles. Transgenic plants are regenerated from transformed embryonic calli that express HMG-CoA reductase.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol,. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo* 1986, Butterworth, Stoneham, Mass., pp. 27–54 (1986).

The development or regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide having HMG-CoA activity introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Mature regenerated transgenic plants are obtained that exhibit increased sterol or squalene accumulation due to expression of the HMG-CoA reductase polypeptide gene. Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. The presence of the added gene in the progeny is assessed as discussed hereinafter.

A transgenic plant of the present invention containing a desired HMG-CoA reductase polypeptide is cultivated using methods well known to one skilled in the art. Any of the transgenic plants of the present invention can be cultivated to isolate the desired sterol or squalene products they contain.

A transgenic plant of this invention thus has an increased amount of a structural gene that encodes a polypeptide having HMG-CoA reductase activity. A preferred transgenic plant is an independent segregant for the added HMG-CoA reductase structural gene and can transmit that gene and its activity to its progeny. A more preferred transgenic plant is homozygous for that gene, and transmits that gene to all of its offspring on sexual mating.

A transgenic plant of the invention accumulates sterols and, particularly non-delta-5 sterols relative to a native plant. A transgenic plant of the invention also accumulates squalene relative to a native, non-transgenic plant. A transgenic plant also exhibits resistance to pests such as the hornworms and budworms as is discussed hereinafter.

F. Development of Commercial Hybrid Seed

Seed from a transgenic plant is grown in the field or greenhouse, and resulting sexually mature transgenic plants are self-pollinated to generate true breeding plants. The progeny from these plants become true breeding lines that are evaluated for sterol or squalene accumulation, preferably in the field, under a range of environmental conditions.

The commercial value of a transgenic plant with increased sterol or squalene accumulation is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, sterol or squalene accumulation is preferably bred into a large number of parental lines so that many hybrid combinations can be produced.

Adding an enhanced sterol or squalene accumulation trait to an agronomically elite line is accomplished by a variety of techniques well known to those of skill in the art. For example, parent transgenic plants that are either homozygous or contain a single independent segregatable gene that encodes a polypeptide having HMG-CoA activity and thus for enhanced sterol or squalene accumulation are crossed with lines having other desirable traits, such as herbicide resistance (U.S. Pat. No.

4,761,373) produce hybrids. Preferably, transgenic plants homozygous for enhanced sterol or squalene accumulation are used to generate hybrids.

For example, a transgenic plant homozygous for enhanced sterol accumulation is crossed with a parent plant having other desired traits. The progeny, which are heterozygous or independently segregatable for enhanced sterol accumulation, are backcrossed with the parent to obtain transgenic plants having enhanced sterol accumulation and the other desired traits. The backcrossing of progeny with the parent may have to be repeated more than once to obtain a transgenic plant that possesses all desirable traits.

Alternatively, transgenic plants with an enhanced sterol or squalene accumulation trait are made multiply transgenic by introducing into such plants other genes that encode and express other desirable traits, or are mutated as with radiation, e.g. X-rays or gamma rays, as in U.S. Pat. No. 4,616,099, whose disclosures are incorporates by reference. Thus, the present invention also contemplates mutants and genetically engineered derivatives of transgenic plants having enhanced sterol or squalene accumulation.

G. Accumulation of Sterols in Transgenic Plants

The present invention provides processes for increasing the accumulation of sterols, particularly non-delta-5 sterols, in transgenic plants. This is accomplished by increasing the amount of a gene encoding for a polypeptide having HMG-CoA reductase activity and subsequent expression of that encoded polypeptide.

In native, non-transgenic plants sterol accumulation is usually equal to about 0.3 weight percent of the dry weight on the plant. The predominant sterols accumulated by such normal plants are campesterol, sitosterol and stigmasterol. These sterols, Δ5-derivatives of cycloartenol that have undergone desaturation of the 5(6) carbon-carbon bond of cycloartenol, comprise over 80 weight percent of total sterols in native plants. Cycloartenol normally comprises from about 3 to about 30 percent of the total sterols present in such a plant.

Transgenic plants having an increased amount of a gene encoding a polypeptide having HMG-CoA reductase activity demonstrate a marked increase in total sterol accumulation when compared to a native, non-transgenic plant of the same strain. Further, the predominant sterol found in such transgenic plants is cycloartenol, which represents from about 60 to about 70 weight percent of total sterols of a transgenic plant.

Thus, the present invention provides transgenic plants that overaccumulate sterols relative to a native, non-transgenic plant. Transgenic plants with a single added gene accumulate total sterol to a level about twice that found in native, non-transgenic plants. In particular, such transgenic plants accumulate non-delta-5 sterols (e.g. cycloartenol) to a level from about ten to about one hundred times greater than found in native, non-transgenic plants.

These results are surprising and unexpected in light of studies relating HMG-CoA reductase activity and sterol accumulation in other organisms.

In yeast, increases in HMG-CoA reductase activity are associated with increases in squalene, 4,14-dimethyl-zymosterol and 14-methylfecosterol. Downing et al., *Biochemical and Biophysical Research Communications*, 94(3): 974-979 (1980). Increases in HMG-CoA reductase activity of yeast were not associated with increases in lanosterol, (a sterol of yeast analogous to cycloartenol). Benveniste, *Ann. Rev. Plant Physiol.*, 37:275-308 (1986).

In non-photosynthetic microorganisms, light-induced increases in HMG-CoA reductase activity were not associated with increases in sterol accumulation. Tada et al., *Plant and Cell Physiology*, 23(4):615-621(1982).

H. Increased Squalene Accumulation

The present invention provides processes for increasing the accumulation of squalene in transgenic plants. This is accomplished by increasing the amount of a gene encoding for a polypeptide having HMG-CoA reductase activity and subsequent expression of that encoded polypeptide in the transgenic plant.

Squalene has use as a bactericide, a pharmaceutical intermediate, and cosmetic ingredient. Further, enhanced squalene levels in or on rind can serve to protect citrus fruit against the harmful effects of chilling and freezing.

There is an inverse relationship between squalene levels in the epicuticular wax of grapefruit and severity of chilling injury in that fruit. Norby and McDonald, *Lipids*, 25:807–810 (1990), *J. Agric. Food Chem.*, 39:957–962 (1991), and U.S. Pat. No. 4,921,715. Further, where squalene was applied as a spray or dip to grapefruit, it prevented chill injury. Norby and McDonald, *Hortscience*, 25:94 (1990).

In a preferred embodiment, the present invention provides processes for increasing the accumulation of squalene in a transgenic citrus plant. This is accomplished by increasing the amount of a gene encoding for a-polypeptide having HMG-CoA reductase activity and subsequent expression of that encoded polypeptide in the transgenic plant.

The amount of a gene encoding for a polypeptide having HMG-CoA reductase activity is increased in a citrus plant by transforming a citrus plant cell in accordance with a process of the present invention. Means for transforming citrus plant cells using Agrobacterium-mediated transformation techniques are well known in the art.

Still further, squalene is reported to improve the heat stability of vegetable oils. The addition of squalene to rapeseed oil was found to retard the formation of thermally unstable polar compounds in rapeseed oil heated to about 170° C. for about 10 hours. Malecka, N., *Die Nahrung*, 35(5):541 (1991).

Transgenic tobacco plant seeds of the present invention have an increased accumulation of squalene when compared to seeds of a native, non-transgenic seed (See Example 10 hereinafter). Thus, in another aspect, the present invention contemplates transgenic plant seeds whose oil contains an increased accumulation of squalene when compared to oil obtained from a native, non-transgenic seed.

In native, non-transgenic plants squalene accumulation is less than about 0.01 weight percent of the dry weight on the plant. In transgenic plants of the present invention squalene accumulation increases to a level of from about 0.115 weight percent of dry weight (tobacco and soybean) to 0.56 weight percent (cotton) (See Examples 5-9 hereinafter).

I. Harvesting of Sterols and Squalene

If desired, after cultivation, the transgenic plant is harvested to recover the sterol or squalene product. This harvesting step can consist of harvesting a callus culture, the entire plant, or only the leaves, or roots of the plant. This step can either kill the plant or, if only a non-essential portion of the transgenic plant is harvested, can permit the remainder of the plant to continue to grow.

In preferred embodiments, this harvesting step further comprises the steps of:
(i) homogenizing at least a sterol-containing or a squalene-containing portion of the transgenic plant to produce a plant pulp and using the sterol- or squalene-containing pulp directly, as in dried pellets or tablets as where an animal food is contemplated; or
(ii) extracting the squalene or sterol(s) from the plant pulp with an appropriate solvent such as an organic solvent or by supercritical extraction [Favati et al., *J. Food Sci.*, 53:1532 (1988) and the citations therein] to produce a sterol- or squalene-containing liquid solution or suspension; and
(iii) isolating the squalene or sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of squalene or the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol or squalene can be extracted from the plant pulp produced above to form a sterol-or squalene-containing solution or suspension. Such extraction processes are common and well known to one skilled in this art. For example, the extracting step can consist of soaking or immersing the plant pulp in a suitable solvent. This suitable solvent is capable of dissolving or suspending the squalene or sterol present in the plant pulp to produce a sterol- or squalene-containing solution or suspension. Solvents useful for such an extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction as can steam distillation.

A whole plant or callus culture with an added, exogenous structural gene for a polypeptide having HMG-CoA reductase activity is grown under suitable conditions for a period of time sufficient for squalene or sterols to be synthesized and accumulated. The sterol- or squalene-containing plant cells, preferably in dried form, are then lysed chemically or mechanically, and the squalene or sterol is extracted from the lysed cells using a liquid organic solvent or steam distillation, as described before, to form a sterol- or squalene-containing liquid solution or suspension. The squalene or sterol is thereafter isolated from the liquid solution or suspension by usual means such as chromatography.

The squalene or sterol is isolated from the solution or suspension produced above using methods that are well known to those skilled in the art of squalene and sterol isolation. These methods include, but are not limited to, purification procedures based on solubility in various liquid media, chromatographic techniques such as column chromatography and the like.

J. Pest Resistance of Transgenic Plants

Certain sterols accumulated by a transgenic plant of the present invention have use as systemic insecticidal or pesticidal agents. As set forth before, because insects are unable to synthesize de novo the steroid nucleus, they depend upon external, dietary sources of delta-5 sterols for production of necessary steroid compounds such as ecdysteroids. See, e.g., Costet et al., *Proc. Natl. Acad. Sci. USA*, 84:643 (1987) and Corio-Costet et al., *Archives of Insect Biochem. Physiol.*, 11:47 (1989).

This embodiment of the present invention relates to a process of increasing pest resistance of a transgenic plant comprising transforming a plant cell of a native, non-transgenic plant with a recombinant DNA molecule comprising a vector operatively linked to a DNA segment that encodes the catalytic region of HMG-CoA reductase, and a promoter suitable for driving the expression of said reductase in that plant, and regenerating a transgenic plant from the transformed plant cell. In preferred practice, the DNA segment also encodes at least a portion of the linker region but not the membrane binding region of HMG-CoA reductase. Use of the hamster gene is particularly preferred. The resulting transgenic plant exhibits enhanced resistance to insect pests.

A transgenic plant is then preferably grown to sexual maturity and used to transmit its enhanced pest resistance to its offspring. Transgenic plants can also themselves be used agriculturally.

Tobacco hornworm larvae grown on the leaves of transgenic plants regenerated from plant cells transformed with a truncated hamster HMG-CoA reductase gene, which transgenic plants have increased levels of non-delta-5 sterol and, particularly cycloartenol, demonstrated retarded development. Preliminary studies also indicate that tobacco bud worms (*Heliothis virescens*) fed on leaves of a similar transgenic plant exhibited retarded development under similar conditions.

Other insects such as *Locusta migratoria* show marked developmental arrest and growth abnormalities when reared on plants deficient in delta-5 sterols. Costet et al., *Proc. Soc. Natl. Acad. Sci., USA*, 84:643 (1987); Corro-Costet et al., *Archives Insect Biochem. Physiol.*, 11:47 (1989).

Further, initial feeding studies show that the growth and development at various stages of Heliothis and European corn borer, *Ostrinia nubialis*, are markedly inhibited by feeding those insect pests on artificial diets having reduced levels of delta-5 sterols and increased levels of non-delta-5 sterols.

K. Harvesting of Transgenic Seed Oil

Oil is extracted from transgenic plant seeds of the present invention by methods well known in the art. By way of example, oil can be extracted from plant seeds using extraction methods set forth above for harvesting sterols and squalene from transgenic plants. Alternatively, oil can be extracted from transgenic plant seeds by usually used methods for obtaining seed oils such as by crushing the seeds to produce a pulp and then pressing the pulp to obtain oil. The pulp can also be extracted with appropriate solvents (e.g. benzene) to obtain the oil. *Industrial Chemistry: A Manual for the Student and Manufacturer*, ed. by A. Rogers and A. B. Aubert, D. Van Nostrand Co., New York, pages 547–548 (1912).

The following examples illustrate the best mode of carrying out the invention and are not to be construed as limiting of the specification and claims in any way.

BEST MODE FOR CARRYING OUT THE INVENTION

EXAMPLE 1

Transformation of Plant Cells

Plant cells were transformed in accordance with standard methods for expressing foreign genes in plants. Schardl et al., *Gene*, 61:1–11 (1987). A pKYLX series of vectors was used as the expression system. Preferred vectors are plasmids pKYLX6 and pKYLX7. Berger et al., *Proc. Natl. Acad. Sci. USA*, 86:8402–8406 (1989).

Transformations were performed with a truncated Hamster HMG-CoA reductase gene (HMGR-$\Delta$227) obtained from the laboratories of Dr. J. L. Goldstein, See, e.g., Gil et al., *Cell*, 41:249–258(1985); Bard et al., *Journal of General Microbiology*, 125:415–420(1981).

The HMGR-$\Delta$227 gene was incorporated into modified vectors pKYLX6 (an *E. coli* vector designed for intermediate constructs) and pKYLX7 (an *A. tunefaciens* vector designed for integration of cloned genes). Berger et al., *Proc. Natl. Acad. Sci. USA*, 86:8402–8406 (1989). The modified vectors pKYLX61 and pKYLX71 contained Hind III, Xho I, Bam HI, Pst I, and Sst I sites in place of the original Hind III Sst I fragment multiple cloning site region.

The HMGR-$\Delta$227 gene was digested with Bam HI and Sst I, and the approximately, 2500 bp HMGR-$\Delta$227-Bam HI-Sst I fragment was inserted into plasmid pKYLX61. The resulting HMGR$\Delta$227-pKYLX61 construct was cleaved with Eco RI and Cla I, and an approximately 4000 bp fragment containing the promoter-gene-terminator portion was inserted into corresponding sites of pKYLX71 to generate plasmid HMGR$\Delta$227-pKYLX71 (see FIG. 5). In plasmid HMGR$\Delta$227-KYLX71, the truncated HMGR-$\Delta$227 gene is under control of the strong, constitutive CaMV 35S promoter.

The HMGR$\Delta$227-pKYLX71 plasmid was mobilized into *Agrobacterium tumefaciens* by a standard triparental mating between *E. coli*, harboring the HMGR$\Delta$227-pKYLX71 construct, *Argrobacterium tumefaciens*, harboring a disarmed Ti-plasmid, GV3850, and *E. coli* harboring the conjugation helper plasmid pRK2013. See, e.g., Schardl, et al., *Gene*, 61:1–11 (1987); Ditta et al., *Proc. Natl. Acad. Sci. USA* 77:7347–7351 (1980). As a result of the cross, Agrobacterium harboring the HMGR$\Delta$227-pKYLX71 construct, was selected for by resistance to rifampicin (encoded on the chromosome of Agrobacterium), and to tetracycline and kanamycin (encoded on the pKYLX71 vector).

Alternatively, the HMGR $\Delta$-227-KYLX71 plasmid is mobilized into *Agrobacterium tumefaciens* strain 281, which contains a fully armed T-DNA plasmid to form a binary plasmid strain A281-$\Delta$227. See, e.g., Schardl et al. *Gene*, 61:1–11 (1987) and Montoya et al., *J. Bacteriol.*, 129:101 (1977) (See Example 7 hereinafter).

*Nicotiana tabacum* L. cv. *xanthii* (*N. tabacum*) was transformed by the well known "leaf disk method". Horsch et al., *Science* 27:1229–1231 (1985). Leaf disks were incubated with Agrobacteria containing plasmid $\Delta$227-pKYLX71 for about 3 days. Transformed tissue was selected for by resistance to kanamycin (encoded by the pKYLX71 vector), cured of Agrobacteria using the antibiotic mefoxin, and regenerated into whole plants. Horsch et al., *Science*, 27:1229–1231 (1985).

Transgenic plant tissue was checked for the presence of integrated copies of the HMGR $\Delta$227 gene sequences by the method of Mettler, *Plant Mol. Biol. Reporter*, 5:346–349 (1987). RNA transcription levels were determined by northern blotting or S-1 protection assays. Maniatis et al., *Molecular Cloning: A Laboratory Manual*, Cold Spring Harbour Lab., Cold Spring Harbour, N.Y. (1982).

Transgenic plants exhibiting HMG-CoA reductase activity greater than native, non-transgenic (control) plants or transgenic plants regenerated from plant cells transformed without the HMGR-$\Delta$227-construct were sexually crossed with themselves, to generate progeny.

EXAMPLE 2

HMG-CoA Reductase Enzyme Activity in Transgenic Plants

Transgenic plants were screened for expression of the truncated HMGR gene by examining HMG-CoA reductase activity in the 100,000xG supernatant of lysed cells using a standard assay, Chappell et al., *Plant Physiol.*, 85:469–473 (1987).

Soluble HMG-CoA reductase enzyme activity was measured in callus cultures grown on selection (kanamycin) medium, seedlings germinated in the presence of kanamycin or on moistened filter paper, and leaves of various sizes from plants grown in the greenhouse. Examplary results of studies of HMG-CoA reductase activity in leaves from greenhouse-grown plants are also summarized in Table 2 below:

TABLE 2

| Plant Sample No. | Total HMG-CoA Reductase Activity (pmol/hr./leaf) | % of Control |
| --- | --- | --- |
| Control | | |
| 30 | 258 | 100 |
| Transgenic | | |
| 5 | 860 | 300 |
| 14 | 1,100 | 390 |
| 15 | 633 | 220 |
| 18 | 456 | 160 |
| 23 | 713 | 250 |

The control plant, 30, was transformed with a selection marker but not with the $\Delta$227 gene. Transgenic plants 5, 14, 15, 18 and 23 were regenerated from plant cells transformed with the HMGR-$\Delta$227 gene, as discussed above.

Total HMG-CoA reductase activity was 1.6 to 3.9 times greater in transgenic plants harboring the $\Delta$227 gene as compared to the control plant.

EXAMPLE 3

Sterol Accumulation in Transgenic Plants

Regenerated, transgenic *N. tabacum*, from cells transformed with the HMGR-$\Delta$227 gene according to the process of Example 1 were analyzed for total sterol content. The results are presented in Table 3.

TABLE 3

| Plant Sample | HMG-CoA Reductase (pmol mg dry wt.) | Total Sterols (% of dry wt) |
| --- | --- | --- |
| Control Plants (n = 6) | 2.00 ± 0.19 | 0.27 ± 0.02 |
| Transgenic | 5.75 ± 1.55 | 0.89 ± 0.17 |

TABLE 3-continued

| Plant Sample | HMG-CoA Reductase (pmol mg dry wt.) | Total Sterols (% of dry wt) |
|---|---|---|
| Plants (n = 12) | | |

Transgenic plants had elevated HMG-CoA reductase activity and increased sterol content.

In addition to determining total sterol content, transgenic *N. tabacum* were examined for the accumulation of squalene and specific sterols. The designated plant tissues were lyophilized and heated with agitation in an alcohol/water solution containing potassium hydroxide to effect extraction and saponification of sterols and sterol esters. Free sterols were then extracted into heptane and measured by gas chromatography using an internal standard. The results of such an analysis in a control (Cntrl) and a transgenic (Trg) plant are presented in Table 4.

TABLE 4

| Accumulated Product | Percent Dry Weight of Squalene and Sterols | | | | | |
|---|---|---|---|---|---|---|
| | Callus | | Leaf | | Root | |
| | Cntrl | Trg | Cntrl | Trg | Cntrl | Trg |
| Squalene | tr | 0.025 | 0.01 | 0.126 | tr | 0.019 |
| Sterols | | | | | | |
| Campesterol | 0.009 | 0.021 | 0.057 | 0.056 | 0.058 | 0.022 |
| Cholesterol | 0.004 | tr | tr | tr | tr | tr |
| Cycloartenol | 0.003 | 0.258 | 0.011 | 0.678 | 0.039 | 0.642 |
| Sitosterol | 0.027 | 0.077 | 0.083 | 0.187 | 0.029 | 0.194 |
| Stigmasterol | 0.003 | 0.012 | 0.132 | 0.078 | tr | 0.238 | tr = trace (<0.001 percent dry wt.)

In the control plant, cycloartenol represented from about 3(0.011/0.283) percent dry weight (leaf) to about 30(0.039/0.126) percent dry weight (root) of total sterol accumulation. The predominant sterols accumulated by control plants (i.e. sitosterol, campesterol) are Δ5-sterol derivatives of cycloartenol that have undergone additional metabolic transformation.

As a result of transformation with the HMGR-Δ227 gene, the ratio of cycloartenol to its derivatives is reversed. In transgenic plants, cycloartenol accumulation represents from about 60 (root) to about 70 (leaf) percent by weight of total sterol accumulation.

These data show that transgenic plants of the present invention overaccumulate sterols relative to a native, non-transgenic plant. Transgenic, heterozygous plants overaccumulate total sterols to a level about twice that found in a native plant. The data further show that transgenic plants containing a single added, exogenous gene over-accumulate cycloartenol to a level about ten to about one hundred times greater than found in a native plant.

EXAMPLE 4

Insecticidal Effects of Transgenie Plants

First instar larvae of the tobacco pests tobacco hornworm (*Manduca sexta*), were placed onto leaves of control or HMGR-Δ227 transgenic *N. tabacum* on a moistened filtered paper in a petri dish. Additional leaf material, from control or transgenic plants, was added to each dish, and the larvae were grown for an additional 7 days. Larvae were then examined to determine growth and development. The results are presented in Table 5.

TABLE 5

| | Control (n = 14) | Transgenic (n = 13) |
|---|---|---|
| Development | | |
| % of larvae in second instar | 28.6 | 100 |
| % of larvae in premolt or third instar | 71.4 | 0 |
| Growth | | |
| Fresh Wet Weight (mg) | 42.8 | 24.4 |

Tobacco hornworm (Manduca sexta) larvae grown on leaves from transgenic plants (from HMGR-Δ227-transformed cells) demonstrated retarded development (no progression beyond the second instar stage) and inhibited growth (wet weight) as compared to controls. The cycloartenol levels of the control and transgenic plants used in this study were 0,017 and 1.02 percent of dry leaf weight, respectively. This study thus illustrates both the process of increasing the accumulation of cycloartenol in a plant and of enhancing pest resistance in a plant.

Preliminary studies with a member of the Heliothis group of insect pests, the tobacco bud worm (*Heliothis virescens*), indicate a slower growth rate for insects fed on leaves of transgenic plant 14 (Example 2) than on leaves of the native, non-transgenic, control plant 30 (Example 2).

EXAMPLE 5

Homozygous Transgenic Plants

One of the previously described transformed plants, plant 14 of Example 2, was selfed; i.e., sexually mated with itself.

Twelve seeds from that cross were germinated and raised into plants. The tissues of those siblings were then analyzed for HMG-CoA reductase activity, total squalene (squalene plus squalene monoepoxide), and total sterol content as described in Example 3. The specific activity of HMG-CoA reductase was also calculated. The results of that assay compared to similar data from siblings from a selfing control plant 30 (Example 2) are presented in Table 6, below.

TABLE 6

| Plant | HMGR Activity[1] | Protein[2] | Specific Activity[3] | Sterols[4] | Squalene[5] |
|---|---|---|---|---|---|
| 30-1 | 3.78 | 30.22 | 184 | 0.20 | <0.01 |
| 30-2 | 2.20 | 30.00 | 146 | 0.25 | <0.01 |
| 30-3 | 1.44 | 18.70 | 154 | 0.29 | <0.01 |
| 30-4 | 2.13 | 23.67 | 180 | 0.31 | <0.01 |
| 30-5 | 1.70 | 19.27 | 176 | 0.36 | <0.01 |
| 30-6 | 1.77 | 19.32 | 183 | 0.22 | <0.01 |
| 14-1 | 1.36 | 23.60 | 115 | 0.21 | 0.142 |
| 14-2 | 2.07 | 26.55 | 156 | 0.17 | 0.127 |
| 14-3 | 10.28 | 17.60 | 1168 | 1.10 | 0.101 |
| 14-4 | 7.08 | 27.25 | 520 | 0.74 | 0.114 |
| 14-5 | 4.13 | 20.92 | 394 | 1.59 | 0.107 |
| 14-6 | 1.58 | 11.00 | 143 | 0.25 | 0.086 |
| 14-7* | 20.35 | 16.77 | 2426 | 2.05 | 0.119 |
| 14-8 | 4.87 | 24.20 | 402 | 0.97 | 0.174 |
| 14-9 | 2.37 | 12.95 | 366 | 0.19 | 0.126 |
| 14-10 | 7.94 | 11.00 | 1444 | 1.02 | 0.075 |
| 14-11 | 2.56 | 15.25 | 334 | 1.10 | 0.082 |
| 14-12 | 4.39 | 21.10 | 416 | 1.29 | 0.130 |

[1] pmoles/0.5 hours.
[2] micrograms (μg).
[3] pmoles of enzyme/hour/mg of total protein.
[4] percentage of dry weight.
[5] squalene plus squalene monoepoxide (percentage of dry weight
*this plant died.

The phenotype for altered sterol composition segregated in a standard Mendelian manner with a ratio of three plants containing the elevated HMG-CoA reductase activity to one plant lacking the elevated HMG-CoA reductase activity.

On the basis of the above data, the plants were classified as (a) having no added HMG-CoA reductase gene, or (b) containing the added gene. Illustratively, plant 14-2 was thus determined to lack the added gene and plant 14-8 was determined to contain the added gene.

Southern blot analyses were performed on the transformed plants and confirmed the presence of the integrated gene.

These data show that seeds from a transformed plant are capable of expressing enhanced squalene and sterol accumulation.

Taken together with the data of Example 3, these data show that the transgenic plants of the present invention overaccumulate squalene, total sterol, and particularly non-utilizable sterols relative to a native plant and that such plants are capable of producing seeds, which germinate into transgenic plants that overaccumulate squalene and those sterols.

Seeds from a selfing of transgenic plant 14-8 were deposited pursuant to the Budapest Treaty requirements with the American Type Culture Collection (ATCC) at 12301 Parklawn Drive, Rockville, Md. 20852 U.S.A. on Sep. 28, 1990, and were assigned accession number ATCC 40904.

The above deposit is made for a term of at least thirty (30) years and at least five (5) years after the most recent request for the furnishing of a sample of the deposit was received by the depository.

EXAMPLE 6

Transformation of Cotton

The cotton plant cell line Coker 312-5A was transformed with HMGR-Δ227 gene incorporated into plasmid pKYLX6. Transformation by Agrobacterium-mediated gene transfer was accomplished using the method of Trolinder et al., *Plant Cell Reports*, 6:231-234 (1987).

Total sterol, delta-5 sterol, non-delta-5 sterol and squalene levels were determined in control, non-transgenic and transgenic calli as described in Example 3. The results of those studies are presented below in Table 7.

TABLE 7

| Plant | Total Sterol | Non-Util Sterol[1] | Util Sterol[2] | Squalene |
|---|---|---|---|---|
| Control | 0.16 | 0.03 | 0.13 | <0.002 |
| Tr-1 | 0.48 | 0.39 | 0.09 | 0.2 |
| Tr-2 | 0.53 | 0.44 | 0.09 | 0.39 |
| Tr-3 | 0.79 | 0.72 | 0.07 | 1.1 |

*all data are expressed as percentage of dry weight. Tr-1, Tr-2, and Tr-3 are transgenic calli one, two and three
[1]non-delta-5 sterols
[2]delta-5 sterols These data show that transgenic cotton calli of the present invention overaccumulate squalene, total sterol and non-utilizable sterols relative to native, non-transgenic calli.

EXAMPLE 7

Transformation of Soybean

The HMGR 227-KYLX71 plasmid was mobilized into *Agrobacterium tumefaciens* strain 281. Strain 281 contains a fully armed T-DNA plasmid. Montoya et al., *J. Bacteriol.*, 129:101-107 (1977).

The resulting strain A281:227 is a binary plasmid strain. Upon transfection, transformed plant cells proliferate as an undifferentiated transgenic callus since the tumor inducing (Ti) genes are transferred with KYLX-227 as cointegrates. The advantage of this system is that no selection is needed for transformants because they are self-proliferating.

This is particularly advantageous in strains that have low transformation frequency and would not hold up well under stringent selection pressure. This expands the possible host range, including even woody strains, and existing vectors can be used without further engineering.

Sterilized cotyledons from soybean *Glycine max* cv Peking were inoculated with A281:227 by placing a small aliquot of the Agrobacterium culture in cuts made on the inner surface of the tissue. The infected cotyledons were then put on Gamborg's B5 media lacking hormones and cultured for two weeks. Gamborg et al., *Exp. Cell Res.*, 50:1151-1158 (1968). Transgenic calli were then isolated and analyzed for total squalene, total sterol and total cyclopropyl-pentacyclic (non-utilizable) sterol levels as described in Example 3. The results of those studies are presented below in Table 8.

TABLE 8*

| Plant | Total Sterol | Cyclopropyl/Pentacyclic Sterol Callus | Squalene |
|---|---|---|---|
| Control | 0.37 | 0.002 | 0.022 |
| Transgenic | 0.85 | 0.12 | 0.233 |

*Data are presented as a percentage of dry weight. Data for the control represent the average of five vector controls.
Transgenic represents a single transformant designated D-13.

Pentacyclic triterpenoids are sterol compounds having a fifth ring formed from cyclization of the steroidal 17-position side chain. Examples of these compounds include alpha-amyrin, beta-amyrin and lupeol. Although these compounds are found in a wide variety of plants, they are usually present in only trace amounts. These compounds and their conjugates (e.g. saponins) are reported to have medicinal and insecticidal properties.

The positive identification of pentacyclictype (non-utilizable) compounds in transgenic soybean callus was made by gas chromatography-mass spectroscopy (GC-MS). Quantification by GC analysis is difficult because these compounds coelute with cyclopropyl sterols. The results for soybean transformants given in Table 8, above, therefore give cyclopropyl and pentacyclic sterols as a combined quantity.

EXAMPLE 8

Transformation of Tomato

Hypocotyls from tomato *Lycopersicon esculentum* cv. UC82B were transformed as described in accordance with the procedures of Example 7 for soybean. After two weeks the transgenic calli were isolated and analyzed for sterol and squalene levels as described in Example 3.

The results of these studies are presented below in Table 9.

TABLE 9

|   | Total Sterol | Cyclopropyl | Squalene |
|---|---|---|---|
| CTRL | 0.04 | <0.002 | 0.002 |
| TRNSG |  |  |  |
| #10 | 1.42 | 0.84 | 0.142 |
| #19 | 0.56 | 0.21 | 0.039 |

*Data are expressed as percentage of dry weight
CTRL = non-transgenic control
TRNSG = transgenic The data show that calli of tomato plant cells transformed by a process of the present invention results in increases in total sterol, cyclopropyl (non-delta-5) sterols and squalene accumulation.

EXAMPLE 9

Transformation of Alfalfa

Hypocotyls from alfalfa strain RYSI were transformed in accordance with the procedures of Example 3 for tobacco. After three or four weeks transgenic calli were isolated and analyzed for sterol and squalene levels as described in Example 3. The results of those studies are shown below in Table 10.

TABLE 10*

|   | Total Sterol | Cyclopropyl/ Pentacyclic Sterol | Squalene |
|---|---|---|---|
| CTRL | 0.24 | <0.002 | 0.002 |
| TRNSG | 1.26 | 0.99 | 0.052 |

*Data are expressed as percentage of dry weight
CTRL = non-transgenic control
TRNSG = transgenic The data from Table 10 show that transgenic alfalfa calli demonstrate large increases in total sterol, pentacyclic and cyclopropyl sterols, and squalene accumulation when compared to a native, non-transgenic calli.

EXAMPLE 10

Transgenic Tobacco Seeds

Transgenic tobacco seeds produced in accordance with the procedures of Example 1 were assayed for total sterol and squalene accumulation as described in Example 3. The results of those studies are presented below in Table 11.

TABLE 11*

|   | Total Sterol | Cyclopropyl | Squalene |
|---|---|---|---|
| CTRL | 0.286 | 0.031 | 0.011 |
| TRNSG |  |  |  |
| #5 | 0.509 | 0.123 | 0.047 |
| #19 | 0.714 | 0.163 | 0.042 |

*Data are expressed as percentage of dry weight
CTRL = non-transgenic control
TRNSG = transgenic The data in Table 11 show that transgenic tobacco seeds of the present invention have an increased accumulation of total sterol, cyclopropyl sterol (non-delta-5 sterol) and squalene when compared to a native, non-transgenic seed of the same strain.

The present invention has been described with respect to preferred embodiments. It is readily apparent to those skilled in the art that modifications and/or variations of the disclosed subject matter can be made without departing from the scope of the invention set forth herein.

---

We claim:

1. A process of increasing insect resistance in a transgenic plant said process comprising:
 (a) transforming a plant cell with a recombinant DNA molecule comprising a vector operatively linked to a DNA segment that encodes a polypeptide having HMG-CoA reductase activity, and a promoter suitable for driving the expression of said polypeptide in said plant cell to form a transformed plant cell; and
 (b) regenerating said transformed plant cell into said transgenic plant wherein said plant exhibits increased insect resistance.

2. The process according to claim 1 wherein said polypeptide comprises the HMG-CoA reductase catalytic region and at least a portion of the HMG-CoA reductase linker region but is free from the membrane binding region of a HMG-CoA reductase.

3. The process according to claim 1 wherein the promoter is a promoter whose regulatory function is substantially unaffected by the level of sterol in said transgenic plant.

4. The process according to claim 1 wherein the promoter is the CaMV 35S promoter.

5. The process according to claim 1 wherein said plant cell is obtained from plants of the group consisting of tobacco, cotton, soybean, tomato, alfalfa arabidopsis, corn, barley, carrot and guayule.

6. A transgenic plant produced in accordance with the process of claim 1.

7. A plant whose genome comprises a DNA structural gene, said structural gene consisting essentially of an HMG-CoA reductase catalytic region and at least a portion of an HMG-CoA reductase linker region, said plant exhibiting increased insect resistance in comparison with a native plant not containing said structural gene.

8. A plant according to claim 7 which is selected from the group consisting of: arabidopsis, tobacco, cotton, soybean, tomato, alfalfa, corn, barley, carrot, and guayule.

9. A method of making a plant having increased insect resistance, said method comprising crossing a plant according to claim 7 with a second plant, and selecting progeny having increased insect resistance.

10. A seed, which upon germination produces a plant whose genome comprises a DNA structural gene, said structural gene consisting essentially of an HMG-CoA reductase catalytic region and at least a portion of an HMG-CoA reductase linker region, said plant exhibiting increased insect resistance in comparison with a native plant not containing said structural gene.

11. A seed according to claim 10 which is selected from the group consisting of: tobacco, cotton, soybean, tomato, alfalfa, corn, barley, carrot, and guayule.

* * * * *